(12) United States Patent
Berlin et al.

(10) Patent No.: US 11,993,573 B2
(45) Date of Patent: May 28, 2024

(54) CHROMANE-SUBSTITUTED, TETRAHYDROQUINOLINE-SUBSTITUTED AND THIOCHROMANE-SUBSTITUTED HETEROAROTINOIDS AS ANTI-CANCER AGENTS

(71) Applicant: THE BOARD OF REGENTS FOR OKLAHOMA STATE UNIVERSITY, Stillwater, OK (US)

(72) Inventors: Kenneth Darrell Berlin, Stillwater, OK (US); Richard A. Bunce, Stillwater, OK (US); Krishna Kumar Gnanasekaran, Mississauga (CA); Field M. Watts, Jr., Fort Smith, AR (US); Donghua Howard Zhou, Edmond, OK (US)

(73) Assignee: THE BOARD OF REGENTS FOR OKLAHOMA STATE UNIVERSITY, Stillwater, OK (US)

( * ) Notice: Subject to any disclaimer, the term of this patent is extended or adjusted under 35 U.S.C. 154(b) by 660 days.

(21) Appl. No.: 17/167,251

(22) Filed: Feb. 4, 2021

(65) Prior Publication Data
US 2021/0163415 A1 Jun. 3, 2021

Related U.S. Application Data

(62) Division of application No. 16/549,337, filed on Aug. 23, 2019, now Pat. No. 10,947,198.

(60) Provisional application No. 62/722,294, filed on Aug. 24, 2018.

(51) Int. Cl.
| | | |
|---|---|---|
| A61P 35/00 | (2006.01) | |
| A61K 31/352 | (2006.01) | |
| A61K 31/382 | (2006.01) | |
| A61K 31/47 | (2006.01) | |
| C07D 215/06 | (2006.01) | |
| C07D 311/70 | (2006.01) | |
| C07D 335/06 | (2006.01) | |

(52) U.S. Cl.
CPC .......... *C07D 215/06* (2013.01); *A61K 31/352* (2013.01); *A61K 31/382* (2013.01); *A61K 31/47* (2013.01); *A61P 35/00* (2018.01); *C07D 311/70* (2013.01); *C07D 335/06* (2013.01)

(58) Field of Classification Search
None
See application file for complete search history.

(56) References Cited

U.S. PATENT DOCUMENTS 6,586,460 B1 * 7/2003 Berlin ................ C07D 311/76
514/432

OTHER PUBLICATIONS

Watts. European Journal of Medicinal Chemistry, 2018, 158, 720-732, available online Sep. 18, 2018 (Year: 2018).*

* cited by examiner

*Primary Examiner* — Noble E Jarrell
(74) *Attorney, Agent, or Firm* — FELLERS, SNIDER, BLANKENSHIP, BAILEY & TIPPENS, P.C.; Terry L. Watt

(57) ABSTRACT

Chemical compounds that inhibit cancer cell growth are provided. The compounds are heteroarotinoids and derivatives thereof with oxygen, nitrogen or sulfur in chroman systems, tetrahydroquinoline systems, and tetrahydrothiochroman systems.

4 Claims, No Drawings

CHROMANE-SUBSTITUTED, TETRAHYDROQUINOLINE-SUBSTITUTED AND THIOCHROMANE-SUBSTITUTED HETEROAROTINOIDS AS ANTI-CANCER AGENTS

CROSS REFERENCE TO RELATED APPLICATIONS

This application is a divisional of U.S. Ser. No. 16/549,337, filed Aug. 23, 2019, and claims the benefit of U.S. Provisional patent Application Ser. No. 62/722,294, filed on Aug. 24, 2018, and incorporates said applications by reference into this document as if fully set out at this point.

TECHNICAL FIELD

The invention relates novel chemical agents that inhibit lung and human ovarian cancer cell growth e.g. via apoptosis, and their use as anticancer agents. The invention more specifically relates to certain heteroarotinoids and derivatives thereof with oxygen, nitrogen or sulfur in chroman systems, tetrahydroquinoline systems, and tetrahydrothiochroman systems.

BACKGROUND

Conventional therapy of advanced stage malignant ovarian cancer (MOC) achieves at best a modest improvement in survival rates. Unfortunately, approximately two thirds of women with ovarian cancer (OC) are diagnosed at an advanced stage (Stage IIIC or IV) [1], and a large proportion of these patients demonstrate chemoresistance. Moreover, those with recurrent drug-resistant ovarian cancer show only 10-15% response rate. Very few treatment options are available, and those that are have only modest success. For example, for partially platinum-sensitive OC (recurrent OC), second-line chemotherapies include PLD and Trabectedin+PLD; and third-line treatments include platinum based re-induction chemotherapy, hormonal treatment and therapies in clinical trials e.g. targeted agents combined with chemotherapy and intraoperative radiation (IORT) combined with intraoperative chemotherapy. However, limitations of these treatments include: the therapeutic effects are generally lower than in women with platinum-sensitive OC; the toxicity of conventional chemotherapy is dose-limiting toxicities; efficacy data is unknown for many therapies being evaluated in clinical trials; and there is typically only minor use of radiotherapy in recurrent ovarian cancer. For platinum resistant/refractory OC, treatment options include paclitaxel, PLD, topotecan; newer chemotherapy agents such as irinotecan, nanoparticles, albumin bound paclitaxel, and sagopilone; and therapeutic agents targeting angiogenesis, PARP, PD-1/PD-L1, growth factor receptors. However, these treatments often result in a poor prognosis, and combined chemotherapies increase toxicity (and severe side effects) with no enhancement of efficacy.

Heteroarotinoids have also been tested for anticancer activity. Examples of heteroarotinoids and recent examples of heteroarotinoid anti-cancer activity can be found in several papers such as: Zacheis, D.; Dhar, A.; Lu, S.; Madler, M. M.; Klucik, J.; Brown, C. W.; Liu, S.; Clement, F.; Subramanian, S.; Weerasekare, G. M.; Berlin, K. D.; Gold, M. A.; Houch, Jr., J. R.; Fountain, K. R.; Benbrook, D. M. Heteroarotinoids inhibit head and neck cancer cell lines in vitro and in vivo through both RAR and RXR retinoic acid receptors. J. Med. Chem. 1999, 42, 4434-4445; Guruswamy, S.; Lightfoot, S.; Gold, M.; Hassan, R.; Berlin, K. D.; Ivey, T. R.; Benbrook, D. M. Effects of retinoids on cancer phenotype and apoptosis in organotypic culture of human carcinoma. J. National Cancer Institute, 2001, 93, 20-29; Chun, K.-H.; Benbrook, D. M.; Berlin, K. D. Hong, W. K.; Lotan, R. Induction of apoptosis in head and neck squamous cell carcinoma (HNSCC) cell lines by heteroarotinoids through a mitochondrial dependent pathway. Cancer Research 2003, 63, 3826-3832; Liu, S.; Brown, C. W.; Berlin, K D.; Dhar, A.; Guruswamy, S.; Brown, D.; Benbrook, D. M. Synthesis of flexible sulfur-containing heteroarotinoids that induce apoptosis and reactive oxygen species with discrimination between malignant and benign cells. J. Med. Chem. 2004, 47, 999-1007; Benbrook, D. M.; Kamelle, S. A.; Guruswamy, S. B.; Lightfoot, S. A.; Hannafon, B. N.; Rutledge, T. L.; Gould, N. S.; Dunn, S. T.; Berlin, K. D. Flexible heteroarotinoids (FLEX-HETS) exhibit improved therapeutic ratios as anti-cancer agents over retinoic acid receptor agonists. Investigational New Drugs. 2005, 23, 417-428; Brown, C. W.; Liu, S.; Klucik, J.; Berlin, K. D.; Brennan, P. J.; Kaur, D.; Benbrook, D. M; Novel heteroarotinoids as potential antagonists of *Mycobacterium bovis* BCG. J. Med. Chem. 2004, 47, 1008-1017; Subramanian, S.; Smith, C. M.; Tabatabai, A.; Bryan, C. D.; Buettner, B.; Hale, S.; Wakefield, C. A.; Benbrook, D. M.; Berlin, K. D. Syntheses of novel heteroarotinoids with receptor activation capabilities and TGase activity. Single crystal analysis of (E)-4-[(2,3-dihydro-2,2,4,4-tetramethyl-2H-1-benzo[b]thiopyran-6-yl)-1-propenyl]-2-methylbenzoic acid. Phosphorus, Sulfur, and Silicon and The Related Elements. 2005, 180, 67-77; Le, T. C.; Berlin, K. D.; Benson, S. D.; Nelson, A. C.; Benbrook, D. M.; Eastman, M.; Bell-Eunice, G. Unusual heteroarotinoids with anticancer activity against ovarian cancer cells. Open Medicinal Chemistry. 2007, 1, 11-23; Lin, Yi-D; Chen, S.; Yue, P.; Zou, W.; Benbrook, D. M.; Liu, S.; Le, T. C.; Berlin, K. D.; Khuri, F. R.; Sun, S.-Y. CAAT/enhancer binding protein homologous protein-dependent death receptor 5 induction is a major component of SHetA2-induced apoptosis in lung cancer cells. Cancer Res. 2008, 68, 5335-5344; Lin, Y.; Lui, X.; Yue, P.; Benbrook, D. M.; Berlin, K. D.; Khuri, F. R.; Sun, S.-Y. Involvement of C-flip and surviving down-regulation in flexible heteroarotinoid-induced apoptosis in lung cancer cells. Molecular Cancer Therapeutics. 2008, 7, 3556-3565; Liu, T.; Masamha, C. Chengedza, S.; Berlin, K. D.; Lightfoot, S.; He, F.; Benbrook, D. M. Development of flexible-heteroarotinoids (Flex-Hets) for kidney cancer. Molecular Cancer Therapeutics. 2009, 8, 1227-1238; Nammalwar, B.; Bunce, R. A.; Benbrook, D. M.; Lu, T.; Li, Hui-Fang; Ya-Dong, C.; Berlin, K. D. Synthesis of N-[3,4-dihydro-4-(acetoxymethyl)-2,2,4-trimethyl-2H-1-benzo-thiopyran-6-yl]-N'-(4-nitrophenyl)thiourea and N-[3,4-(dihydromethyl)-2,2,4-trimethyl-2H-1benzothiopyran-6-yl]-N'(4-nitrophenyl)-thiourea, a major metabolite of N-{3,4-dihydro-2,2,4,4-tetramethyl-2H-1-benzothiopyran-6-yl)-N'-(4-nitrophenyl)thiourea. Phosphorus, Sulfur, and Silicon and The Related Elements. 2011, 186, 189-204. Benbrook, D. M.; Nammalwar, B.; Long, A.; Matsumoto, H.; Singh, A.; Bunce, R. A.; Berlin, K. D. SHetA2 interference with mortalin binding to p66she and p53 identified using drug-conjugate magnetic microspheres. Investigational New Drugs. 2014, 32, 412-423; Gnanasekaran, K. K.; Benbrook, D. M.; Nammalwar, B.; Thavathiru, E.; Bunce, R. A.; Berlin, K. D. Synthesis and evaluation of second generation Flex-Het scaffolds against the human ovarian cancer A2780 cell line. Eur. Journal of Medicinal Chemistry, 2015, 96, 209-217; Liu, S.; Zhou, G.; Lo, S. N. H.; Louie, M.; Rajagopalan, V. SHetA2, A new cancer-preventive drug candidate, Chapter 3 in "Anti-Cancer Drug Preventive Drug Candidates". InTech, 2016, DOI 10.5772/65365 (this a review); Sharma, A.; Benbrook, D. M.; Woo, S. Pharmacokinetics and inter-species scaling of a novel, orally-bioavailable anti-cancer drug, SHetA2. *PLOS,* 2018, 13 (4) https://doi.org/10.1371; Mahjabeen, S.; Hatipoglu, M. K.; Chandra, V.; Benbrook, D. M.; Garcia-Contreras, L. Optimization of a vaginal suppository formulation to deliver SHetA2 as a novel treatment for cervical dysplasia. Journal of Pharmaceutical Sciences. 2018, 107, 638-646.

The heteroarotinoid anticancer agent SHetA2 [CAS #NSC-726189, N-(2,3-dihydro-2,2,4,4-tetramethyl-6-benzothiopyranyl)-N-(4-nitrophenyl)urea], inhibits the growth of all 60 cancer cell lines that are available from the National Cancer Institute, and exhibits essentially no toxicity toward normal tissues, no skin irritation, and does not cause birth defects in animal studies. Several derivatives of SHetA2 have exhibited strong activity against Non-Small Cell Lung Cancer (NSCLC) [Yi-D Lin, S. Chen, P. Yue, W. Zou, D. et. al. Cancer Res. 2008, 68, 5335-5344. Y. Lin, X. Lui, P. Yue, D. M. Benbrook, et. al. Molecular Cancer Therapeutics. 2008, 7, 3556-3565.] NSCLC is especially difficult to treat. Agents such as KEYTRUDA®, OPDIVO®, and ZYKADIA® are used but many side effects occur with these clinical agents.

New anti-cancer agents that exhibit improved anti-cancer activity without causing deleterious side effects are needed.

Before proceeding to a description of the present invention, however, it should be noted and remembered that the description of the invention which follows, together with the accompanying drawings, should not be construed as limiting the invention to the examples (or embodiments) shown and described. This is so because those skilled in the art to which the invention pertains will be able to devise other forms of this invention within the ambit of the appended claims.

SUMMARY

The present disclosure describes the synthesis and testing of new heteroarotinoids with chroman-, tetrahydroquinoline- or thiochroman-fused systems bonded to an aryl group via a urea or thiourea linker. The new compounds are the result of important chemical improvements that were made to the structure of the known anticancer agent SHetA2 in order to enhance its biological activity. For example, incorporation of a chroman (oxygen-atom at position 1) or tetrahydroquinoline (nitrogen atom at position 1) is a new unique transformation in this class of heterocycles. The new compounds exhibited a range of major cancer inhibitory activities, depending on the substitutions of [$NO_2$, $CF_3$, $OCF_3$] the aryl group attached to the linker. The presence of geminal diethyl groups at C-1 and C-4 in the chroman unit appeared to contribute favorably to activity. Without being bound by theory, it is believed that the linkers give more flexibility for docking to the protein mortalin, which is believed to be the target receptor and to be involved in the progress of a cell becoming cancerous. And, advantageously, it is well known that urea derivatives are easily handled by the body so that the new compounds will behave similarly and, as noted with SHetA2, are metabolized in a similar manner. Among these new compounds, 32 compounds outperformed SHetA2 in the inhibition of human A2780 ovarian cancer cells, and 19 of these compounds further exhibited improved potency (measured in half-maximal inhibitory concentration, $IC_{50}$). Several of the best compounds achieved 92-95% efficacy (measured in growth inhibition) and 2 μM $IC_{50}$, which were better than SHetA2 (84%, 3 μM). The new compounds are expected to be effective in other cancer cell lines and to have low toxicity in normal cells.

It is an object of the disclosure to provide a compound of Formula I

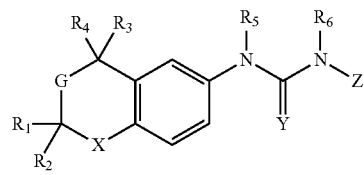

wherein,
- $R_1$ and $R_2$ are optionally C1-C5 substituted alkyl;
- $R_3$ and $R_4$ are optionally C1-C5 substituted alkyl;
- G is $CH_2$, C=O or CHOH;
- X is S, O, NR or $N^+(R)_2$ where R is hydrogen or an optionally substituted C1-C5 alkyl;
- $R_5$ and $R_6$ are hydrogen or optionally substituted C1-C5 alkyl;
- Y is O or S; and
- Z is an optionally substituted phenyl, optionally substituted phenylamino or optionally substituted benzylamide;

and salts, solvates and hydrates thereof,
with the caveat that the compound is not ShetA2 with the formula

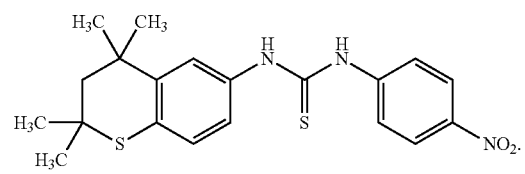 [SMILES: CC1(C)CC(C)(C)c2cc(NC(=S)Nc3ccc([N+](=O)[O-])cc3)ccc2S1]

In some aspects, the compound has a formula:

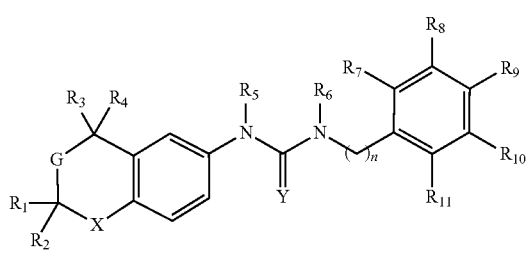

wherein,
- $R_1$ and $R_2$ are optionally C1-C5 substituted alkyl;
- $R_3$ and $R_4$ are optionally C1-C5 substituted alkyl;
- G is $CH_2$, C=O or CHOH;
- X is S, O, NR or $N^+(R)_2$ where R is hydrogen or an optionally substituted C1-C5 alkyl;
- $R_5$ and $R_6$ are hydrogen or optionally substituted C1-C5 alkyl;
- Y is O or S;
- n is 0, 1, 2, 3, or 4; and
- $R_7$ to $R_{11}$ are independently selected from a group consisting of hydrogen, halogen, CN, $NO_2$, OH, optionally substituted alkyl, optionally substituted alkoxy, optionally substituted haloalkyl, optionally substituted haloalkoxy, ester or sulfonamide;
and salts, solvates and hydrates thereof.

In other aspects, the compound has a formula:

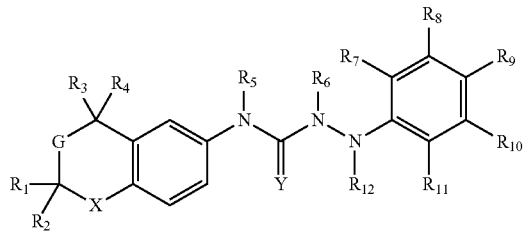

wherein,
$R_1$ and $R_2$ are optionally C1-C5 substituted alkyl;
$R_3$ and $R_4$ are optionally C1-C5 substituted alkyl;
G is $CH_2$, C=O or CHOH;
X is S, O, NR or $N^+(R)_2$ where R is hydrogen or an optionally substituted C1-C5 alkyl;
$R_5$, $R_6$ and $R_{12}$ are hydrogen or optionally substituted C1-C5 alkyl;
Y is O or S; and
$R_7$ to $R_{11}$ are independently selected from a group consisting of hydrogen, halogen, CN, $NO_2$, OH, optionally substituted alkyl, optionally substituted alkoxy, optionally substituted haloalkyl, optionally substituted haloalkoxy, ester or sulfonamide;
and salts, solvates and hydrates thereof.

In yet further aspects, the compound has a formula:

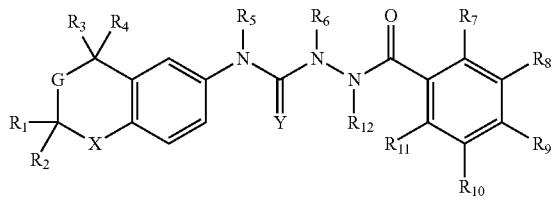

wherein,
$R_1$ and $R_2$ are optionally C1-C5 substituted alkyl;
$R_3$ and $R_4$ are optionally C1-C5 substituted alkyl;
G is $CH_2$, C=O or CHOH;
X is S, O, NR or $N^+(R)_2$ where R is hydrogen or an optionally substituted C1-C5 alkyl;
$R_5$, $R_6$ and $R_{12}$ are hydrogen or optionally substituted C1-C5 alkyl;
Y is O or S; and
$R_7$ to $R_{11}$ are independently selected from a group consisting of hydrogen, halogen, CN, $NO_2$, OH, optionally substituted alkyl, optionally substituted alkoxy, optionally substituted haloalkyl, optionally substituted haloalkoxy, ester or sulfonamide;
and salts, solvates and hydrates thereof.

In yet additional aspects, $R_7$, $R_8$, $R_{10}$, $R_{11}$ are hydrogen and $R_9$ is hydrogen, $CF_3$, $OCF_3$, CN, Cl, $OCH_3$ or OH.

In further aspects, $R_7$, $R_9$, $R_{10}$, $R_{11}$ are hydrogen and $R_8$ is $CF_3$, $OCF_3$, CN, Cl, $OCH_3$ or OH.

In yet further aspects, $R_7$, $R_9$, $R_{11}$ are hydrogen and $R_8$, $R_{10}$ are $CF_3$, $OCF_3$, CN, Cl, $OCH_3$ or OH.

In some aspects, the compound has a formula:

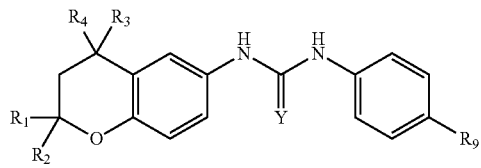

wherein,
$R_1$ and $R_2$ are hydrogen, $CH_3$ or $C_2H_5$;
$R_3$ and $R_4$ are $CH_3$ or $C_2H_5$;
Y is O or S;
$R_9$ is $CF_3$, $OCF_3$, CN, Cl, $OCH_3$ or OH
and salts, solvates and hydrates thereof.

In additional aspects, the compound has a formula:

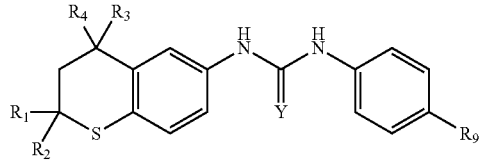

wherein,
$R_1$ and $R_2$ are hydrogen, $CH_3$ or $C_2H_5$;
$R_3$ and $R_4$ are $CH_3$ or $C_2H_5$;
Y is O or S;
$R_9$ is $CF_3$, $OCF_3$, CN, Cl, $OCH_3$ or OH
and salts, solvates and hydrates thereof.

In yet other aspects, the compound has a formula:

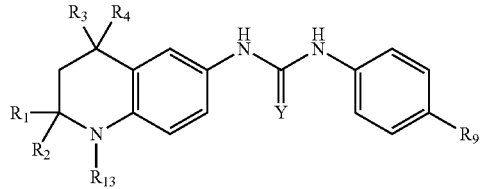

wherein,
$R_1$ and $R_2$ are hydrogen, $CH_3$ or $C_2H_5$;
$R_3$ and $R_4$ are $CH_3$ or $C_2H_5$;
Y is O or S;
$R_9$ is $CF_3$, $OCF_3$, CN, Cl, $OCH_3$ or OH
$R_{13}$ is H or $CH_3$;
and salts, solvates and hydrates thereof.

In even further aspects, the compound has a formula:

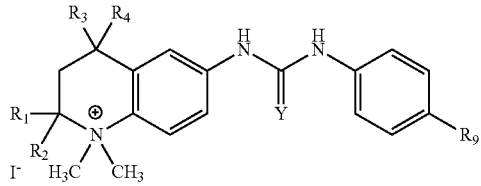

wherein,
$R_1$ and $R_2$ are hydrogen, $CH_3$ or $C_2H_5$;
$R_3$ and $R_4$ are $CH_3$ or $C_2H_5$;
Y is O or S;
$R_9$ is $CF_3$, $OCF_3$, CN, Cl, $OCH_3$ or OH
and salts, solvates and hydrates thereof.

In some aspects, the compound has a formula:

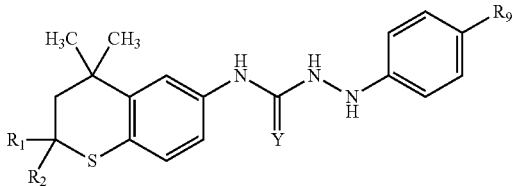

wherein,
$R_1$ and $R_2$ are hydrogen, $CH_3$ or $C_2H_5$;
Y is O or S; and
$R_9$ is $CF_3$, $OCF_3$, CN, Cl, $OCH_3$ or OH;
and salts, solvates and hydrates thereof.

In additional aspects, the compound has a formula:

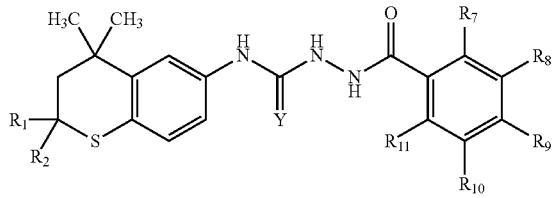

wherein,
$R_1$ and $R_2$ are hydrogen, $CH_3$ or $C_2H_5$;
Y is O or S; and
$R_7$ to $R_{11}$ are independently selected from a group consisting of hydrogen, $CF_3$, $OCF_3$, CN, Cl, $OCH_3$ or OH;
and salts, solvates and hydrates thereof.

In further aspects, the compound is elected from:
1-(4-Nitrophenyl)-3-(2,2,4,4-tetramethylchroman-6-yl)thiourea;
Ethyl 4-(3-(2,2,4,4-Tetramethylchroman-6-yl)thioureido)benzoate;
1-(2,2,4,4-Tetramethylchroman-6-yl)-3-(4-(trifluoromethyl)phenyl)thiourea;
4-(3-(2,2,4,4-Tetramethylchroman-6-yl)thioureido)benzenesulfonamide;
1-(2,2,4,4-Tetramethylchroman-6-yl)-3-(4-(trifluoromethyl)phenyl)urea;
1-(4-Cyanophenyl)-3-(2,2,4,4-tetramethylchroman-6-yl)urea;
1-(2,2,4,4-Tetramethylchroman-6-yl)-3-(4-(trifluoromethoxy)phenyl)urea;
1-(4-Nitrophenyl)-3-(4,4-dimethylchroman-6-yl)thiourea;
1-(4,4-Dimethylchroman-6-yl)-3-(4-(trifluoromethyl)phenyl)thiourea;
1-(4,4-Dimethylchroman-6-yl)-3-(4-(trifluoromethoxy)phenyl)thiourea;
1-(4-Nitrophenyl)-3-(4,4-dimethylchroman-6-yl)urea;
(4,4-Dimethylchroman-6-yl)-3-[4-trifluoromethyl)phenyl]urea;
1-(4,4-Dimethylchroman-6-yl)-3-(4-(trifluoromethoxy)phenyl)urea;
1-(2,2-Diethyl-4,4-dimethylchroman-6-yl)-3-(4-nitrophenyl)thiourea;
1-(2,2-Diethyl-4,4-dimethylchroman-6-yl)-3-(4-nitrophenyl)urea;
1-(2,2-Diethyl-4,4-dimethylchroman-6-yl)-3-(4-(trifluoromethyl)phenyl)urea;
1-(4,4-Diethyl-2,2-dimethylchroman-6-yl)-3-(4-nitrophenyl)thiourea;
1-(4,4-Diethyl-2,2-dimethylchroman-6-yl)-3-(4-(trifluoromethyl)phenyl)thiourea;
1-(4,4-Diethyl-2,2-dimethylchroman-6-yl)-3-(4-nitrophenyl)urea;
1-(4,4-Diethyl-2,2-dimethylchroman-6-yl)-3-(4-(trifluoromethyl)phenyl)urea;
1-(4-Nitrophenyl)-3-(2,2,4,4-tetraethylchroman-6-yl)thiourea;
1-(4-Nitrophenyl)-3-(2,2,4,4-tetraethylchroman-6-yl)urea;
1-(2,2,4,4-Tetraethylchroman-6-yl)-3-(4-(trifluoromethyl)phenyl)urea;
1-(2,2,4,4-Tetraethylchroman-6-yl)-3-(4-(trifluoromethoxy)phenyl)urea;
1-(4,4-Dimethyl-1,2,3,4-tetrahydroquinolin-6-yl)-3-(4-nitrophenyl)urea;
1-(4,4-Dimethyl-1,2,3,4-tetrahydroquinolin-6-yl)-3-(4-nitrophenyl)thiourea;
1-(4,4-Dimethyl-1,2,3,4-tetrahydroquinolin-6-yl)-3-(4-(trifluoromethyl)phenyl)thiourea;
1-(4,4-Dimethyl-1,2,3,4-tetrahydroquinolin-6-yl)-3-(4-(trifluoromethoxy)phenyl)-thiourea;
1,1,4,4-Tetramethyl-6-(3-(4-nitrophenyl)ureido)-1,2,3,4-tetrahydroquinolin-1-ium iodide;
1-(4-Nitrophenyl)-3-(1,2,2,4,4-pentamethyl-3-oxo-1,2,3,4-tetrahydroquinolin-6-yl)urea;
1-(4-Nitrophenyl)-3-(1,2,2,4,4-pentamethyl-3-oxo-1,2,3,4-tetrahydroquinolin-6-yl)thiourea;
1-(1,2,2,4,4-Pentamethyl-3-oxo-1,2,3,4-tetrahydroquinolin-6-yl)-3-(4-(trifluoromethyl)-phenyl)urea;
1-(1,2,2,4,4-Pentamethyl-3-oxo-1,2,3,4-tetrahydroquinolin-6-yl)-3-(4-trifluoromethyl)-phenyl)thiourea;
1-(1,2,2,4,4-Pentamethyl-3-oxo-1,2,3,4-tetrahydroquinolin-6-yl)-3-(4-(trifluoromethoxy)-phenyl)urea;
1-(1,2,2,4,4-Pentamethyl-3-oxo-1,2,3,4-tetrahydroquinolin-6-yl)-3-(4-(trifluoromethoxy)-phenyl)thiourea;
1-(4-Aminophenyl)-3-(1,2,2,4,4-pentamethyl-3-oxo-1,2,3,4-tetrahydroquinolin-6-yl)urea;
3-(1,2,2,4,4-Pentamethyl-1,2,3,4-tetrahydroquinolin-6-yl)-1-(4-nitrophenyl)thiourea;
1-(3-Hydroxy-1,2,2,4,4-pentamethyl-1,2,3,4-tetrahydroquinolin-6-yl)-3-(4-nitrophenyl)-urea;
1-(3-Hydroxy-1,2,2,4,4-pentamethyl-1,2,3,4-tetrahydroquinolin-6-yl)-3-(4-nitrophenyl)-thiourea;
1-(3-Hydroxy-1,2,2,4,4-pentamethyl-1,2,3,4-tetrahydroquinolin-6-yl)-3-(4-(trifluoro-methyl)phenyl)urea;
1-(3-Hydroxy-1,2,2,4,4-pentamethyl-1,2,3,4-tetrahydroquinolin-6-yl)-3-(4-(trifluoro-methyl)phenyl)thiourea;
1-(3-Hydroxy-1,2,2,4,4-pentamethyl-1,2,3,4-tetrahydroquinolin-6-yl)-3-(4-(trifluoro-methoxy)phenyl)urea;
1-(3-Hydroxy-1,2,2,4,4-pentamethyl-1,2,3,4-tetrahydroquinolin-6-yl)-3-(4-(trifluoro-methoxy)phenyl)thiourea;
1-(4-Acetylphenyl)-3-(2,2,4,4-tetramethylthiochroman-6-yl)urea;
1-(2,2,4,4-Tetramethylthiochroman-6-yl)-3-(4-(trifluoromethyl)phenyl)urea;
1-(2,2,4,4-Tetramethylthiochroman-6-yl)-3-(4-(trifluoromethoxy)phenyl)urea;
1-(4-Cyanophenyl)-3-(2,2,4,4-tetramethylthiochroman-6-yl)urea;
1-(2-Methoxy-4-nitrophenyl)-3-(2,2,4,4-tetramethylthiochroman-6-yl)urea;
1-Phenyl-3-(2,2,4,4-tetramethylthiochroman-6-yl)thiourea;
1-(4-Methylphenyl)-3-(2,2,4,4-tetramethylthiochroman-6-yl)thiourea;

1-(5,6,7,8-Tetrahydronaphthalen-2-yl)-3-(2,2,4,4-tetramethylthiochroman-6-yl)thiourea;
4.3.4. 1-(4-Chlorophenyl)-3-(2,2,4,4-tetramethylthiochroman-6-yl)thiourea;
1-(2,2,4,4-Tetramethylthiochroman-6-yl)-3-(4-(trifluoromethyl)phenyl)thiourea;
1-(2,2,4,4-Tetramethylthiochroman-6-yl)-3-(4-(trifluoromethoxy)phenyl)thiourea;
4.3.7. 1-(3-Nitrophenyl)-3-(2,2,4,4-tetramethylthiochroman-6-yl)thiourea;
4.3.8. 1-(2,2,4,4-Tetramethylthiochroman-6-yl)-3-(2-(trifluoromethyl)phenyl)thiourea;
4-(3-(2,2,4,4-Tetramethylthiochroman-6-yl)thioureido)benzamide;
1-(4-Methoxyphenyl)-3-(2,2,4,4-tetramethylthiochroman-6-yl)thiourea;
1-(3-Methoxyphenyl)-3-(2,2,4,4-tetramethylthiochroman-6-yl)thiourea;
1-(4-Hydroxyphenyl)-3-(2,2,4,4-tetramethylthiochroman-6-yl)thiourea;
1-(3-Hydroxy-4-methoxyphenyl)-3-(2,2,4,4-tetramethylthiochroman-6-yl)thiourea;
1,3-Bis(2,2,4,4-Tetramethylthiochroman-6-yl)thiourea;
1-(2,2,4,4-Tetramethylthiochroman-6-yl)-3-(4-(trifluoromethyl)phenyl)urea;
1-(2,2,4,4-Tetramethylthiochroman-6-yl)-3-(4-(trifluoromethoxy)phenyl)urea;
1-(4-Cyanophenyl)-3-(2,2,4,4-tetramethylthiochroman-6-yl)urea;
1-(4-Chlorophenyl)-3-(2,2,4,4-tetramethylthiochroman-6-yl)thiourea;
1-(2,2,4,4-Tetramethylthiochroman-6-yl)-3-(4-(trifluoromethyl)phenyl)thiourea;
1-(2,2,4,4-Tetramethylthiochroman-6-yl)-3-(4-(trifluoromethoxy)phenyl)thiourea;
4-(3-(2,2,4,4-Tetramethylthiochroman-6-yl)thioureido)benzamide;
1-(4-Methoxyphenyl)-3-(2,2,4,4-tetramethylthiochroman-6-yl)thiourea;
1-(3-Methoxyphenyl)-3-(2,2,4,4-tetramethylthiochroman-6-yl)thiourea;
1-Benzyl-3-(2,2,4,4-tetramethylthiochroman-6-yl)thiourea;
1-Phenethyl-3-(2,2,4,4-tetramethylthiochroman-6-yl)thiourea;
1-(4-Chlorobenzyl)-3-(2,2,4,4-tetramethylthiochroman-6-yl)thiourea;
1-(4-Nitrobenzyl)-3-(2,2,4,4-tetramethylthiochroman-6-yl)thiourea;
1-(2,2,4,4-Tetramethylthiochroman-6-yl)-3-(4-(trifluoromethyl)benzyl)thiourea;
1-(4-Methoxybenzyl)-3-(2,2,4,4-tetramethylthiochroman-6-yl)thiourea;
1-(4-Hydroxybenzyl)-3-(2,2,4,4-tetramethylthiochroman-6-yl)thiourea;
2-Phenyl-N-(2,2,4,4-tetramethylthiochroman-6-yl)hydrazine-1-carbothioamide;
2-Benzoyl-N-(2,2,4,4-tetramethylthiochroman-6-yl)hydrazine-1-carbothioamide;
2-(4-Nitrobenzoyl)-N-(2,2,4,4-tetramethylthiochroman-6-yl)hydrazine-1-carbothioamide;
N-(2,2,4,4-Tetramethylthiochroman-6-yl)-2-(4-(trifluoromethoxy)benzoyl)hydrazine-1-carbothioamide;
2-(3,5-Bis(trifluoromethyl)benzoyl)-N-(2,2,4,4-tetramethylthiochroman-6-yl)hydrazine-1-carbothioamide;
4,4-Dimethylthiochroman-6-amine hydrochloride;
and salts, solvates and hydrates thereof.

In further aspects, the compound is:

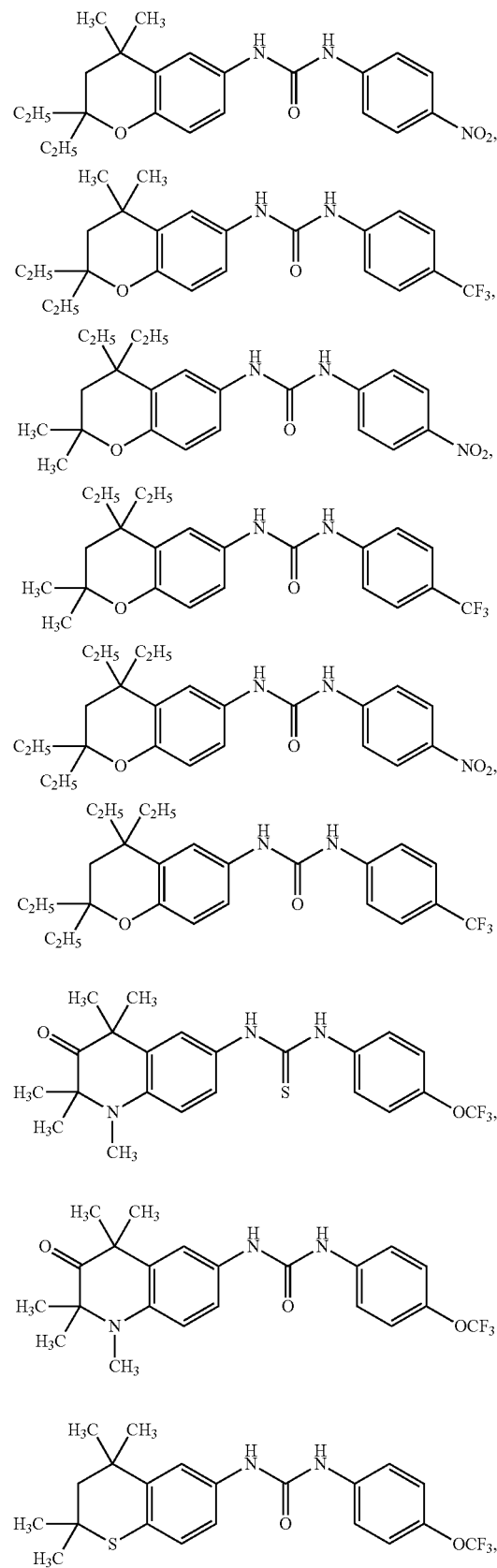

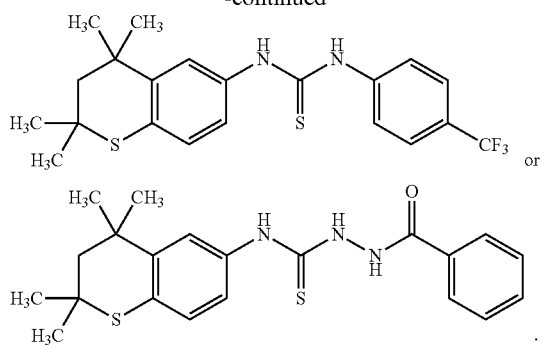

The disclosure also provides methods of treating cancer in a subject in need thereof, comprising administering to the subject a therapeutically effective amount of compound of Formula I

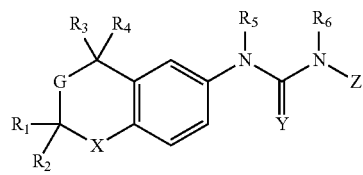

wherein,

R₁ and R₂ are optionally C1-C5 substituted alkyl;
R₃ and R₄ are optionally C1-C5 substituted alkyl;
G is CH₂, C=O or CHOH;
X is S, O, NR or N⁺(R)₂ where R is hydrogen or an optionally substituted C1-C5 alkyl;
R₅ and R₆ are hydrogen or optionally substituted C1-C5 alkyl;
Y is O or S; and
Z is an optionally substituted phenyl, optionally substituted phenylamino or optionally substituted benzylamide;

and salts, solvates and hydrates thereof, with the caveat that the compound is not SHetA2 with the formula

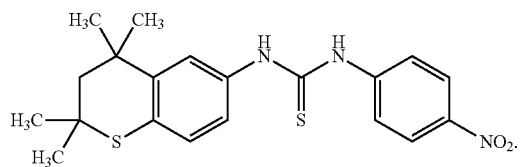 [SMILES: CC1(C)CC(C)(C)c2cc(NC(=S)Nc3ccc([N+](=O)[O-])cc3)ccc2S1]

In certain aspects, the compound is:

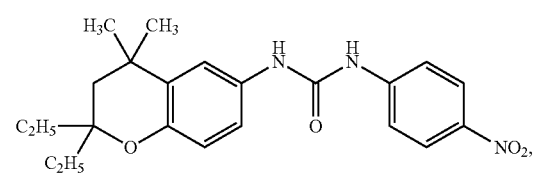

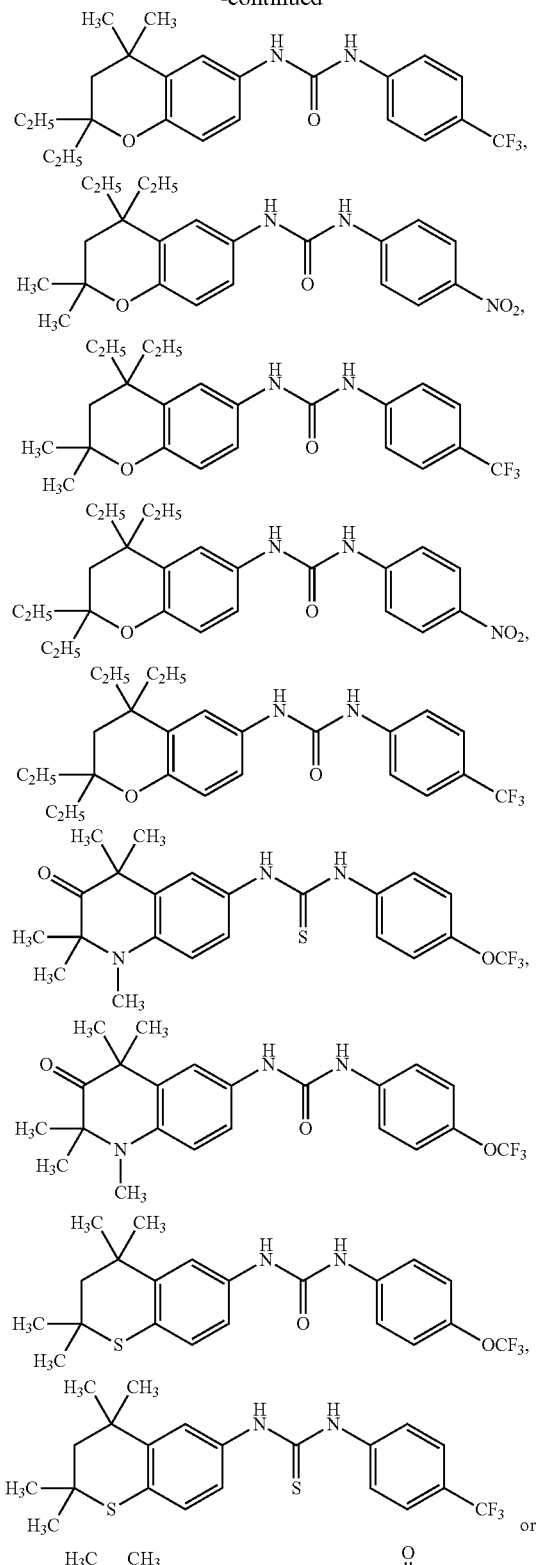

In further aspects, the cancer is ovarian cancer or small cell lung cancer.

The disclosure also provides a method of killing cancer cells, comprising contacting the cancer cells with an amount of a compound of Formula I

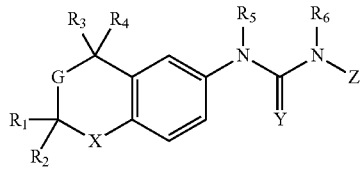

wherein, $R_1$ and $R_2$ are optionally C1-C5 substituted alkyl;

$R_3$ and $R_4$ are optionally C1-C5 substituted alkyl;

G is $CH_2$, C=O or CHOH;

X is S, O, NR or $N^+(R)_2$ where R is hydrogen or an optionally substituted C1-C5 alkyl;

$R_5$ and $R_6$ are hydrogen or optionally substituted C1-C5 alkyl;

Y is O or S; and

Z is an optionally substituted phenyl, optionally substituted phenylamino or optionally substituted benzylamide;

and salts, solvates and hydrates thereof, wherein the amount is sufficient to kill the cancer cells, and with the caveat that the compound is not SHetA2 with the formula

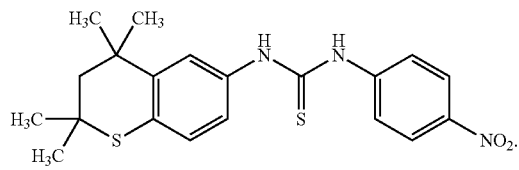 [SMILES: CC1(C)CC(C)(C)c2cc(NC(=S)Nc3ccc([N+](=O)[O-])cc3)ccc2S1]

In some aspects, the compound is:

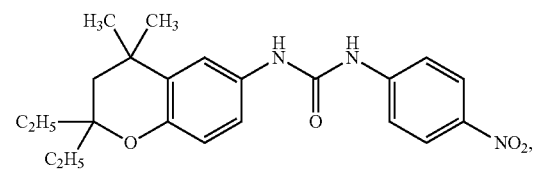

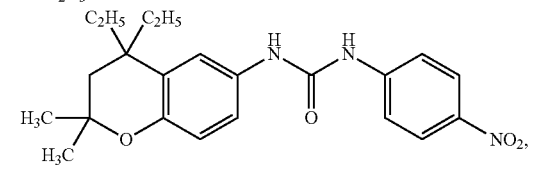

-continued

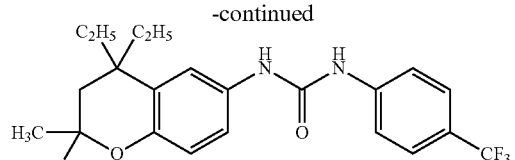

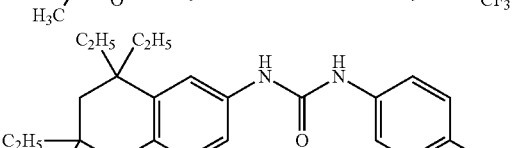

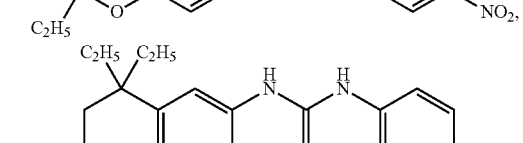

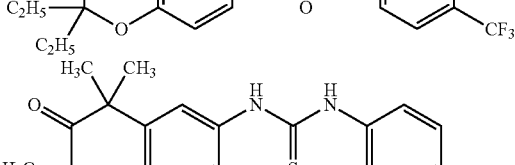

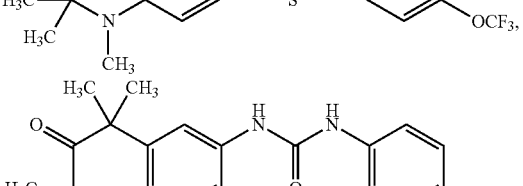

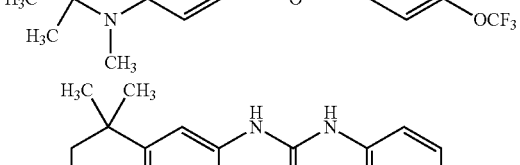

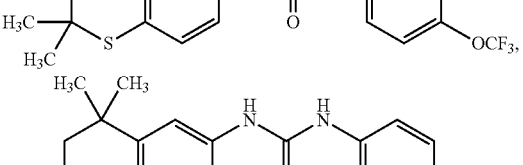

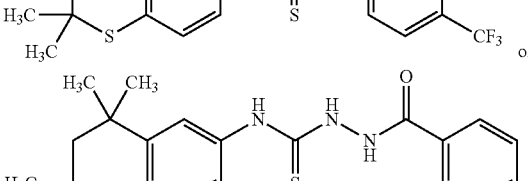

In certain aspects, the cancer cells are ovarian cancer cells.

The foregoing has outlined in broad terms some of the more important features of the invention disclosed herein so that the detailed description that follows may be more clearly understood, and so that the contribution of the instant inventors to the art may be better appreciated. The instant invention is not to be limited in its application to the details of the construction and to the arrangements of the components set forth in the following description or illustrated in the drawings. Rather, the invention is capable of other embodiments and of being practiced and carried out in various other ways not specifically enumerated herein.

Finally, it should be understood that the phraseology and terminology employed herein are for the purpose of description and should not be regarded as limiting, unless the specification specifically so limits the invention.

DETAILED DESCRIPTION

While this invention is susceptible of embodiment in many different forms, there is shown in the drawings, and will herein be described hereinafter in detail, some specific embodiments of the instant invention. It should be understood, however, that the present disclosure is to be considered an exemplification of the principles of the invention and is not intended to limit the invention to the specific embodiments or algorithms so described.

The new heteroarotinoids disclosed herein comprise a chroman-, tetrahydroquinoline- or thiochroman-fused ring system bonded to an aryl group via a urea or thiourea linker (Formula I). It is well known that urea derivatives are easily handled by the body and exhibit low toxicity. Insertion of a chroman (oxygen-atom at position-1) or tetrahydroquinoline (nitrogen atom at position-1) is a new unique structural change in this family of heterocycles. In addition, compounds with specific substituents [e.g. $NO_2$, $CF_3$, $OCF_3$] bonded to a single phenyl ring attached to the linker displayed major cancer inhibitory activity. The presence of geminal diethyl groups at C-1 and C-4 in the tetrahydroquinoline unit appeared to contribute to maximum activity.

The disclosed heterocycles exhibit a range of abilities to inhibit the growth of human lung and A2780 ovarian cancer cells. In fact, several of the disclosed compounds outperformed SHetA2 in the inhibition of A2780 cells, and some exhibited very high potency. For example, several of the best compounds achieved 92-95% efficacy (measured in growth inhibition) and 2 μM $IC_{50}$, i.e. better than SHetA2, which has about 84% efficacy and 3 μM $IC_{50}$. The compounds are able to inhibit growth of all 60 cancer cell lines available from the National Cancer Institute yet these compounds do not cause toxicity or skin irritation in normal tissues, and do not cause birth defects in animal studies. Without being bound by theory, it is believed that the linkers render the new compounds more flexible for docking to the protein mortalin, which is believed to be the target receptor and is believed to be involved in the progress of a cell becoming cancerous. In binding to mortalin, it is believed that the compounds induce normal differentiation or apoptosis of the cancerous cells.

A generic structure of the heteroarotinoids is shown in Formula 1 below.

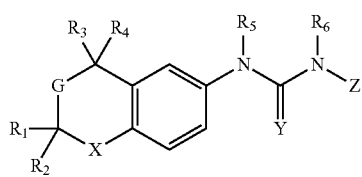

Formula I wherein,
$R_1$ and $R_2$ are optionally C1-C5 substituted alkyl;
$R_3$ and $R_4$ are optionally C1-C5 substituted alkyl;
G is $CH_2$, C=O or CHOH;
X is S, O, NR or $N^+(R)_2$ where R is hydrogen or an optionally substituted C1-C5 alkyl;

$R_5$ and $R_6$ are hydrogen or optionally substituted C1-C5 alkyl;
Y is O or S; and
Z is an optionally substituted phenyl, optionally substituted phenylamino or optionally substituted benzylamide;
and salts, solvates and hydrates thereof,
with the caveat that the compound is not SHetA2 with the formula

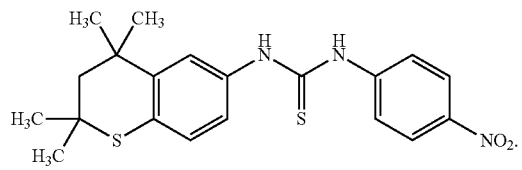 [SMILES: CC1(C)CC(C)(C)c2cc(NC(=S)Nc3ccc([N+](=O)[O-])cc3)ccc2S1]

The salts may be a pharmaceutically acceptable salts. Stereoisomers of the compounds are also encompassed.

In general, the compounds can be divided into three categories: chroman-containing heteroarotinoids, tetrahydroquinoline-containing heteroarotinoids and thiochroman-containing heteroarotinoids, exemplary formulations of which are:

Choman-Containing Heretoarotinoids

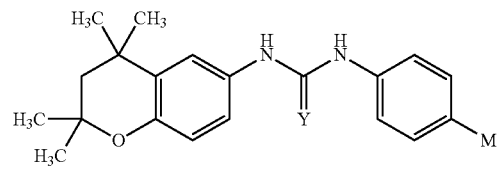

2-Me-4-Me Series
Y = S or O
M = $NO_2$, $CO_2Et$, $CF_3$, CN, $SO_2NH_2$ or $OCF_3$

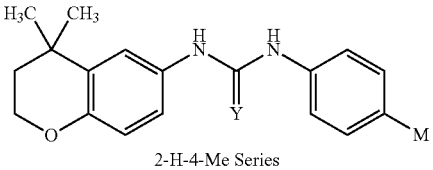

2-H-4-Me Series
Y = S or O
M = $NO_2$, $CF_3$ or $OCF_3$

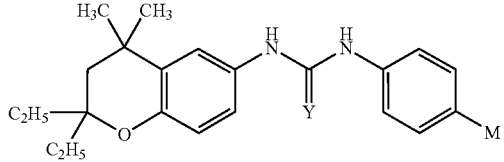

2-Et-4-Me Series
Y = S or O
M = $NO_2$ or $OCF_3$

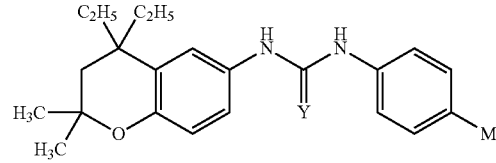

2-Me-4-Et Series
Y = S or O
M = $NO_2$ or $CF_3$

17
-continued

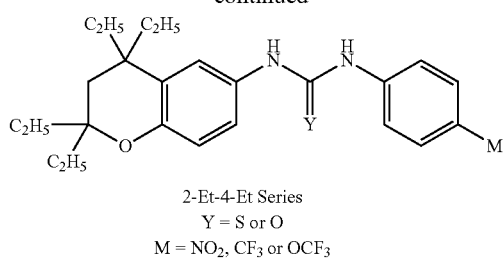

2-Et-4-Et Series
Y = S or O
M = NO₂, CF₃ or OCF₃

Tetrahydroquinoline-Containing Heretoarotinoids

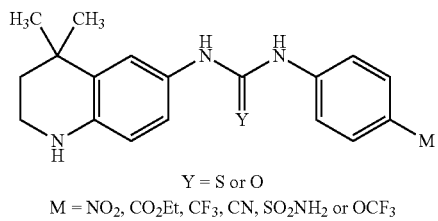

Y = S or O
M = NO₂, CO₂Et, CF₃, CN, SO₂NH₂ or OCF₃

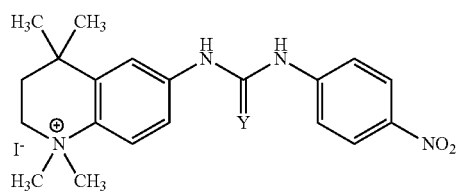

Y = S or O
M = NO₂, CO₂Et, CF₃, CN, SO₂NH₂ or OCF₃

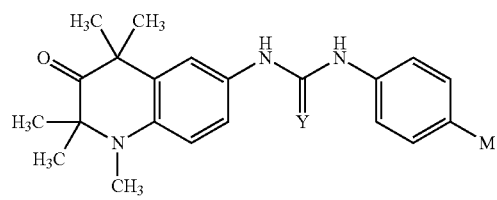

Y = S or O
M = NO₂, CO₂Et, CF₃, CN, SO₂NH₂ or OCF₃

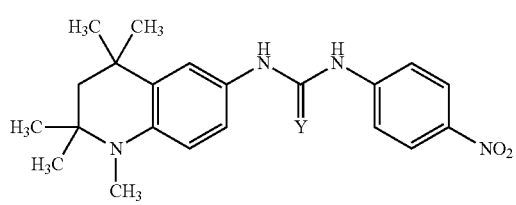

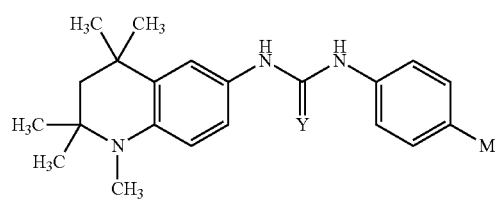

Y = S or O
M = NO₂, CO₂Et, CF₃, CN, SO₂NH₂ or OCF₃

18
-continued

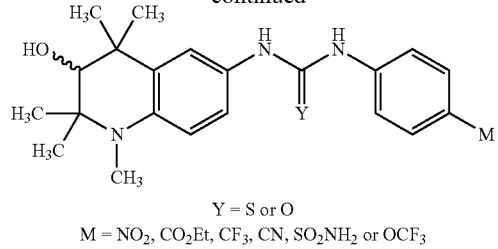

Y = S or O
M = NO₂, CO₂Et, CF₃, CN, SO₂NH₂ or OCF₃

Tetrahydrothiochroman-Containing Heretoarotinoids

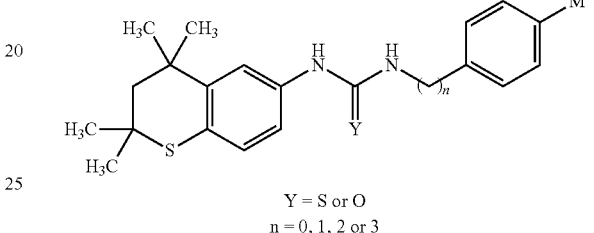

Y = S or O
n = 0, 1, 2 or 3
M = H, OH, NO₂, CO₂Et, CF₃, OCH₃, C(O)NH₂, CN, SO₂NH₂ or OCF₃

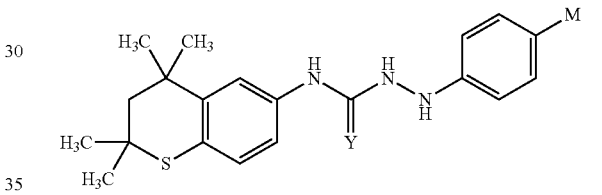

Y = S or O
M = H, OH, NO₂, CO₂Et, CF₃, OCH₃, C(O)NH₂, CN, SO₂NH₂ or OCF₃

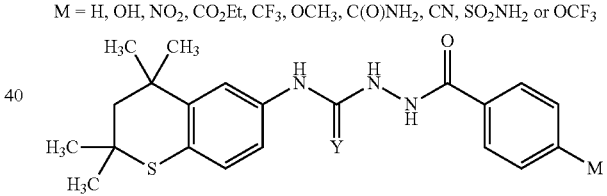

Y = S or O
M = H, OH, NO₂, CO₂Et, CF₃, OCH₃, C(O)NH₂, CN, SO₂NH₂ or OCF₃

As used herein, "a compound of the invention" includes all salts, solvates, complexes, polymorphs, radiolabeled derivatives, tautomers, stereoisomers and optical isomers of the compounds of Formula I.

The term "solvate" as used herein refers to an aggregate that comprises one or more molecules of a compound of the disclosure with one or more molecules of solvent. Examples of solvents that form solvates include, but are not limited to, water, isopropanol, ethanol, methanol, DMSO, ethyl acetate, acetic acid, and ethanolamine. The term "hydrate" refers to the aggregate or complex where the solvent molecule is water. The solvent may be an inorganic solvent such as for example water in which case the solvate may be a hydrate. Alternatively, the solvent may be an organic solvent, such as ethanol. Thus, the compounds of the present disclosure may exist as a hydrate, including a monohydrate, dihydrate, hemihydrate, sesquihydrate, trihydrate, tetrahydrate or the like, as well as the corresponding solvated forms. The compound of the disclosure may be true solvates, while in other cases, the compound of the disclosure may merely retain adventitious water or be a mixture of water plus some adventitious solvent.

Compositions/Pharmaceutical Compositions

Compositions, which may be pharmaceutical compositions, comprising one or more of the compounds disclosed herein as provided. Such compositions generally comprise at least one of the disclosed compounds, i.e., one or more than one (a plurality) of different compounds (e.g. 2 or more such as 2, 3, 4, 5, 6, 7, 8, 9, 10 or more) may be included in a single formulation. Pharmaceutical compositions generally include one or more substantially purified compounds as described herein, typically prepared using pharmaceutically acceptable excipients. As used herein, the term "pharmaceutically acceptable" refers to those compounds, materials, compositions, and dosage forms which are, within the scope of sound medical judgment, suitable for use in contact with the tissues of human beings and animals without excessive toxicity, irritation, or other problem or complication, commensurate with a reasonable benefit/risk ratio.

As used herein, "pharmaceutically acceptable excipients" includes all diluents, carriers binders, glidants and other components of pharmaceutical formulations with which the compound of the invention is administered. A pharmacologically suitable or acceptable (physiologically compatible) carrier may be, for example, aqueous or oil-based.

In some aspects, such compositions are prepared as liquid solutions or suspensions, or as solid forms such as tablets, pills, powders and the like. Solid forms suitable for solution in, or suspension in, liquids prior to administration are also contemplated (e.g. lyophilized forms of the compounds), as are emulsified preparations. In some aspects, the liquid formulations are aqueous or oil-based suspensions or solutions. In some aspects, the active ingredients are mixed with excipients which are pharmaceutically acceptable and compatible with the active ingredients, e.g. pharmaceutically acceptable salts. Suitable excipients include, for example, water, saline, dextrose, glycerol, ethanol and the like, or combinations thereof. In addition, the composition may contain minor amounts of auxiliary substances such as wetting or emulsifying agents, pH buffering agents, preservatives, and the like. If it is desired to administer an oral form of the composition, various thickeners, flavorings, diluents, emulsifiers, dispersing aids or binders and the like are added. The composition of the present invention may contain any such additional ingredients so as to provide the composition in a form suitable for administration. The final amount of compound in the formulations varies, but is generally from about 1-99%. Still other suitable formulations for use in the present invention are found, for example in Remington's Pharmaceutical Sciences, 22nd ed. (2012; eds. Allen, Adejarem Desselle and Felton).

Some examples of materials which can serve as pharmaceutically acceptable carriers include, but are not limited to, ion exchangers, alumina, aluminum stearate, lecithin, serum proteins (such as human serum albumin), buffer substances (such as twin 80, phosphates, glycine, sorbic acid, or potassium sorbate), partial glyceride mixtures of saturated vegetable fatty acids, water, salts or electrolytes (such as protamine sulfate, disodium hydrogen phosphate, potassium hydrogen phosphate, sodium chloride, or zinc salts), colloidal silica, magnesium trisilicate, polyvinyl pyrrolidone, polyacrylates, waxes, polyethylene-polyoxypropylene-block polymers, methylcellulose, hydroxypropyl methylcellulose, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

"Pharmaceutically acceptable salts" refers to the relatively non-toxic, inorganic and organic acid addition salts, and base addition salts, of compounds of the present invention. These: salts can be prepared in situ during the final isolation and purification of the compounds. In particular, acid addition salts can be prepared by separately reacting the purified compound in its free base form with a suitable organic or inorganic acid and isolating the salt thus formed. Exemplary acid addition salts include the hydrobromide, hydrochloride, sulfate, bisulfate, phosphate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate, sulfamates, malonates, salicylates, propionates, methylene-bis-.beta.-hydroxynaphthoates, gentisates, isethionates, di-p-toluoyltartrates, methanesulfonates, ethanesulfonates, benzenesulfonates, p-toluenesulfonates, cyclohexylsulfamates and laurylsulfonate salts, and the like. See, for example S. M. Berge, et al., "Pharmaceutical Salts," J. Pharm. Sci., 66, 1-19 (1977) which is incorporated herein by reference. Base addition salts can also be prepared by separately reacting the purified compound in its acid form with a suitable organic or inorganic base and isolating the salt thus formed. Base addition salts include pharmaceutically acceptable metal and amine salts. Suitable metal salts include the sodium, potassium, calcium, barium, zinc, magnesium, and aluminum salts. The sodium and potassium salts are preferred. Suitable inorganic base addition salts are prepared from metal bases which include sodium hydride, sodium hydroxide, potassium hydroxide, calcium hydroxide, aluminum hydroxide, lithium hydroxide, magnesium hydroxide, zinc hydroxide and the like. Suitable amine base addition salts are prepared from amines which have sufficient basicity to form a stable salt, and preferably include those amines which are frequently used in medicinal chemistry because of their low toxicity and acceptability for medical use. ammonia, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)-aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, e.g., lysine and arginine, and dicyclohexylamine, and the like.

Methods

The present disclosure encompasses methods of treating cancer, in a subject or patient in need thereof, using one or more of the compounds disclosed herein. Generally, the methods involve administering to the subject one or more of the disclosed compounds (generally present in a pharmaceutically acceptable carrier), in an amount sufficient to treat the cancer, e.g. by killing cancer (e.g. tumor) cells which come into contact with the administered compound within the body of the subject. Methods of administration are discussed in detail below. In some cases, treatment with the compounds will effect a cure of the cancer, i.e. all tumor cells will be killed and/or eradicated from the body of the subject. However, those of skill in the art will recognize that much benefit may be derived even if a complete cure is not attained. For example, the growth of a tumor may be stopped or slowed, the progression of the cancer may be halted or slowed, the life of the cancer patient may be extended or improved, one or more symptoms of the cancer may be ameliorated, etc.

The present disclosure also encompasses methods of killing cancer cells with the compounds disclosed herein. The cancer cells may be in vivo or in vitro. Generally, the methods involve contacting the cancer cells with one or more of the disclosed compounds, in an amount sufficient to kill the cancer cell. Without being bound by theory, the mechanism of killing may be via apoptosis of the cancer cell.

Administration

The compounds may be administered in vivo by any suitable route including but not limited to: orally; by injection (e.g. intravenous, intraperitoneal, intramuscular, subcutaneous, intra-aural, intraarticular, intramammary, intratumorally and the like); by absorption through epithelial or mucocutaneous linings (e.g., nasal, oral, vaginal, rectal, gastrointestinal mucosa, and the like); etc. In preferred embodiments, the mode of administration is oral or by injection.

In addition, the compositions may be administered in conjunction with other treatment modalities such as: other anticancer agents, pain medications, substances that boost the immune system, various chemotherapeutic agents, anti-nausea medications, appetite enhancers, antibiotic agents, and the like. The compounds may also be used in cancer treatment protocols that also include e.g. surgery, radiation therapy, etc.

The amount of a compound that is administered to an individual (who is usually a mammal, and may be a human) will vary based on several factors, as will be understood by those of skill in the art. For example, the dose and frequency of administration may vary according to the gender, age, weight, general physical condition, ethnic background, etc. of the individual, as well as whether or not the individual has other diseases or conditions that might impinge on the treatment. Generally, the dose for a therapeutically effective amount will be in the range of from about 0.01 to about 100 mg/kg of body weight, such as about 0.1, 0.5, 1.0, 5.0, 10, 15, 20, 25, 30, 35, 40, 45, 50, 55, 60, 65, 70, 75, 80, 85, 90, 95 or 100 mg/kg of body weight.

As used herein, the term "effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of one or more symptoms a disease, disorder, or side effect, or a decrease in the rate of advancement of a disease or disorder. The term also includes within its scope amounts effective to enhance normal physiological function. A therapeutically effective amount is generally an amount that ameliorates, lessens or improves at least one symptom of the disease/condition that is being treated, and this amount may also eradicate all symptoms of the disease/condition, i.e. it may cure the subject of the disease/condition. In particular, the subject may become entirely cancer free and/or the life of the subject may be extended.

While the subjects that are treated are often humans, veterinary applications of the treatment methods are also encompassed, especially for companion pets such as dogs, cats, etc.

Pharmaceutical compositions may be presented in unit dose forms containing a predetermined amount of active ingredient per unit dose. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient, vehicle or carrier. Typical unit dosage forms include prefilled, premeasured ampules or syringes of the liquid compositions or pills, tablets, capsules or the like in the case of solid compositions.

Preferred unit dosage compositions are those containing a daily dose or sub-dose, or an appropriate fraction thereof, of an active ingredient. Such unit doses may therefore be administered once or more than once a day. Such pharmaceutical compositions may be prepared by any of the methods well known in the pharmacy art.

Types and Stages of Cancer that are Treated

The compounds disclosed herein can be used to treat any type of proliferative diseases, i.e. a disease caused by or associated with over-proliferation, such as a cancer and/or pre-cancerous syndromes, including metastatic cancers such as metastatic tumors. Examples of types of cancer that can be treated include but are not limited to: Acute Lymphoblastic Leukemia (ALL), Acute Myeloid Leukemia (AML), Adrenocortical Carcinoma, AIDS-Related Cancers, Kaposi Sarcoma, AIDS-Related Lymphoma, Primary CNS Lymphoma, Anal Cancer, Appendix Cancer, Astrocytomas, Atypical Teratoid/Rhabdoid Tumor, Central Nervous System, Basal Cell Carcinoma, Bile Duct Cancer, Bladder Cancer, Bone Cancer, Ewing Sarcoma Family of Tumors, Osteosarcoma and Malignant Fibrous Histiocytoma, Brain Stem Glioma, Brain Tumor (e.g. Astrocytomas, Brain and Spinal Cord Tumors, Brain Stem Glioma, Central Nervous System Atypical Teratoid/Rhabdoid Tumor, Central Nervous System Embryonal Tumors, Central Nervous System Germ Cell Tumors, Craniopharyngioma, Ependymoma), Breast Cancer, Bronchial Tumors, Burkitt Lymphoma, Carcinoid Tumor, Gastrointestinal, Cardiac (Heart) Tumors, Central Nervous System (e.g. Atypical Teratoid/Rhabdoid Tumors, Embryonal Tumors, Germ Cell Tumors, Lymphomas), Cervical Cancer, Childhood Cancers, Cholangiocarcinoma, Chordoma, Chronic Lymphocytic Leukemia (CLL), Chronic Myelogenous Leukemia (CML), Chronic Myeloproliferative Neoplasms, Colon Cancer, Colorectal Cancer, Craniopharyngioma, Cutaneous T-Cell Lymphoma, Ductal Carcinoma In Situ (DCIS), Embryonal Tumors, Endometrial Cancer, Ependymoma, Esophageal Cancer, Esthesioneuroblastoma, Ewing Sarcoma, Extracranial Germ Cell Tumors, Extragonadal Germ Cell Tumors, Eye Cancer, Intraocular Melanoma, Retinoblastoma, Fallopian Tube Cancer, Fibrous Histiocytoma of Bone, Malignant, and Osteosarcoma, Gallbladder Cancer, Gastric (Stomach) Cancer, Gastrointestinal Carcinoid Tumor, Gastrointestinal Stromal Tumors (GIST), Hairy Cell Leukemia, Head and Neck Cancer, Heart Cancer, Hepatocellular (Liver) Cancer, Histiocytosis, Langerhans Cell, Hodgkin Lymphoma, Hypopharyngeal Cancer, Intraocular Melanoma, Islet Cell Tumors, Pancreatic Neuroendocrine Tumors, Kaposi Sarcoma, Kidney (Renal Cell, Wilms Tumor and Other Childhood Kidney Tumors), Langerhans Cell Histiocytosis, Laryngeal Cancer, Leukemia (Acute Lymphoblastic (ALL), Acute Myeloid (AML), Chronic Lymphocytic (CLL), Chronic Myelogenous (CML), Hairy Cell), Lip and Oral Cavity Cancer, Liver Cancer (Primary), Lung Cancer (Non-Small Cell, Small Cell), Lymphoma, Macroglobulinemia, Waldenström—see Non-Hodgkin Lymphoma, Malignant Fibrous Histiocytoma of Bone and Osteosarcoma, Melanoma, Intraocular (Eye), Merkel Cell Carcinoma, Mesothelioma, Malignant, Metastatic Squamous Neck Cancer with Occult Primary Mouth Cancer, Multiple Endocrine Neoplasia Syndromes, Multiple Myeloma/Plasma Cell Neoplasm, Mycosis Fungoides, Myelodysplastic Syndromes, Myelodysplastic/Myeloproliferative Neoplasms, Myelogenous Leukemia, Chronic (CIVIL), Myeloid Leukemia, Acute (AML), Myeloma, Multiple, Myeloproliferative Neoplasms, Chronic, Nasal Cavity and Paranasal Sinus Cancer, Nasopharyngeal Cancer, Neuroblastoma, Non-Hodgkin Lymphoma, Oral Cancer, Oral Cavity Cancer, Lip and Oropharyngeal Cancer, Osteosarcoma and Malignant Fibrous Histiocytoma of Bone, Ovarian Cancer, Epithelial, Germ Cell Tumor, Low Malignant Potential Tumor, Pancreatic Cancer, Pancreatic Neuroendocrine Tumors (Islet Cell Tumors), Papillomatosis, Paraganglioma, Paranasal Sinus and Nasal Cavity Cancer, Parathyroid Cancer, Penile Cancer, Pharyngeal Cancer, Pheochromocytoma, Pituitary Tumor, Plasma Cell Neoplasm/Multiple Myeloma, Pleuropulmonary Blastoma, Primary Central Nervous System (CNS) Lymphoma, Primary Peritoneal Cancer, Prostate Cancer, Rectal Cancer, Renal Cell (Kidney) Cancer, Renal Pelvis and Ureter, Transitional Cell Cancer, Retinoblastoma, Rhabdomyosarcoma, Salivary Gland Cancer, Sarcoma (Ewing, Kaposi, Osteosarcoma, Rhabdomyosarcoma, Soft Tissue, Uterine), Sézary Syndrome, Skin Cancer, Small Intestine Cancer, Squamous Cell Carcinoma, Squamous Neck Cancer with Occult Primary, Metastatic Stomach (Gastric) Cancer, T-Cell Lymphoma, Cutaneous, Testicular Cancer, Throat Cancer, Thymoma and Thymic Carcinoma, Thyroid Cancer, Ureter and Renal Pelvis Cancer, Transitional Cell Cancer, Urethral Cancer, Uterine Cancer, Vaginal Cancer, Vulvar Cancer, and Wilms Tumor.

The cancer may be at any stage. Current practice is to assign a number from I to IV to a cancer, with I being an isolated cancer and IV being a cancer which has spread to the limit of what the assessment measures. The stage generally takes into account the size of a tumor, whether it has invaded adjacent organs, how many regional (nearby) lymph nodes it has spread to (if any), and whether it has appeared in more distant locations (metastasized).

In some aspects, the cancer is ovarian cancer (OC), such as advanced stage OC (e.g. stage II, III or IV). In other aspects, one or more of the compounds described herein is/are used to treat cancer that is refractory to other cancer treatments (i.e. does not respond to treatment with a particular agent or combination of agents), and/or a cancer that has become resistant to other treatments (e.g. the cancer responded when treatment was initiated but stops responding, recurs, etc.) It is highly advantageous to have available a plurality of different compounds as described herein, for use, together or sequentially, to treat cancers.

The present compounds can be administered in conjunction with (e.g. at the same time as, or coordinated with) other cancer treatments. For example, a subject who is treated as described herein may also receive or undergo, or may have already received or undergone, one or more of radiation therapy, resection surgery, administration of other chemotherapy agents, etc. Other chemotherapy agents are known in the art and include those disclosed, for example, in issued U.S. Pat. No. 10,364,266, the complete contents of which is herein incorporated by reference.

The compounds may also be used in method of inducing normal differentiation and/or apoptosis of cancer cells (e.g. tumor cells). Apoptosis results in the death or killing of the cancer cells. Generally, such methods include a step of contacting the cancer cells with an amount of the compound of Formula I, the amount being sufficient to induce one or both of normal differentiation and/or apoptosis of cancer cells. The cancer cells may be in vitro (e.g. in an experimental laboratory setting) or in vivo (e.g. present in the body of a subject with cancer, such as present in a tumor).

Synthesis of Compounds

Schemes 1-3 below provide an overview of the synthetic schemes used to synthesize the compounds described herein. Details of each type of synthesis are provided in Example 1.

Scheme 1. Syntheses of chroman systems.

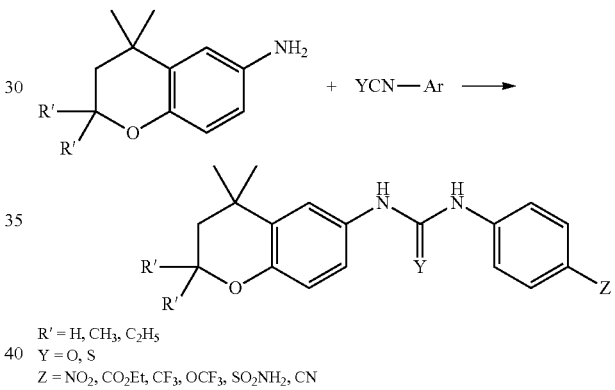

R' = H, CH₃, C₂H₅
Y = O, S
Z = NO₂, CO₂Et, CF₃, OCF₃, SO₂NH₂, CN

Scheme 2. Syntheses of selected substituted tetrahydroquinolines.

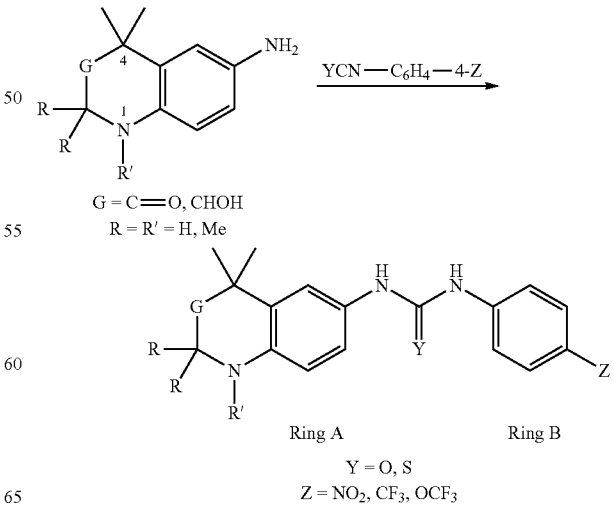

G = C═O, CHOH
R = R' = H, Me

Ring A          Ring B
Y = O, S
Z = NO₂, CF₃, OCF₃

Scheme 3. Syntheses of thiochroman systems.

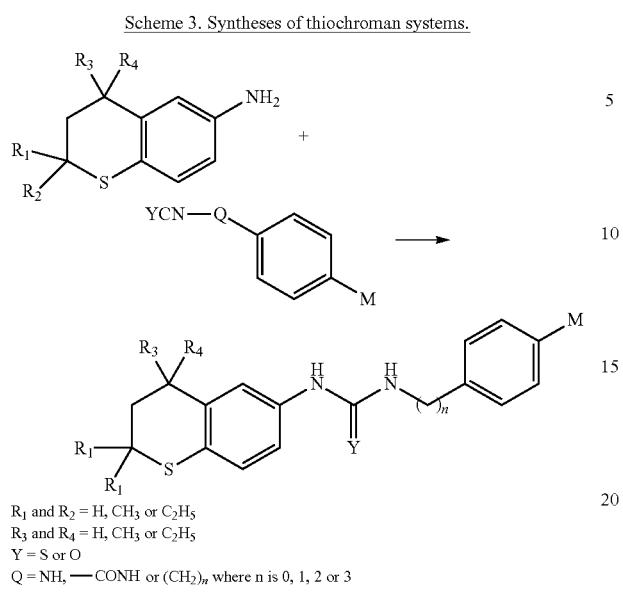

R₁ and R₂ = H, CH₃ or C₂H₅
R₃ and R₄ = H, CH₃ or C₂H₅
Y = S or O
Q = NH, —CONH or (CH₂)ₙ where n is 0, 1, 2 or 3
M = H, OH, NO₂, CO₂Et, CF₃, OCH₃, C(O)NH₂, CN, SO₂NH₂ or OCF₃

The present invention will be further understood with reference to the following, non-limiting experimental examples.

EXAMPLES

Example 1. Overview

This Example provides an overview of the steps and mechanisms involved in the reactions to generate the compounds, illustrated in Schemes 4-15.

General procedure to obtain members of 2 and 3; Scheme 4. Conversion of phenol (14) to phenyl 3,3-dimethylacryate 15 and then to 16 followed normal procedures. Known 16 was treated with a small excess of methyllithium as shown to give 17. The remaining sequence of 17→18→19/20→21→2 and 3 followed, with 2 and 3 being formed in good yields. The mixture of 19/20 could not be separated and thus was reduced to the amines from which 21 was isolated and purified. All products were solids with sharp melting points and gave the expected analytical data from IR, NMR, and elemental analyses.

Scheme 4. Synthesis of chroman analogs 2 and 3 (2-Me-4-Me Series).

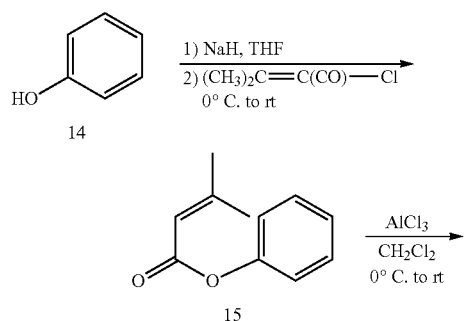

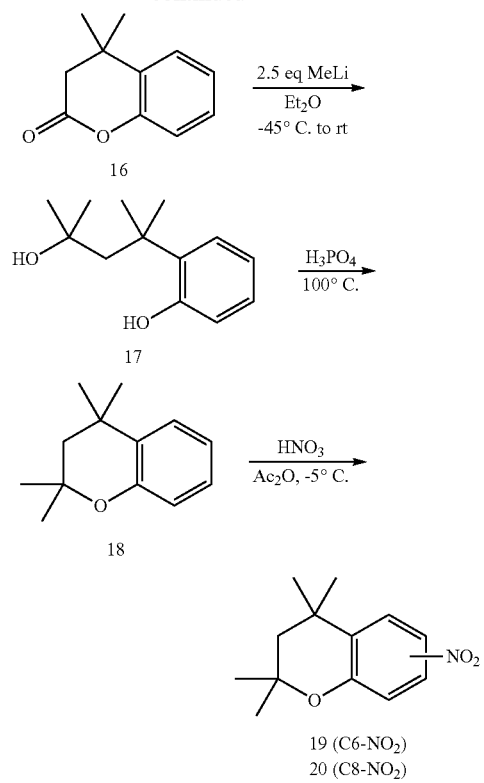

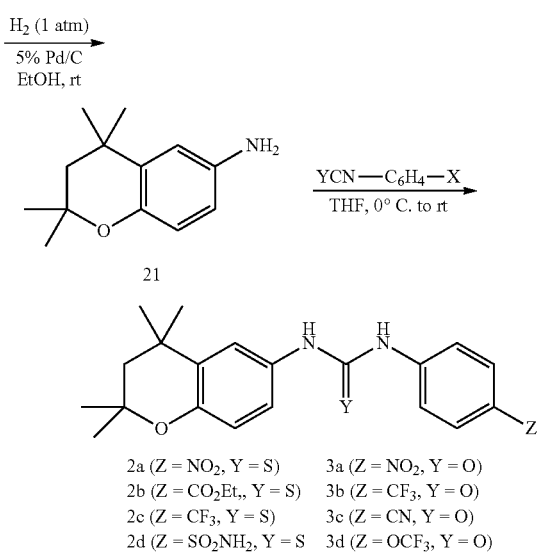

2a (Z = NO₂, Y = S)    3a (Z = NO₂, Y = O)
2b (Z = CO₂Et,, Y = S)  3b (Z = CF₃, Y = O)
2c (Z = CF₃, Y = S)    3c (Z = CN, Y = O)
2d (Z = SO₂NH₂, Y = S)  3d (Z = OCF₃, Y = O)

Members of 4 and 5 in Scheme 5 were also obtained by similar methodology. Utilizing 16 as starting material, the remaining steps are common and known by those skilled in the art, but not as applied herein. The nitration step gave two isomers 24/25 which could not be separated, but reducing the nitro group to the amino group gave two isomers (26, 27) that were separable. The reducing mixture of Fe/NH₄Cl converted 24 and 25 to 26 and 27 in good yields. Isolation of 26 followed by treatment with a small excess of the corresponding isocyanate or isothiocyanate gave members of 4 and 5 as solids with sharp melting points and the expected IR and NMR analytical data along with elemental analysis.

Scheme 5. Synthesis of chroman analogs 4 and 5 (2-H-4-Me Series).

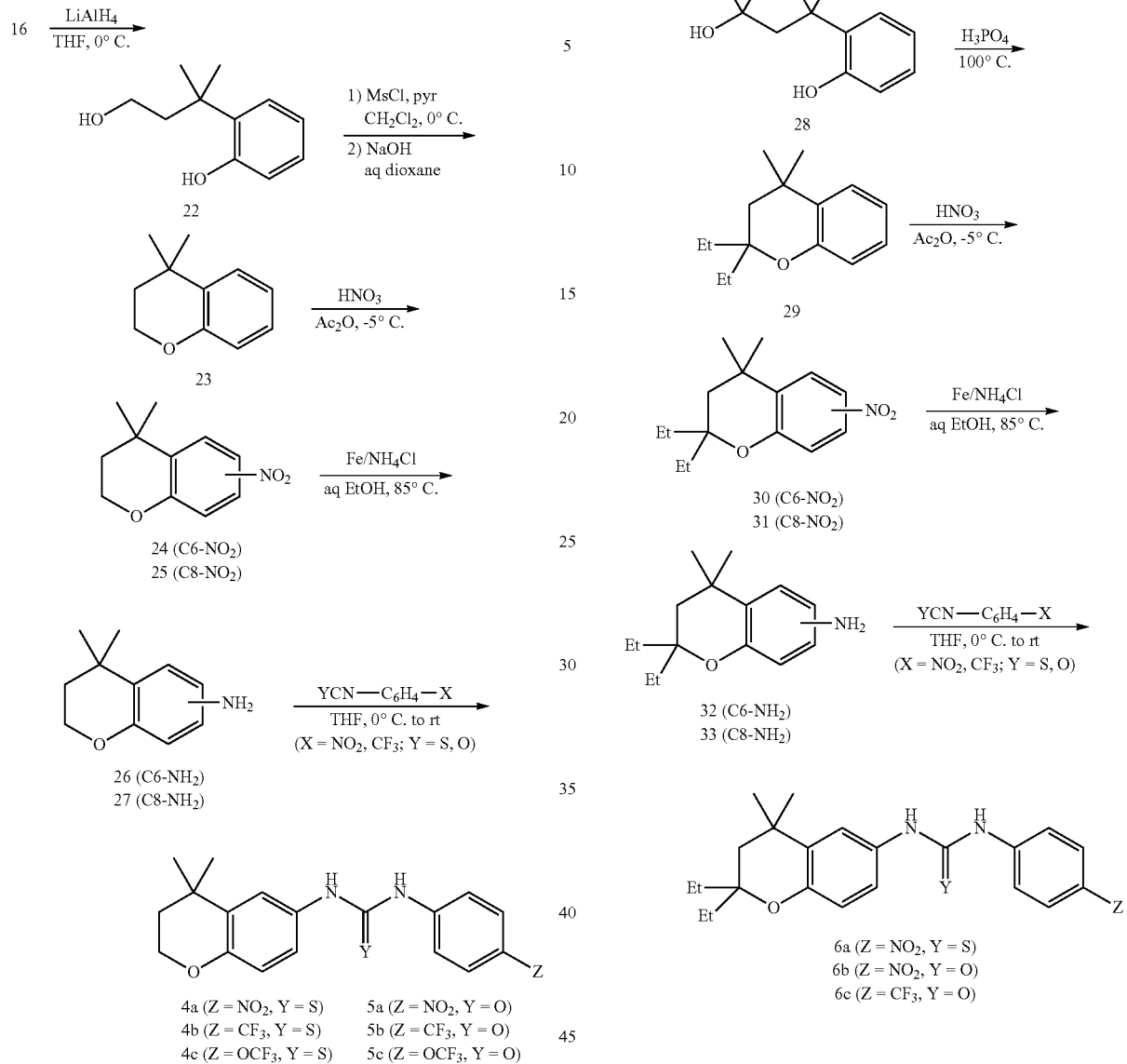

Schemes 6 and 7 led to 6 and 7, respectively, via similar transformations as above. In Scheme 6, a major change is the use of ethylmagnesium bromide to introduce ethyl groups at C-2. The other steps are similar to those illustrated previously. In Scheme 7, the required introduction of the geminal diethyl group at C-4 necessitated the acyl step to form 34 from phenol prior to closing of the ring to generate 35. The remaining steps are similar to those given to produce 2 and 3 and yielded members of 7. Members of 6 and 7 were solids, had sharp melting points, and provided the expected IR, NMR, and elemental analysis data for structural confirmation.

Scheme 6. Synthesis of chroman analgos 6 (2-Et-4-Me Series)

Scheme 7. Synthesis of chroman analogues 7 (2-Me-4-Et Series)

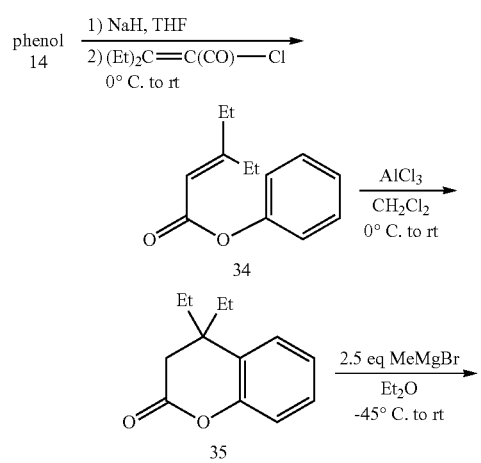

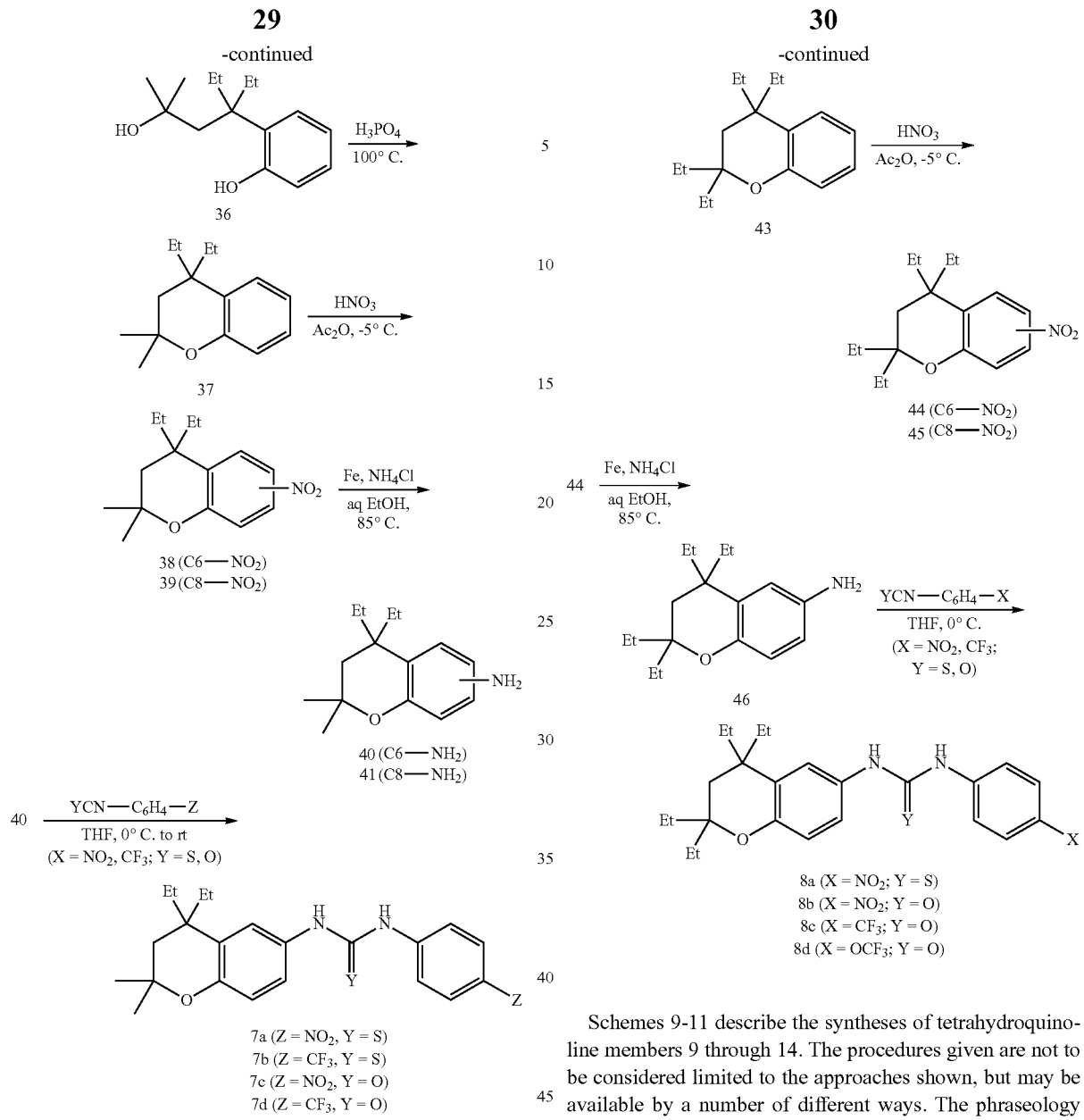

Scheme 8 required the starting material 35 which allowed the introduction of two sets of geminal diethyl groups at C-2 and C-4 as illustrated. Again the remaining transformations paralleled those previously described for 2 and 3 and led to members of 8. Final products 8 in Scheme 8 were solids with sharp melting points. To further confirm the structures, the products were purified by chromatography, and all products were identified by IR, NMR, and elemental analyses.

Schemes 9-11 describe the syntheses of tetrahydroquinoline members 9 through 14. The procedures given are not to be considered limited to the approaches shown, but may be available by a number of different ways. The phraseology and methodology given below is not limited to that outlined. Target compounds are delineated for the tetrahydroquinoline-containing systems 9-14. The heteroarotinoids 9, with one geminal dimethyl group at C-4 and a N—CH$_3$ group, allowed an assessment of the significance of the presence of these two groups on activity. The conversion of 4-bromoaniline (47) to 48, followed by the sequence 48→49→50→51→52→53→54→9→10, led to 9 and 10 in good yields. The steps are reasonable but reaction conditions are specific for best results. Salt 10 was obtained by simple N-methylation of 9. Members of both 9 and 10 were solids and gave the appropriate IR, NMR, and elemental analyses.

Scheme 8. Synthesis of chroman analogs 8 (2-Et-4-Et Series)

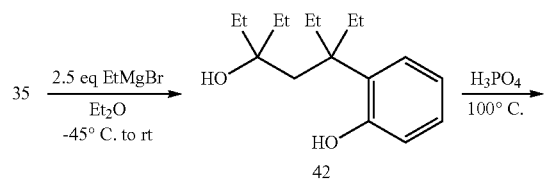

Scheme 9. Synthesis of tetrahydroquinoline analogs 9 and 10.

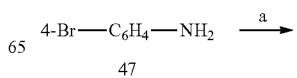

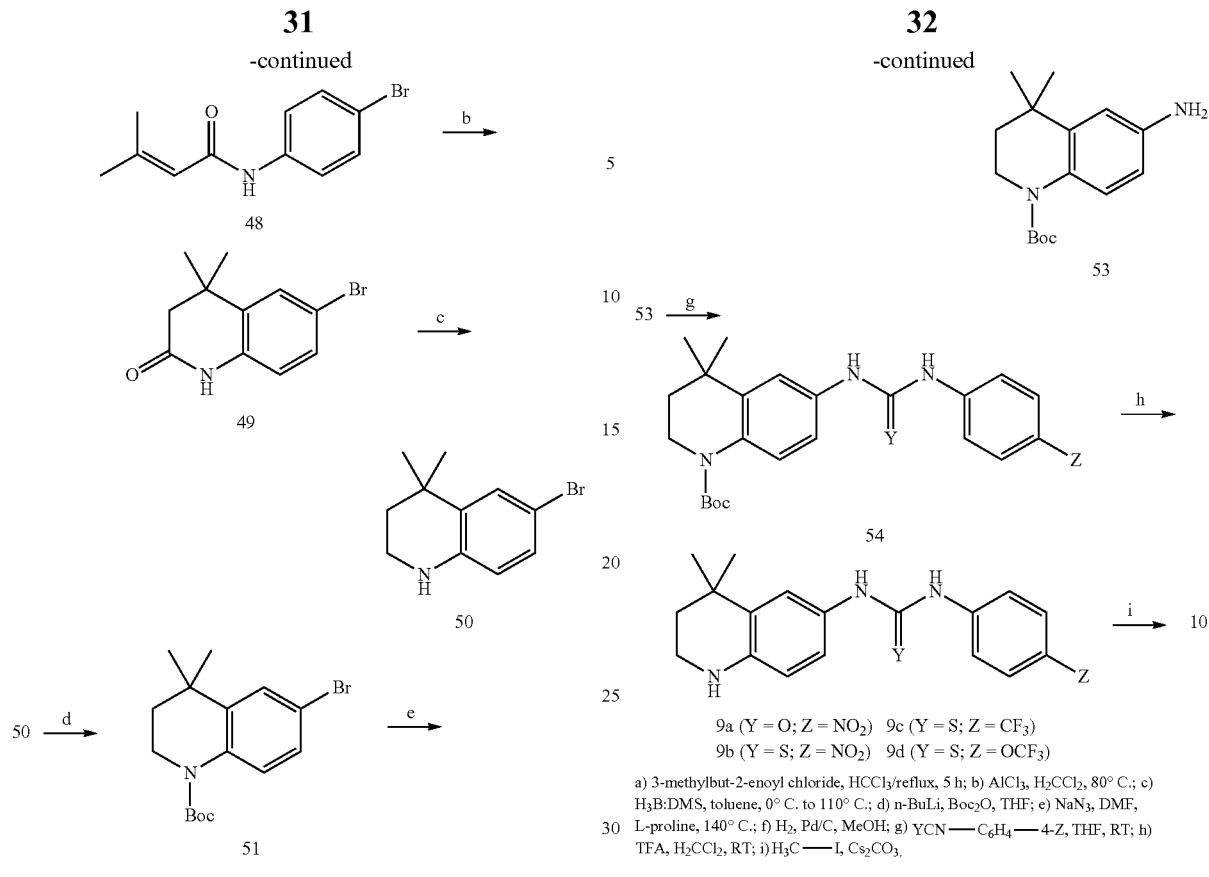

9a (Y = O; Z = NO$_2$)   9c (Y = S; Z = CF$_3$)
9b (Y = S; Z = NO$_2$)   9d (Y = S; Z = OCF$_3$)

a) 3-methylbut-2-enoyl chloride, HCCl$_3$/reflux, 5 h; b) AlCl$_3$, H$_2$CCl$_2$, 80° C.; c) H$_3$B:DMS, toluene, 0° C. to 110° C.; d) n-BuLi, Boc$_2$O, THF; e) NaN$_3$, DMF, L-proline, 140° C.; f) H$_2$, Pd/C, MeOH; g) YCN—C$_6$H$_4$—4-Z, THF, RT; h) TFA, H$_2$CCl$_2$, RT; i) H$_3$C—I, Cs$_2$CO$_3$.

Generation of the tetrahydroquinoline-containing series 11 (Scheme 10) progressed utilizing special conditions for each step with methods familiar to someone skilled in the art of synthesis but have not been previously utilized as illustrated. Starting with 4-bromoaniline (47), conversions of 55→56→57→58→59→60→11 gave good yields. Formation of 11 involved adding the required isocyanate or isothiocyanate in THF to 60 in the normal manner. All members of 11 were solids with sharp melting points and were structurally confirmed by IR, NMR, and elemental analyses.

Scheme 10. Syntheses of tetrahydroquinolin-3-one members of 11

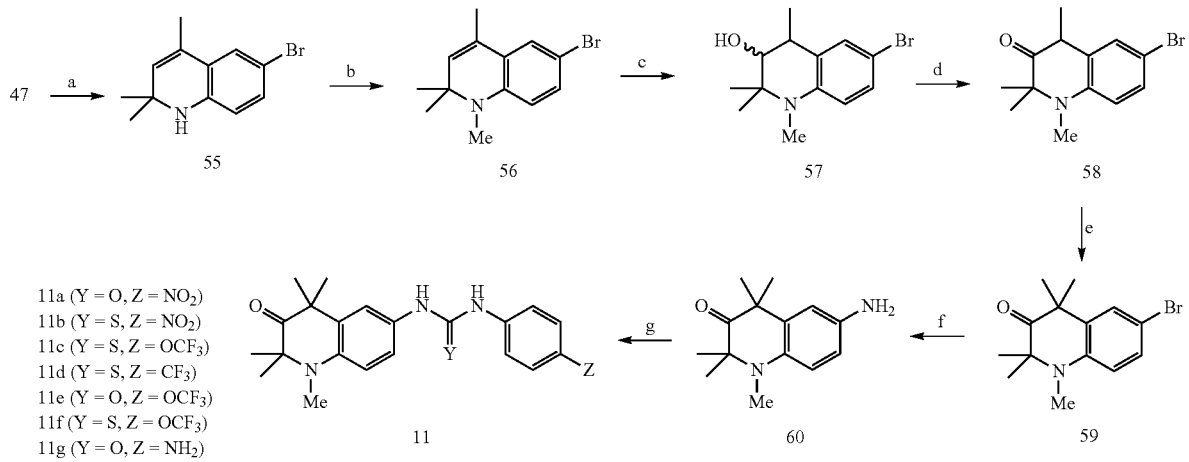

11a (Y = O, Z = NO$_2$)
11b (Y = S, Z = NO$_2$)
11c (Y = S, Z = OCF$_3$)
11d (Y = S, Z = CF$_3$)
11e (Y = O, Z = OCF$_3$)
11f (Y = S, Z = OCF$_3$)
11g (Y = O, Z = NH$_2$)

a) acetone, Bi(OTf)$_3$, reflux; b) NaH, MeI, DMF, RT; c) H$_3$B:THF complex, THF, 10-15° C.; 3 M NaOH, 30% H$_2$O$_2$; d) (OCl)$_2$, DMSO, TEA, H$_2$CCl$_2$, -60° C.; e) LiHMDS, MeI, THF; f) CuI, L-proline, aq NH$_3$, DMF, 110° C.; g) 4-YCN—C$_6$H$_4$—Z, THF, RT; h) Fe/NH$_4$Cl, 4:1 EtOH:H$_2$O, 85° C, Scheme 11 displays the sequence to 12 starting with ethyl isobutyrate in a series of steps involving 61→62→63→64→65→66→67→68→69→12. Individual conversions followed common methods but required special conditions. Intermediates 61, 62, 63, 64, and 65 were light oils that were purified by distillation, while the succeeding members 66, 67, 68, and 69 were solids or semi-solids. Compound 12 was a high melting solid identified by IR, NMR and elemental analysis, and all preceding intermediates were also confirmed by IR and NMR analysis. Compound 12 is the counterpart of standard SHetA2 with the exception that the former has an N—CH$_3$ group while the latter has an S atom in ring A.

Scheme 12. Synthesis of members of 13.

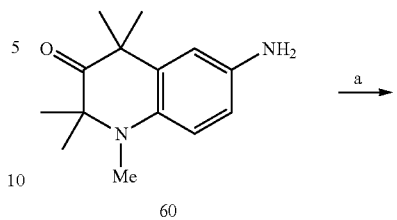

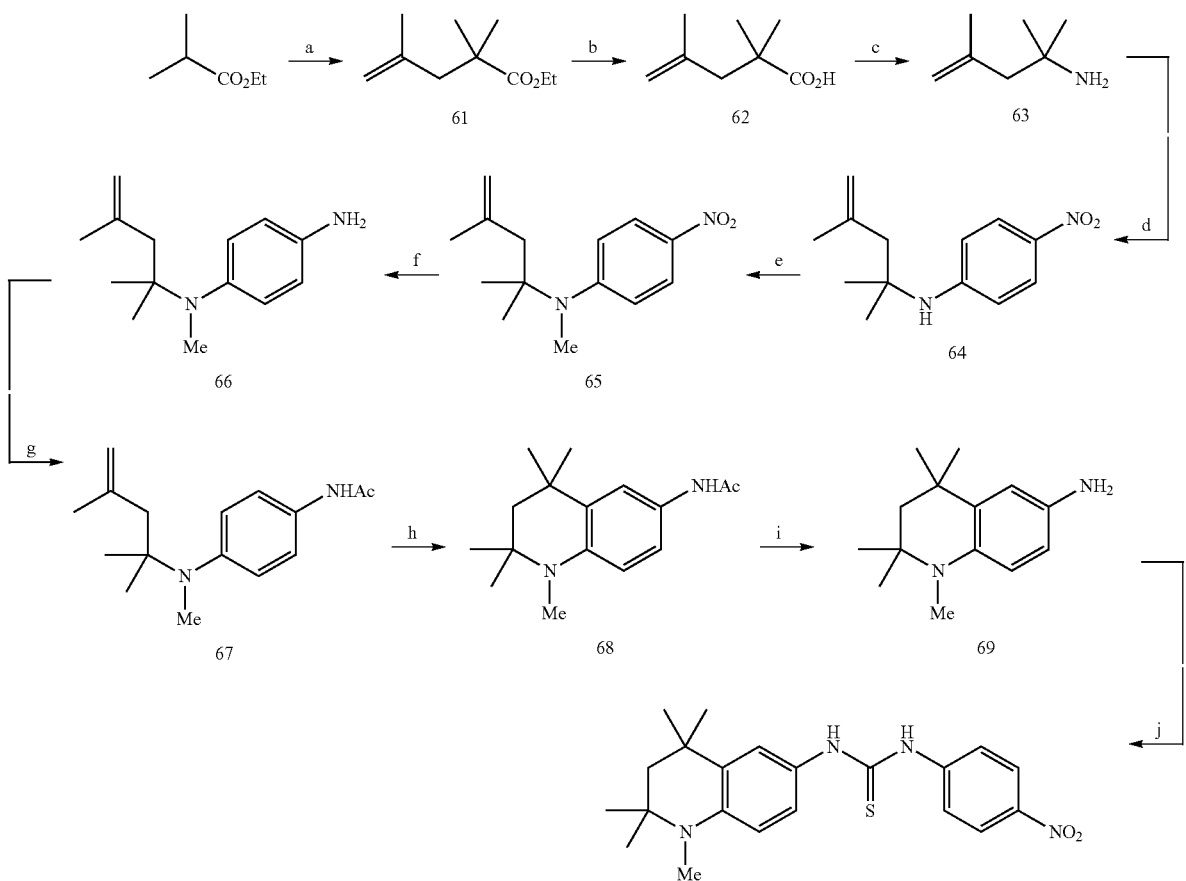

Scheme 11. Sythesis of compound 12 a) LDA, THF, -78° C.;H$_2$C═C(CH$_3$)CH$_2$I, -78° C. to 23° C.; b) NaOH, MeOH, 60° C, to 70° C.; H$_3$O$^+$; c) TEA, PhH; (PhO)$_2$P(O)N$_3$, 0° C. to 23° C., then reflux; d) 4-F—C$_6$H$_4$—NO$_2$, DMSO, 80° C.; e) NaH, MeI, DMF, 23° C.; f) Fe, NH$_4$Cl, EtOH/H$_2$O, reflux; g) AcCl, pyridine, 23°C.; h) AlCl$_3$, DCM -78° C. to 23° C.; i) 70% H$_2$SO$_4$, reflux; 30% NaOH; j) 4-SCN—C$_6$H$_4$—NO$_2$, THF, 23° C.

Preparation of Members of Series 13.

Members of 13 were prepared in a normal manner as shown in Scheme 12. Reduction of the carbonyl group in 60 led to the secondary alcohol 70 which was a brown oil that was quickly converted to members of 13. All members of 13 were solids, melted sharply and were supported by IR, NMR, and the correct elemental analyses. Compounds 13 possessed the hydroxyl group which can H-bond with proteins, including mortalin.

-continued

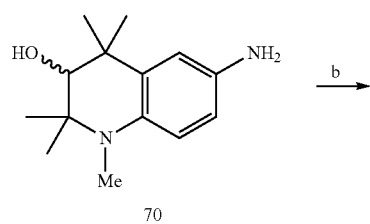

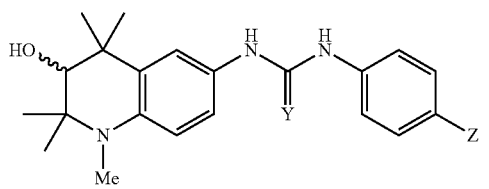

13

13a (Y = O, Z = NO₂)   13d (Y = S, Z = CF₃)
13b (Y = S, Z = NO₂)   13e (Y = O, Z = OCF₃)
13c (Y = O, Z = CF₃)   13f (Y = S, Z = OCF₃)

a) LiAlH₄, THF, RT; b) YCN—C₆H₄—4-Z, THF, RT.

In order to obtain members of 14, it was necessary to develop the synthesis of 76 as illustrated in Scheme 13 below. When carefully executed, the individual steps in the sequence 70→71→73→74→75→76 were accomplished in good yields. Condensing known 4-acetamidothiophenol with 71 in the first step was important for obtaining 72 in high yield.

Scheme 13. Synthesis of 6-isothiocyanato-2,2,4,-tetramethylthiochroman (76).

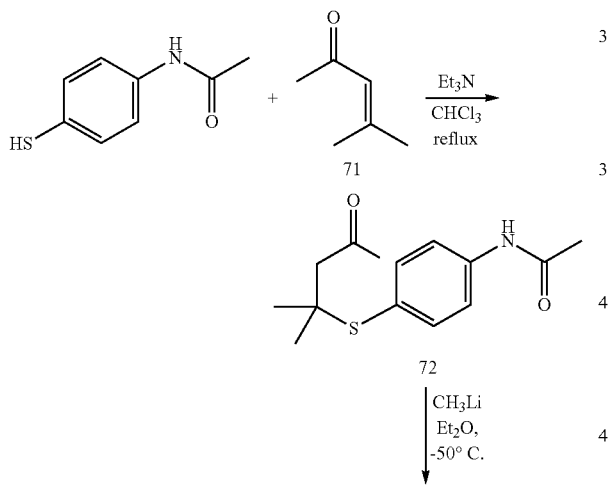

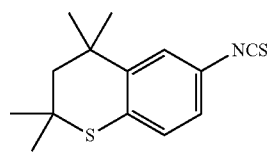

76

Utilizing the key intermediate 77, the free base of 75, members of 14 could be realized. The one-step process in Scheme 14 involved a condensation of 77 with a variety of isocyanates and isothiocyanates to generate a variety of substituted members of 14.

Scheme 14. Synthesis of members of 14.

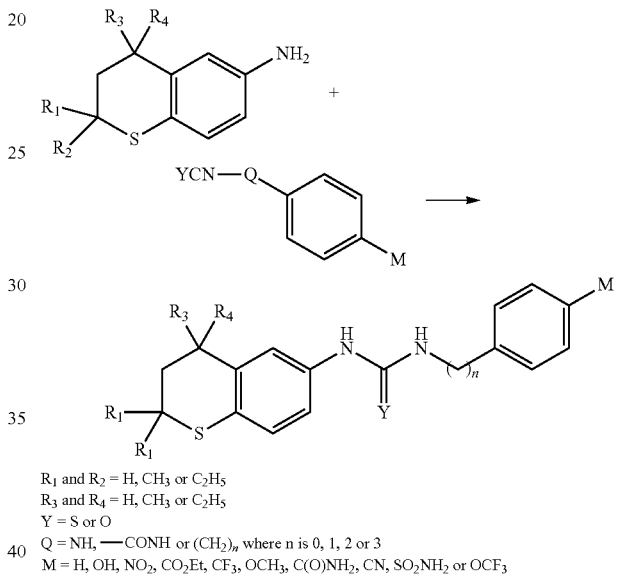

$R_1$ and $R_2$ = H, CH₃ or C₂H₅
$R_3$ and $R_4$ = H, CH₃ or C₂H₅
Y = S or O
Q = NH, —CONH or (CH₂)$_n$ where n is 0, 1, 2 or 3
M = H, OH, NO₂, CO₂Et, CF₃, OCH₃, C(O)NH₂, CN, SO₂NH₂ or OCF₃

Compound 14v required a special method as illustrated in Scheme 15. Reacting 4-acetamidothiphenol with 1-bromo-3-methylbut-2-ene gave intermediate 78. The remaining steps followed standard procedures. The yellow solid 14v gave the proper spectral and elemental analysis.

Scheme 15. Synthesis of desmethyl derivative 14v.

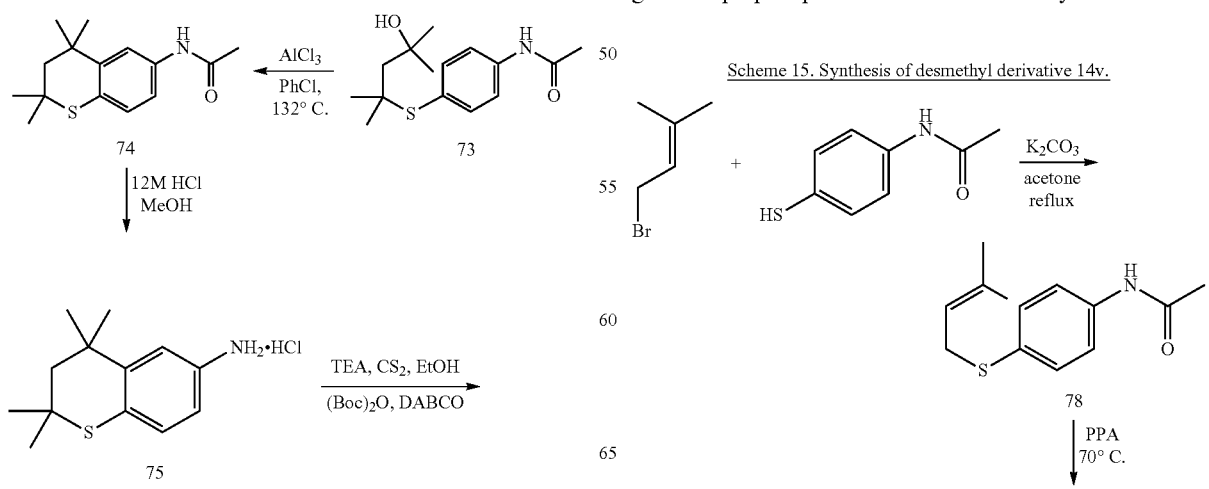

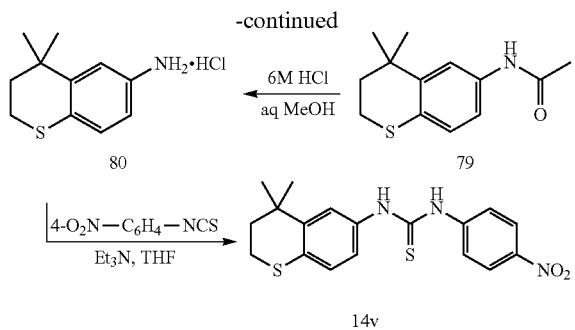

Example 2. Experimental Procedures and Results for Testing of the Compounds

The following explanation of experimental procedures employed to evaluate the compounds of this invention and results obtained therefrom will serve to further illustrate the value of the invention and the utility of the inventive compounds.

Method for Growth Inhibition Assay

To illustrate the general activity of the compounds inhibiting growth of human A2480 ovarian cancer cells, selected compounds were synthesized and evaluated. The compounds were dissolved in DMSO at a concentration of 0.01 M. The human ovarian cancer cell line A2780 was plated in 96-well tissue culture dishes at a concentration of 3000 cells per well in RPMI medium supplemented with 10% fetal bovine serum and a mixture of antibiotics and antimycotics. The next day, the cultures were treated in triplicate with compound concentrations ranging from 2 µM to 8 µM increments. For compound 12, additional experiments were performed with concentrations of 10 µM and a series of two-fold dilutions to 156 nM. Control cultures were treated with DMSO solvent only. After 72 h of incubation, the CELLTITER 96® Non-Rad Cell Proliferation Assay (Promega) was used to quantify the remaining metabolically living cells. After subtracting blank values, the optical density (OD) readouts of the assay for the treated cultures were normalized with the average OD of the control cultures. For each compound, the experiment was repeated at least once, resulting in a minimum of 6 dose-response curves. For SHetA2, 24 response curves were available for statistical fitting parameters. A custom program was written in GNU Octave, a free software compatible with Matlab, to fit the dose-response curves with a four-parameter sigmoid function, extracting the $IC_{50}$ and efficacy (the maximal % growth inhibition) parameters.

Theoretical Docking Methods

AutoDock 4.2 [G. M. Morris, R. Huey, W. Lindstrom, M. F. Sanner, R. K. Belew, D. S. Goodsell, A. J. Olson, AutoDock4 and AutoDockTools4: Automated docking with selective receptor flexibility, J. Comput. Chem., 30 (2009) 2785-2791] was used to dock the compounds to the substrate binding domain of mortalin (Protein Data Bank ID: 3N8E). For the compounds, ChemSketch™ (Advanced Chemistry Development, Inc. ADC/Labs, Toronto, Canada) was used to generate the SMILES notations, which were subsequently converted to PDB files with initial three-dimensional coordinates using OpenBabelGUI [N. M. O'Boyle, M. Banck, C. A. James, C. Morley, T. Vandermeersch, G. R. Hutchison, OpenBabel: An open chemical toolbox, J. Cheminform., 3 (2011) 33]. AutoDockTool (ADT) [G. M. Morris, R. Huey, W. Lindstrom, M. F. Sanner, R. K. Belew, D. S. Goodsell, A. J. Olson, AutoDock4 and AutoDockTools4: Automated docking with selective receptor flexibility, J. Comput. Chem., 30 (2009) 2785-2791] was then employed to prepare the protein and compounds with partial charges and also for the latter rotatable bonds. Only polar hydrogens were retained in the molecules. Kollman united atom partial charges and solvation parameters were assigned. The search space of 44 Å×47 Å×41 Å was slightly bigger than the protein molecule and the grid spacing was 0.375 Å. Autogrid was run first to prepare the coordinates system and then a Lamarckian genetic algorithm was applied with a population size of 150 and 25 million maximum evaluations. The minimum empirical binding free energy (ΔG) between the compound and receptor was reported. The binding affinity $K_i$ is calculated from binding free energy using the relation $\Delta G = -RT \ln(K_i)$, where R is the gas constant. All dockings were performed on an iMac computer with a 2.4 GHz Intel Core i3 processor and 4 GB RAM.

To illustrate the useful biological activity of these chroman-substituted and tetrahydroquinoline-substituted heteroarotinoids, the compounds were screened against human A2480 ovarian cancer cells. The data is presented in Tables 1 and 2.

It is clear from the data in Tables 1 and 2 that select groups on both the A ring and the B ring are important for activity. The docking of the compounds to mortalin was exploited to determine binding affinity and ascertain if a correlation existed between docking and activity using SHetA2 as the standard. Considering the efficacy values of the chroman-substituted agents as measures of activity, it is clear (Table 1) that the efficacy in 2a (Z=NO₂, Y=S), 3b (Z=CF₃, Y=O), 3c (Z=CN, Y=O), 3d (Z=OCF₃, Y=O), 6a (Z=NO₂, Y=S), 6b (Z=NO₂, Y=O), 6c (Z=CF₃, Y=O), 7a (Z=NO₂, Y=S), 7c (Z=NO₂, Y=O), 7d (Z=CF₃, Y=O), 8a (Z=NO₂, Y=S), and 8b (Z=NO₂, Y=O) exceeded the efficacy of SHetA2 (1), the standard. The $IC_{50}$ values, compared to that of SHetA2 (1), were exceeded by those of 6a, 6b, 6c, 7c, 7d, 8b, 8c, and 8d. Overall, two agents with the best $IC_{50}$ and efficacy values taken on the whole were 6b (Z=NO₂, Y=O; 2.17, 93.3%) and 7c (Z=NO₂, Y=O, 2.05, 93.6%) compared to that of SHetA2 (Z=NO₂, Y=S, 3.17, 84.3%). An overall appraisal of the data revealed that the urea derivatives were more active than the thiourea counterparts.

TABLE 1

Half-maximal inhibitory concentration and efficacy values derived from
the cellular dose-response data for members of the chroman-containing series (X = O). Shown
also are the standard errors of mean (SEM) and binding free energy and binding affinity values
of com-pounds docked to the mortalin substrate-binding domain (SBD) and compared to SHetA2
(1).

|  | $IC_{50}$ (μM) | $IC_{50}$ SEM | Efficacy (%) | Efficacy SEM | $-\Delta G$ (kcal/mol) | $K_i$ (μM) |
| --- | --- | --- | --- | --- | --- | --- |
| SHetA2 | 3.17 | ±0.05 | 84.3 | ±0.7 | 8.5 | 0.6 |
| 2a | 6.97 | 0.08 | 87 | 6 | 8.1 | 1.3 |
| 2b | 4.3 | 3.0 | 26 | 10 | 8.0 | 1.5 |
| 2c | 4.7 | 0.2 | 22 | 4 | 7.8 | 2.1 |
| 2e | 6.9 | 0.9 | 32 | 2 | 8.3 | 0.9 |
| 03a | 4.1 | 0.1 | 79 | 4 | 8.5 | 0.6 |
| 3c | 3.6 | 0.1 | 88.4 | 1.4 | 7.9 | 1.8 |
| 3d | 4.7 | 0.3 | 93 | 3 | 8.6 | 0.5 |
| 3f | 4.56 | 0.05 | 91.5 | 0.8 | 7.7 | 2.5 |
| 4a | 6.4 | 0.6 | 19 | 5 | 7.8 | 2.1 |
| 4b | 5.5 | 1.5 | 28 | 0.6 | 7.0 | 7.9 |
| 4c | 4.3 | 0.4 | 16 | 6 | 7.3 | 4.8 |
| 5a | 6.7 | 0.2 | 74 | 11 | 8.3 | 0.9 |
| 5b | 5 | 0.3 | 47 | 2 | 7.8 | 2.1 |
| 5c | 3.5 | 0.4 | 36 | 3 | 8.1 | 1.3 |
| 6a | 2.9 | 0.1 | 93.9 | 0.5 | 8.5 | 0.6 |
| 6b | 2.17 | 0.04 | 93.2 | 0.1 | 8.3 | 0.9 |
| 6c | 2.45 | 0.04 | 92.4 | 0.1 | 8.1 | 1.3 |
| 7a | 3.69 | 0.04 | 95.7 | 0.4 | 8.4 | 0.8 |
| 7b | 4.7 | 0.5 | 11.8 | 0.9 | 8.2 | 1.1 |
| 7c | 2.05 | 0.02 | 93.66 | 0.05 | 8.4 | 0.8 |
| 7d | 2.43 | 0.05 | 93.3 | 0.1 | 8.6 | 0.5 |
| 8a | 4.6 | 0.2 | 94.00 | 1.00 | 8.7 | 0.5 |
| 8b | 2.09 | 0.02 | 91.4 | 0.3 | 8.7 | 0.5 |
| 8c | 2.0 | 0.1 | 86.2 | 0.6 | 8.8 | 0.4 |
| 8d | 3.00 | 0.06 | 67 | 3 | 8.8 | 0.4 |

TABLE 2

Half-maximal inhibitory concentrations and efficacy values of
tetrahydroquinoline-containing members (X = NH or N—CH$_3$). Data are derived from cellular
dose-response data, and binding free energy and binding affinity values of compounds docked to
the mortalin substrate-binding domain (SBD) and compared to SHetA2 (1). See Scheme 9 for the
synthesis of compounds 9a-9d and 10; see Scheme 10 for the synthesis of 11a-11g; see Scheme
11 for the synthesis of 12; and see Scheme 12 for the synthesis of 13a-f.

| Cpd | Y | Z | $IC_{50}$ (μM) | Efficacy (%) | $-\Delta G$ (kcal/mol) | $K_i$ (μM) |
| --- | --- | --- | --- | --- | --- | --- |
| SHetA2 | S | NO$_2$ | 3.17 (±0.05) | 84.3 (±0.7) | 8.5 | 0.6 |
| 9a | O | NO$_2$ | 6.9 (0.2) | 17.1 (±1.2) | 8.2 | 1.1 |
| 9b | S | NO$_2$ | 7.1 (0.3) | 17.8 (±1.6) | 7.9 | 1.6 |
| 9c | S | CF$_3$ | 6 (0.2) | 42 (±3) | 7.5 | 3.3 |
| 9d | S | OCF$_3$ | 7.1 (0.8) | 24 (±2) | 7.2 | 5.4 |
| 10 | O | NO$_2$ | 6.6 (0.3) | 22 (±4) | 8.5 | 0.7 |
| 11a | O | NO$_2$ | 3.8 (0.1) | 94.8 (±2.2) | 8.9 | 0.3 |
| 11b | S | NO$_2$ | 4.4 (0.2) | 91.4 | 8.2 | 1.1 |
| 11c | O | CF$_3$ | 2.58 (0.08) | 90.1 (±1.4) | 8.0 | 1.5 |
| 11d | S | CF$_3$ | 3.9 (0.1) | 90.8 (±2.0) | 7.9 | 1.6 |
| 11e | O | OCF$_3$ | 2.4 (0.2) | 91.3 (±1.3) | 7.9 | 1.8 |
| 11f | S | OCF$_3$ | 5.4 (0.6) | 76 (±8) | 7.7 | 2.4 |
| 11g | S | NH$_2$ | 7.7 (1.4) | 24 (±4) | 8.2 | 1.1 |
| 12 | S | NO$_2$ | 4.49 (0.18) | 91.7 (±0.42) | 8.7 | 0.5 |
| 13a | O | NO$_2$ | 8.4 (1.9) | 26 (±4) | 8.0 | 1.6 |
| 13b | S | NO$_2$ | 10 (5) | 25 (±4) | 7.7 | 2.3 |
| 13c | O | CF$_3$ | 6.7 (0.5) | 25 (±5) | 8.4 | 0.7 |
| 13d | O | OCF$_3$ | 7.6 (0.7) | 56.1 (±2.4) | 7.7 | 2.3 |
| 13e | S | CF$_3$ | 7.8 (0.2) | 23.6 (±3.3) | 8.2 | 1.1 |
| 13f | S | OCF$_3$ | 13.1 (6.1) | 15.3 (±3.3) | 7.6 | 2.9 |

Series 14 compounds are those comprising a thiochroman group. Results for this groups are shown in Table 3, where the standard of measurement was SHetA2 which is the last component (X) in Table 3. It is noted that a range of activities was exhibited by the series 14 compounds, but 14a, 14b, 14c, 14d, 14e, and 14f exceeded that of SHetA2 in efficacy as did 14j, 14k, 14l, 14m, 14n, and 14o although the $IC_{50}$ values varied. The dimethyl compound 14w also had an efficacy value better than SHetA2, but the $IC_{50}$ was slightly less.

The compounds in Table 3 were designed to maintain the c log D values between 3 and 6 to avoid off-target liabilities arising due to interactions with the Human Ether-a-go-go Related Gene (HERG), cytochrome P450 (CYP), and other transporting molecules.

1-(4-Nitrophenyl)-3-(2,2,4,4-tetramethylchroman-6-yl)thiourea (2a)

Pale yellow solid (160 mg, 85%), mp 176-177° C.; IR: 3307, 3190, 1542, 1335 cm$^{-1}$; $^1$H NMR (400 MHz, CDCl$_3$): δ 8.20 (d, J=9.1 Hz, 2H), 8.00 (br s, 1H), 7.76 (coincident s, 1H and d, J=9.1 Hz, 2H), 7.22 (d, J=2.6 Hz, 1H), 7.04 (dd, J=8.5, 2.6 Hz, 1H), 6.89 (d, J=8.5 Hz, 1H), 1.86 (s, 2H), 1.38 (s, 6H), 1.36 (s, 6H); $^{13}$C NMR (101 MHz, CDCl$_3$): δ 180.5, 153.9, 145.4, 144.9, 134.6, 128.4, 125.9, 125.8, 125.3, 123.6, 120.6, 75.8, 48.7, 33.0, 31.4, 28.7. Anal. Calcd for C$_{20}$H$_{23}$N$_3$O$_3$S: C, 62.32; H, 6.01; N, 10.90. Found: C, 62.51; H, 6.05; N, 10.93. Although 2a was reported and analyzed, the current purification procedure raised the mp by about 10° C.

TABLE 3

The data contain maximal inhibitory activity, binding affinity, and efficacy for the 14 series of compounds, as compared to SHetA2. L refers to the linking atoms between the thiochroman and the benzyl moiety; Ring B refers to the benzyl moiety (e.g. see Scheme 3).

| Cpd | R | L | Ring B | clogD | clog P | IC$_{50}$ (µM) | % Efficacy |
|---|---|---|---|---|---|---|---|
| 14a | CH$_3$ | NHC(O)NH | C$_6$H$_4$—4—CF$_3$ | 6.17 | 6.2 | 3.79 ± 0.05 | 93.3 ± 0.1 |
| 14b | CH$_3$ | NHC(O)NH | C$_6$H$_4$—4—OCF$_3$ | 6.28 | 6.3 | 1.86 ± 0.09 | 95.6 ± 0.4 |
| 14c | CH$_3$ | NHC(O)NH | C$_6$H$_4$—4—CN | 5.26 | 5.3 | 3.93 ± 0.03 | 93.3 ± 0.1 |
| 14d | CH$_3$ | NHC(S)NH | C$_6$H$_4$—4—Cl | 6.15 | 6.1 | 3.17 ± 0.25 | 91.9 ± 0.5 |
| 14e | CH$_3$ | NHC(S)NH | C$_6$H$_4$—4—CF$_3$ | 6.32 | 6.3 | 2.86 ± 0.29 | 95.9 ± 0.6 |
| 14f | CH$_3$ | NHC(S)NH | C$_6$H$_4$—4—OCF$_3$ | 5.93 | 5.9 | 3.51 ± 0.07 | 95.3 ± 0.4 |
| 14g | CH$_3$ | NHC(S)NH | C$_6$H$_4$—4—C(O)NH$_2$ | 3.95 | 3.9 | 3.53 ± 0.12 | 64.2 ± 1.8 |
| 14h | CH$_3$ | NHC(S)NH | C$_6$H$_4$—4—OCH$_3$ | 5.45 | 5.4 | 2.78 ± 0.47 | 59.8 ± 1.2 |
| 14i | CH$_3$ | NHC(S)NH | C$_6$H$_4$—3—OCH$_3$ | 5.45 | 5.4 | 3.04 ± 0.52 | 38.8 ± 0.04 |
| 14j | CH$_3$ | NHC(S)NHCH$_2$ | Ph | 5.70 | 5.7 | 3.03 ± 0.47 | 85.6 ± 0.6 |
| 14k | CH$_3$ | NHC(S)NHCH$_2$CH$_2$ | Ph | 6.34 | 6.3 | 3.19 ± 0.47 | 88.2 ± 0.3 |
| 14l | CH$_3$ | NHC(S)NHCH$_2$ | C$_6$H$_4$—4—Cl | 6.45 | 6.4 | 2.98 ± 0.44 | 89.4 ± 2.8 |
| 14m | CH$_3$ | NHC(S)NHCH$_2$ | C$_6$H$_4$—4—NO$_2$ | 5.75 | 5.7 | 4.70 ± 0.11 | 94.5 ± 0.6 |
| 14n | CH$_3$ | NHC(S)NHCH$_2$ | C$_6$H$_4$—4—CF$_3$ | 6.52 | 6.5 | 4.82 ± 0.41 | 95.3 ± 0.3 |
| 14o | CH$_3$ | NHC(S)NHCH$_2$ | C$_6$H$_4$—4—OCH$_3$ | 5.64 | 5.6 | 3.26 ± 0.43 | 89.6 ± 0.9 |
| 14p | CH$_3$ | NHC(S)NHCH$_2$ | C$_6$H$_4$—4—OH | 5.15 | 5.1 | 3.23 ± 0.49 | 56.8 ± 3.3 |
| 14q | CH$_3$ | NHC(S)NHNH | Ph | 5.84 | 5.8 | 7.03 ± 0.31 | 63.6 ± 3.7 |
| 14r | CH$_3$ | NHC(S)NHNHC(O) | Ph | 4.08 | 4.0 | 0.82 ± 0.21 | 67.9 ± 2.6 |
| 14s | CH$_3$ | NHC(S)NHNHC(O) | C$_6$H$_4$—4—NO$_2$ | 3.85 | 3.8 | 3.15 ± 0.19 | 43.3 ± 2.9 |
| 14t | CH$_3$ | NHC(S)NHNHC(O) | C$_6$H$_4$—4—OCF$_3$ | 4.97 | 4.9 | 3.60 ± 0.18 | 57.4 ± 0.4 |
| 14u | CH$_3$ | NHC(S)NHNHC(O) | C$_6$H$_3$—3,5—CF$_3$ | 5.45 | 5.4 | 4.0 ± 0.12 | 61.4 ± 2.9 |
| 14v | H | NHC(S)NH | Ph—4—NO$_2$ | 3.36 | 3.3 | 4.01 ± 0.19 | 93.5 ± 1.7 |
| 14x | CH$_3$ | CH$_3$NHC(S)NH | Ph—4—NO$_2$ | 5.15 | 5.1 | 3.17 ± 0.1 | 84.3 ± 0.7 |

NOTE:
The last entry (x) is the data for the standard [SHetA2] to which the test compounds were compared.

Example 3. Synthesis Details and Analyses

This Example provides details of reactions leading to the compounds described herein and the analyses of the compounds. The compounds are keyed according to compound number and the Scheme in which they are depicted in EXAMPLE 1.

The following section pertains to Scheme 4, Scheme 5, Scheme 6, Scheme 7 and Scheme 8

To obtain members of 2 and 3, the following general procedure was employed. A stirred solution of 1 mol eq of known 6-amino-2,2,4,4-tetramethylchroman (21) in dry THF was treated at 0° C. with 1.05 mol eq of the appropriate isothiocyanate or isocyanate. Stirring was continued overnight with gradual warming to room temperature. The solvent was removed under vacuum to yield an oily residue. The residue was dissolved in chloroform and treated with a small amount of pentane until crystallization commenced. In all cases, crystals obtained were filtered and washed with ether:pentane (1:1) to afford the products, which were dried (high vacuum) at 50° C.

Ethyl 4-(3-(2,2,4,4-Tetramethylchroman-6-yl)thioureido)benzoate (2b)

White solid (70 mg, 70%), mp 140-141° C.; IR: 3349, 3284, 3195, 1709 cm$^{-1}$; $^1$H NMR (400 MHz, CDCl$_3$): δ 8.02 (d, J=8.3 Hz, 2H), 7.91 (br s, 1H), 7.72 (br s, 1H), 7.57 (d, J=8.3 Hz, 2H), 7.24 (d, J=1.9 Hz, 1H), 7.04 (dd, J=8.5, 1.9 Hz, 1H), 6.85 (d, J=8.5 Hz, 1H), 4.36 (q, J=7.1 Hz, 2H), 1.86 (s, 2H), 1.38 (t, J=7.1 Hz, 3H), 1.37 (s, 6H), 1.35 (s, 6H); $^{13}$C NMR (101 MHz, CDCl$_3$): δ 179.6, 165.9, 152.5, 142.0, 133.4, 130.5, 128.2, 127.6, 125.0, 124.9, 123.0, 119.5, 75.2, 61.0, 48.5, 32.8, 31.1, 28.5, 14.3. Anal. Calcd for C$_{23}$H$_{28}$N$_2$O$_3$S: C, 66.96; H, 6.84; N, 6.79. Found: C, 66.88; H, 6.85; N, 6.68.

1-(2,2,4,4-Tetramethylchroman-6-yl)-3-(4-(trifluoromethyl)phenyl)thiourea (2c)

White solid (82 mg, 81%), mp 166-168° C.; IR: 3357, 3196, 1598, 1491, 1324 cm$^{-1}$; $^1$H NMR (400 MHz, CDCl$_3$): δ 7.81 (br s, 1H), 7.63 (d, J=8.7 Hz, 2H), 7.61 (br s, 1H), 7.59 (d, J=8.7 Hz, 2H), 7.23 (d, J=2.6 Hz, 1H), 7.04 (dd, J=8.6, 2.6 Hz, 1H), 6.87 (d, J=8.6 Hz, 1H), 1.86 (s, 2H), 1.38 (s, 6H), 1.35 (s, 6H); $^{13}$C NMR (101 MHz, CDCl$_3$): δ 179.9, 152.6, 141.2, 133.6, 128.0, 128.6, 126.0 (q, J=3.9 Hz), 125.1, 125.0, 123.9, 123.9 (q, J=271.9 Hz), 119.6, 75.7, 48.8, 33.0, 31.4, 28.7. Anal. Calcd for C$_{21}$H$_{23}$F$_3$N$_2$OS: C, 61.75; H, 5.68; N, 6.86. Found: C, 61.47; H, 5.62; N, 6.87.

4-(3-(2,2,4,4-Tetramethylchroman-6-yl)thioureido) benzenesulfonamide (2d)

Tan solid (90 mg, 78%), mp 186-187° C.; IR: 3351, 3258, 3179, 1339, 1162 cm$^{-1}$; $^1$H NMR (400 MHz, DMSO-d$_6$): δ 9.92 (s, 1H), 9.85 (s, 1H), 7.74 (d, J=8.0 Hz, 2H), 7.68 (d, J=8.0 Hz, 2H), 7.39 (s, 1H), 7.27 (s, 2H), 7.14 (s, J=7.6 Hz, 1H), 6.70 (d, J=7.6 Hz, 1H), 1.81 (s, 2H), 1.30 (2s, 12H); $^{13}$C NMR (101 MHz, DMSO-d$_6$): δ 179.8, 149.9, 143.3, 139.3, 132.1, 131.4, 126.5, 124.0, 123.5, 122.9, 117.6, 74.7, 48.5, 33.0, 31.1, 28.6. Anal. Calcd for C$_{20}$H$_{25}$N$_3$O$_3$S$_2$.0.5 CH$_3$CH$_2$OH: C, 56.99; H, 6.38; N, 9.49. Found: C, 56.67; H, 6.08; N, 9.87.

1-(2,2,4,4-Tetramethylchroman-6-yl)-3-(4-(trifluoromethyl)phenyl)urea (3a)

White solid (93 mg, 80%), mp 245-246° C.; IR: 3302, 3175, 1646, 1599, 1491, 1325 cm$^{-1}$; $^1$H NMR (400 MHz, DMSO-d$_6$): δ 8.98 (s, 1H), 8.51 (s, 1H), 7.65 (d, J=8.6 Hz, 2H), 7.60 (d, J=8.6 Hz, 2H), 7.43 (s, 1H), 7.09 (d, J=8.7 Hz, 1H), 6.65 (d, J=8.7 Hz, 1H), 1.80 (s, 2H), 1.30 (s, 6H), 1.29 (s, 6H); $^{13}$C NMR (101 MHz, DMSO-d$_6$): δ 151.9, 146.9, 143.1, 131.5, 130.7, 125.4 (q, J=3.8 Hz), 124.0 (q, J=272.7 Hz), 120.9, 118.0, 117.1, 117.0, 116.8, 73.3, 47.9, 32.0, 30.1, 27.6. Anal. Calcd for C$_{21}$H$_{23}$F$_3$N$_2$O$_2$.0.3 H$_2$O: C, 63.40; H, 5.98; N, 7.04. Found: C, 63.71; H, 5.82; N, 7.12.

1-(4-Cyanophenyl)-3-(2,2,4,4-tetramethylchroman-6-yl)urea (3b)

Tan solid (51 mg, 61%), mp 225-226° C.; IR: 3341, 3206, 2221, 1665, 1590, 1491 cm$^{-1}$; $^1$H NMR (400 MHz, DMSO-d$_6$): δ 9.10 (s, 1H), 8.59 (s, 1H), 7.71 (d, J=8.0 Hz, 2H), 7.63 (d, J=8.0 Hz, 2H), 7.43 (s, 1H), 7.10 (d, J=7.9 Hz, 1H), 6.67 (d, J=7.9 Hz, 1H), 1.80 (s, 2H), 1.29 (s, 12H); $^{13}$C NMR (100 MHz, DMSO-d$_6$): δ 152.7, 148.1, 144.9, 133.7, 132.4, 131.8, 119.8, 119.2, 118.4, 118.1, 117.9, 103.4, 74.4, 18.8, 33.0, 31.1, 28.6. Anal. Calcd for C$_{21}$H$_{23}$N$_3$O$_2$: C, 72.18; H, 6.63; N, 12.03. Found: C, 72.00; H, 6.60; N, 11.76.

1-(2,2,4,4-Tetramethylchroman-6-yl)-3-(4-(trifluoromethoxy)phenyl)urea (3c)

White solid (151 mg, 76%), mp 219-221° C.; IR: 3313, 3206, 3154, 1646, 1256 cm$^{-1}$; $^1$H NMR (400 MHz, CDCl$_3$): δ 7.36 (d, J=8.1 Hz, 2H), 7.26 (obscured by solvent, 1H), 7.13 (d, J=8.1 Hz, 2H), 6.97 (dd, J=8.2, 1.5 Hz, 1H), 6.80 (d, J=8.2 Hz, 1H), 6.69 (s, 1H), 6.41 (s, 1H), 1.84 (s, 2H), 1.36 (s, 6H), 1.34 (s, 6H); $^{13}$C NMR (101 MHz, CDCl$_3$): δ 153.2, 147.8, 142.9, 139.7, 132.8, 131.7, 122.1, 120.7 (q, J=254.9 Hz), 119.7, 119.0, 117.90, 117.85, 74.3, 48.9, 33.0, 31.1, 28.6. Anal. Calcd for C$_{21}$H$_{23}$F$_3$N$_2$O$_3$: C, 61.76; H, 5.68; N, 6.86. Found: C, 61.91; N, 5.59; N, 6.85.

General Procedure for the Synthesis of Members of 4 and 5.

The procedures to obtain members of 4 and 5 were derived from the known precursor 4,4-dimethyl-3,4-dihydro-2H-1-benzopyran (23) in the normal sequence shown 16→22→23→24/25→26/27→4/5. An important step was the reduction of 24/25 to 26/27 using Fe/NH$_4$Cl in ethanol. The last step involved the reaction of 26 with the corresponding isocyanate or isothiocyanate in THF under similar conditions as outlined for the generation of members of 2 and 3. Derivatives were obtained in similar fashion.

1-(4-Nitrophenyl)-3-(4,4-dimethylchroman-6-yl) thiourea (4a)

Compound 23 was converted to 4a using the general procedure described above. Yellow solid (118 mg, 79%), mp 174-165° C.; IR: 3305, 3187, 1596, 1528, 1495, 1335 cm$^{-1}$; $^1$H NMR (400 MHz, CDCl$_3$): δ 8.20 (d, J=8.8 Hz, 2H), 7.97 (br s, 1H), 7.76 (d, J=8.8 Hz, 2H), 7.71 (s, 1H), 7.21 (d, J=2.2 Hz, 1H), 7.03 (dd, J=8.4, 2.2 Hz, 1H), 6.88 (d, J=8.4 Hz, 1H), 4.24 (t, J=5.3 Hz, 2H), 1.87 (t, J=5.3 Hz, 2H), 1.35 (s, 6H); $^{13}$C NMR (101 MHz, CDCl$_3$): δ 179.4, 153.9, 144.5, 144.0, 133.9, 127.4, 125.2, 125.1, 124.5, 122.8, 118.9, 63.3, 36.9, 30.94, 30.89. Anal. Calcd for C$_{18}$H$_{19}$N$_3$O$_3$S: C, 60.49; H, 5.36; N, 11.76. Found: C, 60.44; H, 5.35; N, 11.74.

1-(4,4-Dimethylchroman-6-yl)-3-(4-(trifluoromethyl)phenyl)thiourea (4b)

White solid (160 mg, 75%), mp 147-149° C.; IR: 3357, 3199, 1613, 1498, 1324 cm$^{-1}$; $^1$H NMR (400 MHz, CDCl$_3$): δ 8.00 (br s, 1H), 7.68 (br s, 1H), 7.65 (d, J=8.9 Hz, 2H), 7.61 (d, J=8.9 Hz, 2H), 7.22 (s, 1H), 7.03 (d, J=8.6 Hz, 1H), 6.86 (d, J=8.6 Hz, 1H), 4.22 (t, J=5.4 Hz, 2H), 1.85 (t, J=5.4 Hz, 2H), 1.34 (s, 6H); $^{13}$C NMR (101 MHz, CDCl$_3$): δ 179.9, 153.6, 141.5, 133.6, 127.9, 126.1 (q, J=3.8 Hz), 125.2, 125.1, 123.9, 123.9 (q, J=271.9 Hz), 118.6, 63.2, 36.9, 30.94, 30.86 (1 aromatic carbon not resolved). Anal. Calcd for C$_{19}$H$_{19}$F$_3$N$_2$OS: C, 59.99; H, 5.03; N, 7.36. Found: C, 60.04; H, 5.09; N, 7.37.

1-(4,4-Dimethylchroman-6-yl)-3-(4-(trifluoromethoxy)phenyl)thiourea (4c)

White solid (172 mg, 90%), mp 153-154° C.; IR: 3358, 3189, 1530, 1500, 1255 cm$^{-1}$; $^1$H NMR (400 MHz, CDCl$_3$): δ 7.71 (br s, 1H), 7.48 (coincident d, J=9.0 Hz, 2H and br s, 1H), 7.26 (s, 1H), 7.21 (d, J=9.0 Hz, 2H), 7.01 (d, J=8.5 Hz, 1H), 6.85 (d, J=8.5 Hz, 1H), 4.22 (t, J=5.3 Hz, 2H), 1.85 (t, J=5.3 Hz, 2H), 1.34 (s, 6H); $^{13}$C NMR (101 MHz, CDCl$_3$): δ 181.6, 154.5, 147.9, 137.3, 134.3, 128.8, 127.0, 126.1, 126.0, 122.8, 121.1 (q, J=257.1 Hz), 119.3, 63.7, 37.2, 31.13, 31.05. Anal. Calcd for C$_{19}$H$_{19}$F$_3$N$_2$O$_2$S: C, 57.57; H, 4.83; N, 7.07. Found: C, 57.54; H, 4.76; N, 7.19.

1-(4-Nitrophenyl)-3-(4,4-dimethylchroman-6-yl)urea (5a)

Compound 23 was converted to 5a using the general procedure described above. White solid (94 mg, 80%), mp 240-242° C.; IR: 3281, 3189, 1640, 1556, 1333 cm$^{-1}$; $^1$H NMR (400 MHz, DMSO-d$_6$): δ 9.13 (s, 1H), 8.64 (s, 1H), 8.18 (d, J=8.8 Hz, 2H), 7.68 (d, J=8.8 Hz, 2H), 7.42 (d, J=2.2 Hz, 1H), 7.10 (d, J=8.9 Hz, 1H), 6.67 (d, J=8.8, 2.2 Hz, 1H), 4.11 (t, J=5.2 Hz, 2H), 1.78 (d, J=5.2 Hz, 2H), 1.28 (s, 6H); $^{13}$C NMR (101 MHz, DMSO-d$_6$): δ 152.6, 149.4, 147.1, 141.2, 132.03, 132, 02, 125.6, 119.2, 118.3, 117.8, 117.0, 62.8, 37.5, 31.3, 30.8. Anal. Calcd for C$_{18}$H$_{19}$N$_3$O$_4$: C, 63.33; H, 5.61; N, 12.31. Found: C, 63.07; H, 5.64; N, 12.50.

(4,4-Dimethylchroman-6-yl)-3-[4-trifluoromethyl) phenyl]urea (5b)

White solid 5b (84 mg, 82%), mp 248-249° C.; IR: 3301, 3186, 1645, 1320 cm$^{-1}$; $^1$H NMR (400 MHz, DMSO-d$_6$): δ 8.98 (s, 1H), 8.52 (s, 1H), 7.65 (d, J=8.8 Hz, 2H), 7.61 (d, J=8.8 Hz, 2H), 7.41 (d, J=2.6 Hz, 1H), 7.11 (dd, J=8.8, 2.6 Hz, 1H), 6.66 (d, J=8.8 Hz, 1H), 4.10 (t, J=5.2 Hz, 2H), 1.77 (t, J=5.2 Hz, 2H), 1.28 (s, 6H); $^{13}$C NMR (100 MHz, DMSO-d$_6$): δ 152.9, 149.2, 144.1, 132.3, 132.0, 127.1 (q, J=3.6 Hz), 124.4 (q, J=270.0 Hz), 124.3, 119.7, 118.7, 118.6, 117.6, 62.7, 37.5, 31.3, 30.8. Anal. Calcd for C$_{19}$H$_{19}$F$_3$N$_2$O$_2$: C, 62.63; H, 5.26; N, 7.69. Found: C, 62.56; H, 5.32; N, 7.65.

1-(4,4-Dimethylchroman-6-yl)-3-(4-(trifluoromethoxy)phenyl)urea (5c)

White solid (78 mg, 73%), mp 230-231° C.: IR: 3308, 3198, 1645, 1267 cm$^{-1}$; $^1$H NMR (400 MHz, DMSO-d$_6$): δ 8.98 (s, 1H), 8.52 (s, 1H), 7.65 (d, J=8.9 Hz, 2H), 7.61 (d, J=8.9 Hz, 2H), 7.41 (d, J=1.9 Hz, 1H), 7.09 (dd, J=8.7, 1.9 Hz, 1H), 6.65 (d, J=8.7 Hz, 1H), 4.10 (t, J=5.2 Hz, 2H), 1.77 (t, J=5.2 Hz, 2H), 1.28 (s, 6H); $^{13}$C NMR (101 MHz, DMSO-d$_6$): δ 152.2, 147.9, 142.3, 138.8, 131.1, 130.5, 121.8, 120.3 (q, J=255.4 Hz), 119.4, 118.6, 117.6, 116.6, 61.7, 36.5, 30.1, 29.7. Anal. Calcd for C$_{19}$H$_{19}$F$_3$N$_2$O$_3$: C, 60.00; H, 5.04; N, 7.36. Found 60.06; 5.20; 7.33.

General Procedure for the Preparation of Members of 6, 7, and 8.

The methodology for obtaining members of 6, 7, and 8 paralleled to some degree that employed for the procurement of members of 4 and 5. Starting from known 4,4-dimethyl-chroman-2-one (16), a small excess of ethylmagnesium bromide in ether was added directly to yield 2-(4-ethyl-4-hydroxy-2-methylhexan-2-yl)phenol (28). The use of 28 and the intermediates 29→30/31→32/33→6 led to good yields of 6a, 6b, and 6c. Both precursors 30 and 31 could not be separated, but it was possible to separate amines 32 and 33. Only the 6-isomer 32 was employed to derive members of 6. The preparation of each other intermediate followed. Starting from phenol, the sequence of steps included 34→35→36→37→38/39→40/41→40→7 and produced members of 7 in good yields via the usual treatment of 40 with the required isocyanate or isothiocyanate. None of the intermediates were previously known and were therefore characterized. Thus, all members of 7 were subjected to IR, NMR, and elemental analysis along with a determination of their sharp melting points.

In a similar manner, members of 8 were prepared utilizing the starting compound 35. An excess of ethylmagnesium bromide in ether opened the ring in 35 to initiate the reaction sequence to produce members of 8 via 35→42→43→44/45→46?8. It was possible to separate 44/45 by preparative thin layer chromatography to give pure 44 (C-6 isomer). Reduction of the nitro group in 44 to the amino group yielded the required 46 (C-6 isomer) which was converted via reaction with the appropriate isocyanate or isothiocyanate to provide 8. Intermediates were oils which were purified by chromatography. All members of 8 were solids, had sharp melting points, and were characterized by IR, NMR, and elemental analyses.

1-(2,2-Diethyl-4,4-dimethylchroman-6-yl)-3-(4-nitrophenyl)thiourea (6a)

Compound 32 was converted to 6a using the appropriate isocyanate or isothiocyanate in the usual manner. Yellow solid (160 mg, 90%), mp 175-176° C.; IR: 3341, 3174, 1556, 1340, 1174 cm$^{-1}$; $^1$H NMR (400 MHz, DMSO-d$_6$): δ 10.2 (s, 1H), 10.1 (s, 1H), 8.18 (d, J=9.0 Hz, 2H), 7.80 (d, J=9.0 Hz, 2H), 7.38 (d, J=2.7 Hz, 1H), 7.14 (dd, J=8.6, 2.7 Hz, 1H), 6.71 (d, J=8.6 Hz, 1H), 1.77 (s, 2H), 1.68-1.46 (complex, 4H), 1.28 (s, 6H), 0.85 (t, J=7.4 Hz, 6H); $^{13}$C NMR (101 MHz, DMSO-d$_6$): δ 179.5, 150.0, 146.8, 142.5, 132.2, 131.9, 124.8, 123.8, 123.2, 121.8, 117.8, 79.1, 44.2, 33.2, 30.7, 29.1, 8.1. Anal. Calcd for C$_{22}$H$_{27}$N$_3$O$_3$S: C, 63.90; H, 6.58; N, 10.16. Found: C, 64.07; H, 6.64; N, 10.11.

1-(2,2-Diethyl-4,4-dimethylchroman-6-yl)-3-(4-nitrophenyl)urea (6b)

Compound 32 was converted to 6b using the general procedure described above. Yellow solid (145 mg, 85%), mp 190-192° C.; IR: 3333, 1662, 1556, 1331 cm$^{-1}$; $^1$H NMR (400 MHz, DMSO-d$_6$): δ 9.33 (s, 1H), 8.64 (s, 1H), 8.18 (d, J=8.9 Hz, 2H), 7.69 (d, J=8.9 Hz, 2H), 7.43 (d, J=2.7 Hz, 1H), 7.11 (dd, J=8.6, 2.7 Hz, 1H), 6.68 (d, J=8.6 Hz, 1H), 1.76 (s, 2H), 1.61 (m, 2H), 1.52 (m, 2H), 1.29 (s, 6H), 0.84 (t, J=7.4 Hz, 6H); $^{13}$C NMR (101 MHz, DMSO-d$_6$): δ 152.6, 148.1, 147.1, 141.2, 132.6, 132.3, 125.6, 119.2, 118.4, 118.0, 117.8, 78.8, 44.6, 33.1, 30.8, 29.1, 8.1. Anal. Calcd for C$_{22}$H$_{27}$N$_3$O$_4$.0.15 H$_2$O: C, 66.03; H, 6.88; N, 10.53. Found: C, 65.64; H, 6.68; N, 10.91.

1-(2,2-Diethyl-4,4-dimethylchroman-6-yl)-3-(4-(trifluoromethyl)phenyl)urea (6c)

White solid (166 mg, 92%), mp 208-210° C.; IR: 3326, 3202, 3142, 1659, 1323 cm$^{-1}$; $^1$H NMR (400 MHz, DMSO-d$_6$): δ 8.80 (s, 1H), 8.35 (s, 1H), 7.62 (d, J=8.4 Hz, 2H), 7.51 (d, J=8.4 Hz, 2H), 7.39 (s, 1H), 7.07 (d, J=8.6 Hz, 1H), 6.66 (d, J=8.6 Hz, 1H), 1.77 (s, 2H), 1.65 (m, 2H), 1.54 (m, 2H), 1.32 (s, 6H), 0.87 (t, J=7.3 Hz, 6H); $^{13}$C NMR (101 MHz, DMSO-d$_6$): δ 153.0, 148.1, 143.9, 132.5, 132.3, 126 (q, J=3.6 Hz), 124.6 (q, J=269.8 Hz), 122.5, 122.2, 118.7, 117.7, 117.6, 78.3, 44.0, 32.2, 30.0, 28.2, 7.1. Anal. Calcd for C$_{23}$H$_{27}$F$_3$N$_2$O$_2$: C, 65.70; H, 6.47; N, 6.66. Found: C, 65.94; H, 6.51; N, 6.67.

1-(4,4-Diethyl-2,2-dimethylchroman-6-yl)-3-(4-nitrophenyl)thiourea (7a)

Compound 40 was converted to 7a using the general procedure described above. Yellow solid (155 mg, 87%), mp 174-175° C.; IR: 3344, 3183, 3115, 1546, 1333, 1257 cm$^{-1}$; $^1$H NMR (400 MHz, DMSO-d$_6$): δ 10.2 (s, 1H), 10.1 (s, 1H), 8.19 (d, J=9.0 Hz, 2H), 7.81 (d, J=9.0 Hz, 2H), 7.30 (d, J=2.5 Hz, 1H), 7.12 (dd, J=8.6, 2.5 Hz, 1H), 6.71 (d, J=8.6 Hz, 1H), 1.75 (s, 2H), 1.70-1.54 (complex, 4H), 1.29 (s, 6H), 0.71 (t, J=7.3 Hz, 6H); $^{13}$C NMR (101 MHz, DMSO-d$_6$): δ 179.3, 151.6, 146.9, 142.5, 131.9, 130.1, 124.9, 123.8, 123.5, 121.6, 117.7, 74.7, 40.3, 37.6, 33.5, 29.1, 8.8. Anal. Calcd for C$_{22}$H$_{27}$N$_3$O$_3$S$_3$: C, 63.90; H, 6.58; N, 10.16. Found: C, 63.63; H, 6.53; N, 10.06.

1-(4,4-Diethyl-2,2-dimethylchroman-6-yl)-3-(4-(trifluoromethyl)phenyl)thiourea (7b)

White solid (159 mg, 85%), mp 155-156° C.; IR: 3360, 3154, 1302, 1162 cm$^{-1}$; NMR (400 MHz, DMSO-d$_6$): δ 9.95 (s, 1H), 9.87 (s, 1H), 7.72 (d, J=8.5 Hz, 2H), 7.65 (d, J=8.5 Hz, 2H), 7.28 (d, J=2.5 Hz, 1H), 7.10 (dd, J=8.5, 2.5 Hz, 1H), 6.69 (d, J=8.5 Hz, 1H), 1.75 (s, 2H), 1.61 (m, 4H), 1.29 (s, 6H), 0.72 (t, J=7.2 Hz, 6H); $^{13}$C NMR (101 MHz, DMSO-d$_6$): δ 179.9, 151.4, 143.9, 132.1, 130.0, 126.0 (q, J=3.4 Hz), 124.9 (q, J=271.2 Hz), 124.2, 123.8, 123.6, 122.9, 117.6, 74.6, 37.5, 33.5, 29.1, 8.8 (one aliphatic carbon obscured by solvent). Anal. Calcd for C$_{23}$H$_{27}$F$_3$N$_2$OS: C, 63.28; H, 6.23; N, 6.42. Found: C, 63.38; H, 6.21; N, 6.40.

1-(4,4-Diethyl-2,2-dimethylchroman-6-yl)-3-(4-nitrophenyl)urea (7c)

Compound 33 was converted to 7c using the general procedure described above. Yellow solid (150 mg, 88%), mp 228-229° C.; IR: 3292, 3154, 3098, 1652, 1559, 1332 cm$^{-1}$; NMR (400 MHz, DMSO-d$_6$): δ 9.34 (s, 1H), 8.67 (s, 1H), 8.18 (d, J=9.0 Hz, 2H), 7.68 (d, J=9.0 Hz, 2H), 7.37 (d, J=2.5 Hz, 1H), 7.09 (dd, J=8.6, 2.5 Hz, 1H), 6.67 (d, J=8.6 Hz, 1H), 1.74 (s, 2H), 1.72-1.55 (complex, 4H), 1.28 (s, 6H), 0.73 (t, J=7.3 Hz, 6H); $^{13}$C NMR (101 MHz, DMSO-d$_6$) δ 152.5, 149.7, 147.1, 141.2, 132.2, 130.4, 125.6, 118.8, 118.3, 117.9, 117.8, 74.3, 40.1, 37.6, 33.6, 29.0, 8.8. Anal. Calcd for C$_{22}$H$_{27}$N$_3$O$_4$: C, 66.48; H, 6.85; N, 10.57. Found: C, 66.22; H, 6.86; N, 10.37.

1-(4,4-Diethyl-2,2-dimethylchroman-6-yl)-3-(4-(trifluoromethyl)phenyl)urea (7d)

White solid (164 mg, 91%), mp 225-226° C.; IR: 3312, 3169, 1652, 1554, 1328 cm$^{-1}$; $^1$H NMR (400 MHz, DMSO-d$_6$): δ 8.98 (s, 1H), 8.54 (s, 1H), 7.65 (d, J=8.9 Hz, 2H), 7.61 (d, J=8.9 Hz, 2H), 7.35 (d, J=2.7 Hz, 1H), 7/08 (dd, J=8.6, 2.7 Hz, 1H), 6.66 (d, J=8.6 Hz, 1H), 1.74 (s, 2H), 1.68-1.54 (complex, 4H), 1.27 (s, 6H), 0.73 (t, J=7.3 Hz, 6H); $^{13}$C NMR (101 MHz, DMSO-d$_6$): δ 152.9, 149.4, 144.2, 132.5, 130.3, 126.5 (q, J=4.0 Hz), 125.1 (q, J=270.0 Hz), 122.0, 121.7, 118.6, 118.1, 117.8, 74.3, 37.6, 33.6, 29.0, 8.8 (one aliphatic carbon obscured by solvent). Anal. Calcd for C$_{23}$H$_{27}$F$_3$N$_2$O$_2$: C, 65.70; H, 6.47; N, 6.66. Found: C, 65.55; H, 6.44; N, 6.61.

1-(4-Nitrophenyl)-3-(2,2,4,4-tetraethylchroman-6-yl)thiourea (8a)

Compound 46 was converted to 8a using the general procedure described above. Light yellow solid (162 mg, 85%), mp 162-164° C. IR: 3339, 3178, 1512, 1336 cm$^{-1}$; $^1$H NMR (400 MHz, CDCl$_3$): δ 8.20 (d, J=8.8 Hz, 2H), 8.05 (br s, 1H), 7.75 (coincident d, J=8.9 Hz, 2H and br s, 1H), 7.11 (d, J=2.1 Hz, 1H), 7.03 (dd, J=8.4, 2.1 Hz, 1H), 6.91 (d, J=8.4 Hz, 1H), 1.78 (s, 2H), 1.78-1.55 (complex, 8H), 0.91 (t, J=7.4 Hz, 6H), 0.77 (t, J=7.3 Hz, 6H); $^{13}$C NMR (101 MHz, CDCl$_3$): δ 179.4, 154.6, 144.4, 144.0, 133.4, 127.3, 125.2, 124.9, 124.5, 122.6, 119.8, 80.0, 37.6, 36.2, 33.4, 29.9, 8.5, 7.8. Anal. Calcd for C$_{24}$H$_{31}$N$_3$O$_3$S.0.2H$_2$O: C, 64.75; H, 7.11; N, 9.44. Found: C, 64.75; H, 7.12; N, 9.36.

1-(4-Nitrophenyl)-3-(2,2,4,4-tetraethylchroman-6-yl)urea (8b)

Compound 46 was converted to 8b using the general procedure described above. Light yellow solid (148 mg, 91%), mp 163-164° C.; IR: 3342, 3220, 3158, 3098, 1662, 1512, 1336 cm$^{-1}$; $^1$H NMR (400 MHz, DMSO-d$_6$): δ 9.34 (s, 1H), 8.67 (s, 1H), 8.18, J=9.1 Hz, 2H), 7.69 (d, J=9.1 Hz, 2H), 7.36 (d, J=2.6 Hz, 1H), 7.10 (dd, J=8.6, 2.5 Hz, 1H), 6.69 (d, J=8.6 Hz, 1H), 1.70 (s, 2H), 1.72-1.43 (complex, 8H), 0.83 (t, J=7.3 Hz, 6H), 0.73 (t, J=7.3 Hz, 6H); $^{13}$C NMR (101 MHz, DMSO-d$_6$): δ 152.5, 149.6, 147.1, 141.2, 132.3, 131.3, 125.6, 118.7, 118.2, 118.0, 117.7, 78.8, 37.5, 36.9, 33.5, 29.6, 8.7, 8.0. Anal. Calcd for C$_{24}$H$_{31}$N$_3$O$_4$: C, 67.74; H, 7.34; N, 9.88. Found: C, 67.59; H, 7.35; N, 9.83.

1-(2,2,4,4-Tetraethylchroman-6-yl)-3-(4-(trifluoromethyl)phenyl)urea (8c)

White solid (176 mg, 91%), mp 165-166° C.; IR: 3309, 3203, 3142, 3095, 1655, 1327 cm$^{-1}$; $^1$H NMR (400 MHz, DMSO-d$_6$): δ 8.98 (s, 1H), 8.54 (s, 1H), 7.65 (d, J=8.7 Hz, 2H), 7.61 (d, J=8.8 Hz, 2H), 7.34 (d, J=1.3 Hz, 1H), 7.08 (dd, J=8.6, 1.3 Hz, 1H), 6.68 (d, J=8.6 Hz, 1H), 1.70 (s, 2H), 1.70-1.43 (complex, 8H), 0.83 (t, J=7.3 Hz, 6H), 0.72 (t, J=7.3 Hz, 6H); $^{13}$C NMR (101 MHz, DMSO-d$_6$): δ 151.9, 148.3, 143.1, 131.5, 130.2, 125.4 (q, J=3.5 Hz), 124.8 (q, J=270.9 Hz), 120.7 (q, J=31.9 Hz), 117.5, 117.1, 117.0, 116.9, 77.7, 36.4, 36.0, 32.5, 28.6, 7.7, 7.0. Anal. Calcd for C$_{25}$H$_{31}$F$_3$N$_2$O$_2$: C, 66.95; H, 6.97; N, 6.25. Found: C, 66.94; H, 6.98; N, 6.18.

1-(2,2,4,4-Tetraethylchroman-6-yl)-3-(4-(trifluoromethoxy)phenyl)urea (8d)

White solid (156 mg, 78%), mp 180-181° C.; IR: 3295, 3201, 1645, 1267 cm$^{-1}$; $^1$H NMR (400 MHz, DMSO-d$_6$): δ 8.75 (s, 1H), 8.46 (s, 1H), 7.55 (d, J=8.9 Hz, 2H), 7.32 (d, J=2.5 Hz, 1H), 7.26 (d, J=8.8 Hz, 2H), 7.08 (dd, J=8.6, 2.5 Hz, 1H), 6.67 (d, J=8.6 Hz, 1H), 1.70 (s, 2H), 1.70-1.43 (complex, 8H), 0.83 (t, J=7.4 Hz, 6H), 0.72 (t, J=7.3 Hz, 6H); $^{13}$C NMR (101 MHz, DMSO-d$_6$): δ 151.2, 148.2, 141.8, 138.7, 131.8, 130.2, 121.1, 119.6 (q, J=255.1 Hz), 118.6, 117.3, 116.83, 116.82, 77.6, 36.4, 35.9, 32.5, 28.6, 7.7, 7.0. Anal. Calcd for C$_{25}$H$_{31}$F$_3$N$_2$O$_3$: C, 64.64; H, 6.73; N, 6.03. Found: C, 64.38; H, 6.66; N, 5.98.

The following analyses pertain to compounds Scheme 9, Scheme 10, Scheme 11 and Scheme 12.

General Procedure for the Preparation of 9 and 10.

Members of 9 and 10 utilized 4-bromoaniline (47) as the starting material followed by the individual steps shown. The sequence of 47→48→49→50→51→52→53→54→9→10 are not known by prior art, and exact conditions for each step herein were critical to obtain each new compound in pure form. To a stirred solution of 53 (0.2 g, 0.7 mmol) in THF (5 mL) was added various iso(thio)cyanates (0.7 mmol) in THF (2 mL) dropwise at room temperature. The mixture was stirred until the TLC analysis indicated that 53 was completely consumed. The solvent was evaporated under vacuum to give the Boc-protected urea and (thio)urea derivatives 54a-d. To the resulting Boc-protected compound in dichloromethane (DCM, 5 mL) was slowly added trifluoroacetic acid (200 μL, 2.6 mmol), and the mixture was stirred until TLC indicated the absence of 9a-d. The solvent was removed under vacuum. Two additional portions of DCM (2×10 mL) were added and removed under vacuum. Water (20 mL) was added to the resulting residue, and the mixture was washed with ether (2×20 mL). The aqueous layer was basified using NaHCO$_3$ powder and extracted with EtOAc (3×20 mL). Combined organic extracts were washed with water (2×20 mL), saturated NaCl (20 mL), dried (MgSO$_4$), filtered and concentrated under vacuum. Recrystallization of the products from pentane/ether (3:7) afforded pure 9a-d. All members of 9 were solids with sharp melting points and gave the expected structural data from IR, NMR, and elemental analyses. Compound 9 was N-methylated to give salt 10.

1-(4,4-Dimethyl-1,2,3,4-tetrahydroquinolin-6-yl)-3-(4-nitrophenyl)urea (9a)

Yield: 153 mg (0.45 mmol, 64%) as a yellow solid, mp 219-220° C.; IR (nujol): 1698, 1548, 1180, 851 cm$^{-1}$; $^1$H NMR (400 MHz, DMSO-d$_6$): δ 9.23 (s, 1H), 8.36 (s, 1H), 8.16 (d, J=8.9 Hz, 2H), 7.66 (d, J=8.9 Hz, 2H), 7.18 (s, 1H), 6.91 (d, J=8.5 Hz, 1H), 6.39 (d, J=8.5 Hz, 1H), 5.54 (s, 1H), 3.16 (s, 2H), 1.61 (s, 2H), 1.22 (s, 6H); $^{13}$C NMR (101 MHz, DMSO-d$_6$): δ 152.6, 147.4, 141.0, 129.4, 127.6, 125.6 (2C), 119.5, 118.7, 117.6, 114.1, 37.8, 37.3, 31.9, 31.3. Anal. Calcd. for C$_{18}$H$_{20}$N$_4$O$_3$: C, 63.52; H, 5.92; N, 16.46. Found: C, 63.36; H, 6.08; N, 16.51.

1-(4,4-Dimethyl-1,2,3,4-tetrahydroquinolin-6-yl)-3-(4-nitrophenyl)thiourea (9b)

Yield: 164 mg (0.46 mmol, 66%) as a red solid, mp 150-152° C.; IR (nujol): 3333, 1509, 1334, 1263 cm$^{-1}$; $^1$H NMR (400 MHz, CDCl$_3$): δ 8.19 (d, J=8.6 Hz, 2H), 7.78 (d, J=8.6 Hz, 2H), 7.71 (obscured signal, 2H), 7.09 (s, 1H), 6.88 (d, J=8.3 Hz, 1H), 6.50 (d, J=8.3 Hz, 1H), 4.19 (br s, 1H), 3.39-3.36 (m, 2H), 1.76-1.74 (m, 2H), 1.30 (s, 6H); $^{13}$C NMR (101 MHz, CDCl$_3$): δ 179.5, 144.28, 144.25, 144.1, 131.6, 125.1, 124.8, 124.4, 123.3, 122.7, 114.9, 38.2, 36.2, 32.0, 30.6: Anal. Calcd. for C$_{18}$H$_{20}$N$_4$O$_2$S: C, 60.65; H, 5.65; N, 15.72. Found: C, 60.53; H, 5.82; N, 15.87.

1-(4,4-Dimethyl-1,2,3,4-tetrahydroquinolin-6-yl)-3-(4-(trifluoromethyl)phenyl)thiourea (9c)

Yield: 169 mg (0.44 mmol, 63%) as a yellow solid, mp 104-105° C.; IR (nujol): 3346, 1512, 1324 cm$^{-1}$; $^1$H NMR (400 MHz, CDCl$_3$): δ 7.67 (br s, 1H), 7.65 (d, J=8.9 Hz, 2H), 7.58 (d, J=8.9 Hz, 2H and s, 1H), 7.11 (d, J=2.4 Hz, 1H), 6.89 (dd, J=8.4, 2.4 Hz, 1H), 6.49 (d, J=8.4 Hz, 1H), 4.02 (br s, 1H), 3.36 (t, J=5.9 Hz, 2H), 1.75 (t, J=5.9 Hz, 2H), 1.29 (s, 6H); $^{13}$C NMR (101 MHz, CDCl$_3$): δ 180.1, 143.9, 141.4, 131.5, 127.4 (q, J=32.9 Hz), 125.9 (br), 125.2, 124.9, 123.9 (q, J=271.5 Hz), 123.8, 114.8, 38.9, 36.3, 32.0, 30.6 (1 aromatic C unresolved). Anal. Calcd. for C$_{19}$H$_{20}$F$_3$N$_3$S: C, 60.14; H, 5.31; N, 11.07. Found: C, 60.28; H, 5.12; N, 11.28.

1-(4,4-Dimethyl-1,2,3,4-tetrahydroquinolin-6-yl)-3-(4-(trifluoromethoxy)phenyl)thiourea (9d)

Yield: 164 mg (0.42 mmol, 60%) as a yellow solid, mp 69-71° C.; IR (nujol): 3348, 3186, 1509, 1257 cm$^{-1}$; $^1$H NMR (400 MHz, CDCl$_3$): δ 7.69 (br s, 1H), 7.49 (d, J=9.0 Hz, 2H and s, 1H), 7.18 (d, J=9.0 Hz, 2H), 7.11 (d, J=2.4 Hz, 1H), 6.89 (dd, J=8.0, 2.4 Hz, 1H), 6.48 (d, J=8.0 Hz, 1H), 4.20 (br s, 1H), 3.35 (t, J=5.5 Hz, 2H), 1.74 (t, J=5.5 Hz, 2H), 1.29 (s, 6H); $^{13}$C NMR (101 MHz, CDCl$_3$): δ 180.4, 146.7, 143.8, 136.8, 131.4, 126.1, 125.2, 124.9, 124.0 (br), 121.3, 120.4 (q, J=257.4 Hz), 114.8, 38.2, 36.3, 31.9, 30.7. Anal. Calcd. for C$_{19}$H$_{20}$F$_3$N$_3$OS: C, 57.71; H, 5.10; N, 10.63. Found: C, 57.56; H, 5.23; N, 10.37.

1,1,4,4-Tetramethyl-6-(3-(4-nitrophenyl)ureido)-1,2,3,4-tetrahydroquinolin-1-ium Iodide (10)

To a stirred solution of 9a (0.2 g, 0.6 mmol) in DMF (5 mL) in a 15 mL Chemglass pressure vessel (No. CG-1880-01) was added Cs$_2$CO$_3$ (390 mg, 1.2 mmol) and methyl iodide (1.0 mL, 16.0 mmol). The vessel was closed, and the reaction was stirred at room temperature for 24 h. Water (5 mL) was added and the solid was filtered. The crude solid was stirred with ethanol (10 mL) for 15 min and filtered to provide 10 as a yellow solid (185 mg, 0.37 mmol, 62%), mp 249-251° C.; IR: 3297, 3260, 1724, 1598, 843 cm$^{-1}$; $^1$H NMR (400 MHz, DMSO-d$_6$): δ 9.59 (s, 1H), 9.21 (s, 1H), 8.21 (d, J=8.9 Hz, 2H), 7.88 (d, J=9.2 Hz, 1H), 7.71 (d, J=8.9 Hz, 2H), 7.67 (s, 1H), 7.51 (d, J=9.2 Hz, 1H), 3.89 (m, 2H), 3.56 (s, 6H), 2.11 (m, 2H), 1.36 (s, 6H); $^{13}$C NMR (101 MHz, CDCl$_3$): δ 151.4, 145.4, 140.7, 139.7, 139.4, 135.0, 124.5, 121.3, 117.4, 117.2, 116.7, 59.4, 56.1, 31.6, 30.5, 26.8: Anal. Calcd. for C$_{20}$H$_{25}$IN$_4$O$_3$: C, 48.40; H, 5.08; N, 11.29. Found: C, 48.65; H, 5.23; N, 11.52.

General Procedure for the Preparation of Members of 11.

An entry to members of 11 is delineated in Scheme 10. A modified Skraup reaction on 4-bromoaniline with acetone and bismuth(III) trifluoromethanesulfonate gave the dihydroquinoline 55 (62%). A solution of 55 in DMF was carefully treated with a 4-fold excess of methyl iodide in DMF at 15° C. and was allowed to warm slowly to room temperature. Stirring for an additional 18 hours generated 56 (82%). Alcohol 57 (57%) was realized by hydroboration of the double bond in 56. Oxidation 57 via a Swern procedure led to the tetrahydroquinolinone 58, which was immediately alkylated to 59 (62%). Utilizing a pressure vessel, a mixture of 59, copper(I) iodide, L-proline, DMF and aq. ammonia was heated to produce aniline 60 (65%). A series of isocyanates and isothiocyanates were added to 60, leading to solid derivatives 11 (60-78%) which were purified by chromatography and crystallized from ether:pentane (3:7). All members of 11 gave the correct IR, NMR, and elemental analyses.

1-(4-Nitrophenyl)-3-(1,2,2,4,4-pentamethyl-3-oxo-1,2,3,4-tetrahydroquinolin-6-yl)urea (11a)

Yield: 0.25 g (0.64 mmol, 74%) as an orange solid, mp 200-201° C.; IR (nujol): 1718, 1655, 1556 cm$^{-1}$; $^1$H NMR (400 MHz, DMSO-d$_6$): δ 9.35 (s, 1H), 8.73 (s, 1H), 8.18 (d, J=8.0 Hz, 2H), 7.68 (d, J=8.0 Hz, 2H), 7.35 (s, 1H), 7.31 (d, J=8.8 Hz, 1H), 6.82 (d, J=8.6 Hz, 1H), 2.79 (s, 3H), 1.39 (s, 6H), 1.20 (s, 6H); $^{13}$C NMR (101 MHz, DMSO-d$_6$): δ 213.6, 151.5, 146.0, 140.4, 140.2, 131.1, 129.6, 124.5, 118.2, 116.7, 115.4, 113.7, 63.1, 46.5, 30.2, 22.2, 22.1. Anal. Calcd. for C$_{21}$H$_{24}$N$_4$O$_4$: C, 63.62; H, 6.10; N, 14.13. Found: C, 63.39; H, 6.26; N, 14.27.

1-(4-Nitrophenyl)-3-(1,2,2,4,4-pentamethyl-3-oxo-1,2,3,4-tetrahydroquinolin-6-yl)thiourea (11b)

Yield: 0.23 g (0.56 mmol, 65%) as a yellow solid, mp 145-147° C.; IR (nujol): 3308, 1715, 1532, 1498, 1332 cm$^{-1}$; $^1$H NMR (400 MHz, CDCl$_3$): δ 8.20 (d, J=8.7 Hz, 2H), 7.83 (s, 1H), 7.75 (d, J=8.7 Hz, 2H), 7.69 (s, 1H), 7.21 (dd, J=8.6, 2.4 Hz, 1H), 7.14 (d, J=2.4 Hz, 1H), 6.88 (d, J=8.5 Hz, 1H), 2.91 (s, 3H), 1.45 (s, 6H), 1.32 (s, 6H); $^{13}$C NMR (101 MHz, CDCl$_3$): δ 213.6, 179.4, 145.7, 144.5, 144.0, 132.7, 127.0, 125.7, 124.5, 123.0, 122.8, 115.1, 64.4, 47.7, 31.1, 23.7, 23.0. Anal. Calcd. for C$_{21}$H$_{24}$N$_4$O$_3$S: C, 61.15; H, 5.86; N, 13.58. Found: C, 61.38; H, 5.52; N, 13.37.

1-(1,2,2,4,4-Pentamethyl-3-oxo-1,2,3,4-tetrahydroquinolin-6-yl)-3-(4-(trifluoromethyl)phenyl)urea (11c)

Yield: 0.28 g (0.67 mmol, 78%) as a brown solid, mp 198-199° C.; IR (nujol): 3328, 1720, 1656 cm$^{-1}$; $^1$H NMR (400 MHz, DMSO-d$_6$): δ 8.78 (s, 1H), 8.52 (s, 1H), 7.54 (d, J=8.5 Hz, 2H), 7.32-7.24 (complex, 4H), 6.79 (d, J=8.6 Hz, 1H), 2.82 (s, 3H), 1.38 (s, 6H), 1.19 (s, 6H); $^{13}$C NMR (CDCl$_3$): δ 213.6, 151.8, 143.1, 140.1, 131.4, 129.6, 125.4 (q, J=3.5 Hz), 124.1 (q, J=272.5 Hz), 120.8 (q, J=32.0 Hz), 118.1, 117.1, 115.3, 113.7, 63.1, 46.5, 30.2, 22.2. Anal.

Calcd. for $C_{22}H_{24}F_3N_3O_2$: C, 63.00; H, 5.77; N, 10.02. Found: C, 63.12; H, 5.59; N, 10.29.

1-(1,2,2,4,4-Pentamethyl-3-oxo-1,2,3,4-tetrahydroquinolin-6-yl)-3-(4-trifluoromethyl)phenyl)thiourea (11d)

Yield: 0.25 g (0.58 mmol, 67%) as a brown solid, mp 149-151° C.; IR (nujol): 3291, 3206, 1716, 1615, 1324 cm$^{-1}$; $^1$H NMR (400 MHz, CDCl$_3$): δ 7.88 (s, 1H), 7.65 (s, 1H), 7.61 (d, J=9.1 Hz, 2H), 7.59 (d, J=9.1 Hz, 2H), 7.22 (dd, J=8.5, 2.6 Hz, 1H), 7.15 (d, J=2.4 Hz, 1H), 6.86 (d, J=8.5 Hz, 1H), 2.90 (s, 3H), 1.48 (s, 6H), 1.32 (s, 6H); $^{13}$C NMR (101 MHz, CDCl$_3$): δ 214.0, 179.8, 145.3, 141.1, 132.3, 127.8 (q, J=32.6 Hz), 127.7 (br), 126.1 (q, J=2.7 Hz), 125.6, 124.1, 123.9 (q, J=272.0 Hz), 122.7, 115.0, 64.4, 47.6, 31.1, 23.6, 23.0. Anal. Calcd. for $C_{22}H_{24}F_3N_3OS$: C, 60.67; H, 5.55; N, 13.09. Found: C, 60.94; H, 5.23; N, 13.28.

1-(1,2,2,4,4-Pentamethyl-3-oxo-1,2,3,4-tetrahydroquinolin-6-yl)-3-(4-(trifluoromethoxy)phenyl)urea (11e)

Yield: 0.27 g (0.62 mmol, 72%) as a brown solid, mp 191-192° C.; IR (nujol): 3318, 1716, 1648 cm$^{-1}$; $^1$H NMR (400 MHz, DMSO-d$_6$): δ 9.01 (s, 1H), 8.61 (s, 1H), 7.65 (d, J=8.8 Hz, 2H), 7.61 (d, J=8.8 Hz, 2H), 7.32 (d, J=2.4 Hz, 1H), 7.30 (dd, J=8.5, 2.4 Hz, 1H), 6.80 (d, J=8.6 Hz, 1H), 2.79 (s, 3H), 1.39 (s, 6H), 1.19 (s, 6H); $^{13}$C NMR (101 MHz, DMSO-d$_6$): δ 213.7, 152.1, 141.8, 140.0, 138.7, 131.6, 129.6, 121.1, 119.6 (q, J=255.2 Hz), 118.6, 117.9, 115.2, 113.7, 63.1, 46.5, 30.2, 22.1. Anal. Calcd. for $C_{22}H_{24}F_3N_3O_3$: C, 60.68; H, 5.56; N, 9.65. Found: C, 60.79; H, 5.76; N, 9.83.

1-(1,2,2,4,4-Pentamethyl-3-oxo-1,2,3,4-tetrahydroquinolin-6-yl)-3-(4-(trifluoromethoxy)phenyl)thiourea (11f)

Yield: 0.24 g (0.52 mmol, 60%) as a brown solid; mp 83-85° C.; IR (nujol): 3291, 3213, 1716, 1501 cm$^{-1}$; $^1$H NMR (400 MHz, DMSO-d$_6$): δ 9.76 (s, 1H), 9.72 (s, 1H), 7.56 (d, J=8.8 Hz, 2H), 7.30 (coincident d, J=8.8 Hz, 2H and dd, J=8.7, 2.1 Hz, 1H), 7.24 (d, J=2.1 Hz, 1H), 6.83 (d, J=8.7 Hz, 1H), 2.81 (s, 3H), 1.37 (s, 6H), 1.21 (s, 6H); $^{13}$C NMR (101 MHz, DMSO-d$_6$): δ 213.5, 178.9, 143.8, 142.0, 138.3, 130.8, 129.1, 124.6, 123.3, 120.5, 120.2, 119.5 (q, J=255.7 Hz), 113.3, 63.2, 46.4, 30.3, 22.4, 22.1. Anal. Calcd. for $C_{22}H_{24}F_3N_3O_2S$: C, 58.52; H, 5.36; N, 9.31. Found: C, 58.29; H, 5.12; N, 9.07.

1-(4-Aminophenyl)-3-(1,2,2,4,4-pentamethyl-3-oxo-1,2,3,4-tetrahydroquinolin-6-yl)urea (11g)

To a stirred suspension of 11a (120 mg, 0.30 mmol) and iron powder (106 mg, 1.88 mmol) in ethanol:water (4:1, 6.0 mL) was added NH$_4$Cl (48 mg, 0.90 mmol), and the resulting mixture was refluxed for 12 h. The reaction was cooled and filtered through CELITE®. The CELITE was washed with ethanol (3×5 mL) and the filtrate was concentrated under vacuum at 45° C. to give a brown solid. Recrystallization of the solid from ether-pentane gave pure 11g (92 mg (0.25 mmol, 84%) as a brown solid, mp 135-137° C.; IR (nujol): 3297, 1713, 1642, 1601, 1502 cm$^{-1}$; $^1$H NMR (400 MHz, DMSO-d$_6$): δ 8.26 (s, 1H), 8.00 (s, 1H), 7.38-7.22 (complex, 2H), 7.05 (d, J=8.2 Hz, 2H), 6.76 (d, J=8.6 Hz, 1H), 6.50 (d, J=8.2 Hz, 2H), 4.76 (br s, 2H), 2.77 (s, 3H), 1.37 (s, 6H), 1.18 (s, 6H); $^{13}$C NMR (101 MHz, DMSO-d$_6$): δ 213.8, 152.6, 143.2, 139.5, 132.4, 129.5, 128.2, 120.0, 117.4, 114.7, 113.7, 113.5, 63.1, 46.5, 30.2, 22.2, 22.1. Anal. Calcd. for $C_{21}H_{26}N_4O_2$: C, 68.83; H, 7.15; N, 15.29. Found: C, 68.66; H, 7.26; N, 15.07.

General Procedure for the Preparation of 12 (Scheme 11).

The reaction pathway and intermediates leading to 69 are reasonable to those versed in the art of synthesis, although the reaction conditions for the conversions are crucial. The general procedure to obtain members of 12 are as follows. To a stirred solution of 69 (0.11 g, 0.50 mmol) in THF (5 mL) was added dropwise two isothiocyanates (0.86 mmol) in THF (2 mL) at room temperature under a nitrogen atmosphere. The reaction was stirred until TLC analysis indicated the complete consumption of 69. The solvent was evaporated under vacuum, the residue was purified by column chromatography (20-40% ether in hexanes gradient), and the product was crystallized from ether in pentane (3:7) to afford 12. Both isomers were solids and gave the correct IR, NMR, and elemental analyses.

3-(1,2,2,4,4-Pentamethyl-1,2,3,4-tetrahydroquinolin-6-yl)-1-(4-nitrophenyl)thiourea (12)

Yield: 0.18 g, (0.45 mmol, 90%) as an orange solid, mp 151-153° C.; IR: 3335, 1596, 1500, 1332, 1263, 851 cm$^{-1}$; $^1$H NMR (400 MHz, CDCl$_3$): δ 8.17 (d, J=9.3 Hz, 2H), 7.97 (s, 1H), 7.78 (d, J=8.8 Hz, 2H and s, 1H), 7.08 (d, J=2.2 Hz, 1H), 7.02 (dd, J=8.8, 2.2 Hz, 1H), 6.63 (d, J=8.8 Hz, 1H), 2.83 (s, 3H), 1.82 (s, 2H), 1.32 (s, 6H), 1.29 (s, 6H); $^{13}$C NMR (101 MHz, CDCl$_3$): δ 179.4, 145.6, 144.34, 144.25, 135.4, 124.9, 124.4, 123.2 (br), 123.1, 122.7, 112.8, 54.6, 52.0, 31.51, 31.45, 31.0, 28.0. Anal. Calcd. for $C_{21}H_{26}N_4O_2S$: C, 63.28; H, 6.57; N, 14.06. Found: C, 63.06; H, 6.58; N, 13.92.

General Procedure for the Preparation of Members of 13

To a stirred solution of 60 (0.2 g, 0.86 mmol) in THF (10 mL) was added portion-wise lithium aluminum hydride (65.0 mg, 1.72 mmol) at 0° C. The reaction was stirred at room temperature for 4 h, quenched with saturated Na$_2$SO$_4$ at 0° C., filtered through CELITE and extracted with EtOAc (20 mL). The organic layer was washed with water, saturated NaCl, dried (Na$_2$SO$_4$), filtered and concentrated to give 70 as a brown oil. The residue was dissolved in THF (5 mL) and the solution was added dropwise at room temperature to an isocyanate or isothiocyanate (0.86 mmol) in THF. When TLC analysis indicated the disappearance of 60, the reaction mixture was concentrated under vacuum and purified by column chromatography (EtOAc in hexanes gradient). Concentration of the major fraction and crystallization from a DCM/ether mixture (2:8) afforded 13a-f all of which were solids and gave the appropriate IR, NMR, and elemental analyses as well as displaying sharp melting points.

1-(3-Hydroxy-1,2,2,4,4-pentamethyl-1,2,3,4-tetrahydroquinolin-6-yl)-3-(4-nitrophenyl)urea (13a)

Yield: 0.27 g (0.69 mmol, 80%) as a yellow solid, mp 215-217° C.; IR (nujol): 3473, 3251, 1659, 1556 cm$^{-1}$; $^1$H NMR (400 MHz, DMSO-d$_6$): δ 9.27 (s, 1H), 8.51 (s, 1H), 8.17 (d, J=8.8 Hz, 2H), 7.67 (d, J=8.8 Hz, 2H), 7.27 (s, 1H), 7.11 (d, J=8.6 Hz, 1H), 6.51 (d, J=8.8 Hz, 1H), 5.17 (d, J=6.4 Hz, 1H), 3.23 (d, J=6.4 Hz, 1H), 2.71 (s, 3H), 1.26 (s, 3H), 1.23 (s, 3H), 1.16 (s, 3H), 1.06 (s, 3H); $^{13}$C NMR (101 MHz, DMSO-d$_6$): δ 151.5, 146.2, 140.0, 139.8, 132.1, 128.0, 124.5, 117.9, 117.1, 116.5, 111.4, 78.2, 57.7, 37.2, 30.9, 28.8, 26.5, 22.9, 17.6. Anal. Calcd. for $C_{21}H_{26}N_4O_4$: C, 63.30; H, 6.58; N, 14.06. Found: C, 63.62; H, 6.81; N, 14.16.

1-(3-Hydroxy-1,2,2,4,4-pentamethyl-1,2,3,4-tetrahydroquinolin-6-yl)-3-(4-nitrophenyl)thiourea (13b)

Yield: 0.22 g (0.53 mmol, 62%) as a yellow solid, mp 161-163° C.; IR (nujol): 3444, 1645, 1377 cm$^{-1}$; $^1$H NMR (400 MHz, DMSO-d$_6$): δ 10.1 (s, 1H), 10.0 (s, 1H), 8.17 (d, J=8.7 Hz, 2H), 7.81 (d, J=8.7 Hz, 2H), 7.23 (s, 1H), 7.13 (d, J=8.7 Hz, 1H), 6.54 (d, J=8.8 Hz, 1H), 5.21 (d, J=6.3 Hz, 1H), 3.23 (d, J=6.4 Hz, 1H), 2.74 (s, 3H), 1.25 (s, 6H), 1.15 (s, 3H), 1.09 (s, 3H); $^{13}$C NMR (101 MHz, DMSO-d$_6$): δ 177.9, 146.0, 141.4, 141.3, 131.5, 127.4, 123.7, 122.2, 121.3, 120.5, 110.9, 77.9, 57.9, 37.1, 31.0, 28.5, 26.8, 22.9, 17.9. Anal. Calcd. for $C_{21}H_{26}N_4O_3S$: C, 60.85; H, 6.32; N, 13.52. Found: C, 60.58; H, 6.42; N, 13.71.

1-(3-Hydroxy-1,2,2,4,4-pentamethyl-1,2,3,4-tetrahydroquinolin-6-yl)-3-(4-(trifluoromethyl)phenyl)urea (13c)

Yield: 0.26 g (0.61 mmol, 71%) as a brown solid; mp 213-215° C.; IR (nujol): 3308, 1647, 1605 cm$^{-1}$; $^1$H NMR (400 MHz, DMSO-d$_6$): δ 8.92 (s, 1H), 8.38 (s, 1H), 7.64 (d, J=8.7 Hz, 2H), 7.60 (d, J=8.7 Hz, 2H), 7.25 (d, J=2.3 Hz, 1H), 7.10 (dd, J=8.7, 2.3 Hz, 1H), 6.50 (d, J=8.7 Hz, 1H), 5.16 (d, J=6.4 Hz, 1H), 3.22 (d, J=6.4 Hz, 1H), 2.70 (s, 3H), 1.26 (s, 3H), 1.22 (s, 3H), 1.16 (s, 3H), 1.06 (s, 3H); $^{13}$C NMR (101 MHz, DMSO-d$_6$): δ151.9, 143.3, 139.6, 132.1, 128.4, 125.4 (q, J=4.4 Hz), 124.0 (q, J=271.3 Hz), 120.6 (q, J=31.9 Hz), 117.7, 117.0, 116.9, 111.4, 78.2, 57.7, 37.2, 30.9, 28.8, 26.5, 22.9, 17.6. Anal. Calcd. for $C_{22}H_{26}F_3N_3O_2$: C, 62.70; H, 6.22; N, 9.97. Found: C, 62.58; H, 6.48; N, 10.12.

1-(3-Hydroxy-1,2,2,4,4-pentamethyl-1,2,3,4-tetrahydroquinolin-6-yl)-3-(4-(trifluoromethyl)phenyl)thiourea (13d)

Yield: 0.23 g (0.52 mmol, 60%) as a brown solid, mp 105-107° C.; IR (nujol): 3345, 1615, 1501 cm$^{-1}$; $^1$H NMR (400 MHz, DMSO-d$_6$): δ 9.79 (s, 2H), 7.73 (d, J=8.5 Hz, 2H), 7.64 (d, J=8.5 Hz, 2H), 7.20 (s, 1H), 7.11 (d, J=8.7 Hz, 1H), 6.53 (d, J=8.7 Hz, 1H), 5.20 (d, J=6.4 Hz, 1H), 3.23 (d, J=6.4 Hz, 1H), 2.74 (s, 3H), 1.25 (s, 3H), 1.24 (s, 3H), 1.15 (s, 3H), 1.09 (s, 3H); $^{13}$C NMR (101 MHz, DMSO-d$_6$): δ 178.4, 143.1, 141.3, 131.5, 127.6, 124.8 (q, J=3.6 Hz), 123.9 (q, J=252.2 Hz), 122.8 (q, J=32.0 Hz), 122.4, 121.9, 121.5, 110.9, 77.9, 57.9, 37.1, 31.0, 28.5, 26.8, 22.9, 17.8. Anal. Calcd. for $C_{22}H_{26}F_3N_3OS$: C, 60.39; H, 5.99; N, 9.60. Found: C, 60.28; H, 6.12; N, 9.47.

1-(3-Hydroxy-1,2,2,4,4-pentamethyl-1,2,3,4-tetrahydroquinolin-6-yl)-3-(4-(trifluoromethoxy)phenyl)urea (13e)

Yield: 0.25 g (0.57 mmol, 66%) as a brown solid, mp 188-189° C.; IR (nujol): 3467, 3310, 1648, 1554 cm$^{-1}$; $^1$H NMR (DMSO-d$_6$): δ 8.68 (s, 1H), 8.28 (s, 1H), 7.53 (d, J=8.7 Hz, 2H), 7.26 (s, 1H), 7.23 (d, J=8.7 Hz, 2H), 7.09 (dd, J=8.7, 2.5 Hz, 1H), 6.49 (d, J=8.8 Hz, 1H), 5.16 (d, J=6.4 Hz, 1H), 3.22 (d, J=6.4 Hz, 1H), 2.70 (s, 3H), 1.26 (s, 3H), 1.22 (s, 3H), 1.16 (s, 3H), 1.05 (s, 3H); $^{13}$C NMR (101 MHz, DMSO-d$_6$): δ 152.2, 141.7, 139.5, 138.8, 132.1, 128.6, 121.0, 119.6 (q, J=255.1 Hz), 118.5, 117.7, 117.0, 111.5, 78.2, 57.7, 37.2, 30.9, 28.8, 26.5, 22.9, 17.5. Anal. Calcd. for $C_{22}H_{26}F_3N_3O_3$: C, 60.40; H, 5.99; N, 9.61. Found: C, 60.28; H, 6.15; N, 9.38.

1-(3-Hydroxy-1,2,2,4,4-pentamethyl-1,2,3,4-tetrahydroquinolin-6-yl)-3-(4-(trifluoromethoxy)phenyl) thiourea (13f)

Yield: 0.24 g (0.52 mmol, 60%) as a brown solid, mp 97-99° C.; IR (nujol): 3419, 1605, 1501 cm$^{-1}$; $^1$H NMR (400 MHz, DMSO-d$_6$): δ 9.62 (s, 1H), 9.55 (s, 1H), 7.57 (d, J=8.6 Hz, 2H), 7.29 (d, J=8.6 Hz, 2H), 7.17 (s, 1H), 7.08 (d, J=8.5 Hz, 1H), 6.52 (d, J=8.8 Hz, 1H), 5.19 (d, J=6.4 Hz, 1H), 3.22 (d, J=6.4 Hz, 1H), 2.73 (s, 3H), 1.25 (s, 3H), 1.24 (s, 3H), 1.14 (s, 3H), 1.09 (s, 3H); $^{13}$C NMR (101 MHz, DMSO-d$_6$): δ 179.8, 144.8, 142.4, 139.5, 132.6, 128.7, 125.5, 123.7, 122.7, 121.5, 121.3 (q, J=255.5 Hz), 112.0, 79.0, 58.9, 38.2, 32.0, 29.6, 27.8, 23.9, 18.9. Anal. Calcd. for $C_{22}H_{26}F_3N_3O_2S$: C, 58.26; H, 5.78; N, 9.27. Found: C, 58.34; H, 5.57; N, 9.31.

Other Syntheses and Analyses Relating to Schemes 4-15
The Following Syntheses and Analyses Pertain to Reactions Relevant to Scheme 4

Phenyl 3-methylbut-2-enoate (15)

To an oil-free suspension of NaH (1.34 g, 56.0 mmol) in anhydrous THF (20 mL) at 0° C. (ice bath) was added over a 5-min period with stirring a solution of phenol (14, 5.0 g, 53 mmol) in THF (55 mL). The solution was stirred for 10 min and treated with a solution of 3-methyl-2-butenoyl chloride (7.0 g, 59 mmol) in THF (25 mL) over a 5-min period at 0° C., and was then allowed to warm to room temperature for 3 h. The white suspension was transferred to a separatory funnel containing water (150 mL) and acetic acid (1 mL) and was gently shaken. The mixture was extracted with ether (150 mL), and the extract was washed with saturated NaCl (3×100 mL), dried (MgSO$_4$), filtered, and concentrated to give a light yellow oil. The product was purified on a 40-cm×2.5-cm silica gel column eluted with 10% ether in hexanes to give 15 (8.4 g, 89%) as a colorless oil. IR: 1738, 1653 cm$^{-1}$; $^1$H NMR (400 MHz, CDCl$_3$): δ 7.38 (t, J=7.9 Hz, 2H), 7.20 (t, J=7.8 Hz, 1H), 7.10 (d, J=8.0 Hz, 2H), 5.91 (m, 1H), 2.22 (d, J=1.8 Hz, 3H), 1.96 (d, J=1.8 Hz, 3H); $^{13}$C NMR (101 MHz, CDCl$_3$): δ 164.9, 159.9, 150.7, 129.3, 125.5, 121.8, 115.3, 27.6, 20.5.

4,4-Dimethylchroman-2-one (16)

Into a 500-mL, three-necked, round-bottomed flask equipped with a stir bar, an addition funnel and a condenser (drying tube) was placed dichloromethane (DCM, 164 mL) to which was added AlCl$_3$ (9.87 g, 74.0 mmol). The resulting suspension was stirred and cooled to 0° C. (ice bath), and a solution of 15 (7.4 g, 42.0 mmol) in DCM (40 mL) was added dropwise. The reaction was gradually warmed to room temperature, and stirring was continued for 72 h. The resulting brown solution was added to a mixture of ice and saturated NaCl, the layers were separated, and the aqueous layer was extracted with DCM (100 mL). The combined organic layers were washed with saturated NaCl (2×75 mL), dried (MgSO$_4$), filtered, and concentrated to give a brown oil, which was purified on a 40 cm×2.5 cm silica gel column eluted with 10% ether in hexanes to give 16 (5.00 g, 68%) as a colorless oil. IR: 1769 cm$^{-1}$; $^1$H NMR (400 MHz, CDCl$_3$): δ 7.33 (dd, J=7.4, 1.7 Hz, 1H), 7.25 (td, J=7.9, 1.7 Hz, 1H), 7.15 (td, J=7.5, 1.4 Hz, 1H), 7.05 (dd, J=8.0, 1.4

Hz, 1H), 2.62 (s, 2H), 1.36 (s, 6H); $^{13}$C NMR (101 MHz, CDCl$_3$): δ 168.1, 150.6, 131.7, 128.2, 124.8, 124.4, 117.1, 45.6, 33.2, 27.6.

2-(4-Hydroxy-2,4-dimethylpentan-2-yl)phenol (17)

A solution of 15 (2.5 g, 14.2 mmol) in dry ether (40 mL) was placed in a 250-mL, three-necked, round-bottomed flask equipped with a stir bar, a septum, and a condenser. The solution was cooled to −45° C. (dry ice/acetonitrile bath), and an ether solution of methyllithium (1.6 M, 22.2 mL, 35.5 mmol) was added over 20 min. The reaction was stirred for 18 h with gradual warming to room temperature. The reaction was carefully poured into a mixture of ice and saturated NH$_4$Cl and shaken. The layers were separated, and the aqueous layer was washed with ether (2×50 mL). The combined ether layers were washed with saturated NH$_4$Cl and water, dried (MgSO$_4$), filtered, and concentrated under vacuum. The resulting oil solidified on standing at room temperature. The solid was triturated with 1% ether in pentane and filtered to give 17 (2.72 g, 92%) as a white solid, mp 86-88° C. IR: 3540, 3259, 1372, 753 cm$^{-1}$; $^1$H NMR (400 MHz, CDCl$_3$): δ 7.29 (dd, J=7.8, 1.7 Hz, 1H), 7.07 (td, J=7.7, 1.7 Hz, 1H), 6.88 (td, J=7.5, 1.4 Hz, 1H), 6.65 (br s, 1H), 6.62 (dd, J=7.9, 1.4 Hz, 1H), 2.22 (s, 2H), 1.74 (br s, 1H), 1.48 (s, 6H), 1.12 (s, 6H); $^{13}$C NMR (101 MHz, CDCl$_3$): δ 154.9, 134.4, 127.8, 127.5, 120.7, 117.5, 73.2, 52.4, 37.5, 31.02, 30.95.

2,2,4,4-Tetramethylchroman (18)

A 50-mL, one-necked, round-bottomed flask was charged concentrated phosphoric acid (10 mL). The acid was heated to 100° C., 17 (2.08 g 10 mmol) was added, and the mixture was stirred for 1 h. The crude reaction mixture was cooled, diluted with water, and extracted with ether (3×25 mL). The combined organic layers were washed with saturated NaHCO$_3$ and saturated NaCl, dried (MgSO$_4$), filtered, and concentrated under vacuum. The resulting oil was passed through a 15 cm×2.5 cm column of silica gel eluted with hexanes to give 18 (1.81 g, 95%) as a colorless oil. IR: 1367, 753 cm$^{-1}$; $^1$H NMR (400 MHz, CDCl$_3$): δ 7.19 (dd, J=7.7, 1.4 Hz, 1H), 6.99 (td, J=7.9, 1.4 Hz, 1H), 6.83 (t, J=7.5 Hz, 1H), 6.72 (d, J=8.0 Hz, 1H), 1.76 (s, 2H), 1.28 (s, 6H), 1.27 (s, 6H); $^{13}$C NMR (101 MHz, CDCl$_3$): δ 152.5, 131.5, 127.0, 126.8, 120.6, 117.9, 74.3, 49.3, 32.8, 30.8, 28.6.

2,2,4,4-Tetramethyl-6-nitrochroman (19) and 2,2,4,4-tetramethyl-8-nitrochroman (20)

A 25-mL, three-necked, round-bottomed flask equipped with a magnetic stirrer, an addition funnel, and a nitrogen inlet was charged with 18 (190 mg, 1.0 mmol) and freshly distilled acetic anhydride (625 μL). The solution was cooled to −10° C. (ice/salt bath), and a cold solution of concentrated nitric acid (77 μL) in acetic anhydride (625 μL) was added dropwise over 15 min. The reaction was stirred at −5° C. for 30 min and then diluted with DCM and washed with saturated NaHCO$_3$. The NaHCO$_3$ wash was back-extracted with 20 mL of DCM, and the combined organic layers were washed with water and saturated NaCl, dried (MgSO$_4$), filtered, and concentrated under vacuum. The crude product was purified by preparative thin layer chromatography on a silica gel plate (20 cm×20 cm) using 1% ether in hexanes to give three bands: band 1, recovered 18 (4 mg, 2%) as a colorless oil; band 2, the 6-nitro isomer 19 (78 mg, 33%) as a white solid, mp 64-65° C.; and band 3, the 8-amino isomer 20 (96 mg, 41%) as a white solid, mp 71-72° C. The spectral data for 19 were: IR: 1517, 1339 cm$^{-1}$; $^1$H NMR (400 MHz, CDCl$_3$): δ 8.50 (d, J=2.7 Hz, 1H), 8.00 (dd, J=9.0, 2.7 Hz, 1H), 6.75 (d, J=9.0 Hz, 1H), 1.89 (s, 2H), 1.49 (s, 6H), 1.48 (s, 6H); $^{13}$C NMR (101 MHz, CDCl$_3$): δ 158.5, 141.4, 132.0, 123.6, 123.2, 118.5, 76.4, 48.1, 32.7, 31.2, 28.5. The spectral data for 20 were: IR: 1526, 1365 cm$^{-1}$; $^1$H NMR (400 MHz, CDCl$_3$): δ 7.60 (dd, J=8.0, 1.6 Hz, 1H), 7.48 (dd, J=7.8, 1.6 Hz, 1H), 6.92 (t, J=7.9 Hz, 1H), 1.89 (s, 2H), 1.45 (s, 6H), 1.43 (s, 6H); $^{13}$C NMR (101 MHz, CDCl$_3$): δ 146.6, 140.8, 135.2, 130.9, 122.7, 119.6, 76.9, 48.4, 32.6, 31.4, 28.4.

6-Amino-2,2,4,4-tetramethylchroman (21)

To a stirred solution of 19 (120 mg, 0.51 mmol) in absolute ethanol (5 mL) in a 50-mL, round-bottomed flask was added 5% Pd/C (10 mg), and the mixture was hydrogenated under 1 atm (balloon) of H$_2$ gas for 1.5 h. The reaction was diluted with ether, filtered through CELITE® to remove the catalyst, and concentrated. The resulting red oil was purified by passing through a plug of silica using 10-20% ether in hexanes to give 21 as a yellow oil (71 mg, 68%). IR: 3435, 3358, 3221, 1627, 1498 cm$^{-1}$; $^1$H NMR (400 MHz, CDCl$_3$): δ 6.63 (s, 1H), 6.61 (d, J=7.8 Hz, 1H), 6.47 (dd, J=7.8, 2.7 Hz, 1H), 3.50 (br s, 2H), 1.78 (s, 2H), 1.31 (s, 6H), 1.29 (s, 6H); $^{13}$C NMR (101 MHz, CDCl$_3$): δ 145.4, 139.5, 132.3, 118.3, 114.9, 113.4, 73.8, 49.3, 32.6, 31.0, 28.4.

Syntheses and Analysis of Compounds Shown in Scheme 5

2-(4-Hydroxy-2-methylbutan-2-yl)phenol (22)

A 250-mL, three-necked, round-bottomed flask equipped with a stir bar, a septum, and a condenser was charged with a suspension of 4.18 g (110 mmol) of lithium aluminum hydride in dry THF (50 mL). The solution was cooled to 0° C. (ice bath), and a solution of 16 (5.0 g, 28.4 mmol) in dry THF (50 mL) was added over 1 h. The resulting suspension was stirred at room temperature for 1 h and heated at reflux for 2 h and then cooled in ice. The excess lithium aluminum hydride was destroyed by dropwise addition of 20% ethyl acetate in THF (8 mL). The thick suspension was carefully poured into 150 mL of 1 M H$_2$SO$_4$/ice. This mixture was saturated with NaCl and extracted with ether (3×150 mL). The combined extracts were washed with saturated NaCl (3×100 mL), dried (Na$_2$SO$_4$), filtered, and concentrated under vacuum. The resulting oil solidified upon standing at room temperature. The solid was triturated with 1% ether in pentane and filtered to give 22 (4.60 g, 90%) as a white solid, mp 108-110° C. IR: 3531, 3251 cm$^{-1}$; $^1$H NMR (400 MHz, CDCl$_3$): δ 7.21 (d, J=8.0 Hz, 1H), 7.06 (t, J=8.0 Hz, 1H), 6.85 (d, J=8.0 Hz, 1H), 6.62 (d, J=8.0 Hz, 1H), 5.85 (br s, 1H), 3.53 (t, J=7.0 Hz, 2H), 2.32 (t, J=7.0 Hz, 2H), 1.41 (s, 6H), one alcohol proton not observed; $^{13}$C NMR (101 MHz, CDCl$_3$): δ 154.4, 133.7, 127.6, 127.4, 120.5, 116.6, 61.0, 42.9, 36.7, 28.7.

4,4-Dimethychroman (23)

A solution of 4.25 g (23.6 mmol) of 22 in pyridine (50 mL) was stirred and cooled at 0° C. (ice bath) and then treated with 3.59 g (31.3 mmol) of methanesulfonyl chloride. The reaction was stirred at 0° C. for 1 h and was then poured into saturated NaCl (150 mL) and extracted with ether (3×75 mL). The combined extracts were washed with dilute NaCl (75 mL), 1 M HCl (2×175 mL), and dilute NaCl (2×75 mL), dried (MgSO$_4$) and concentrated to give the mesylate as a yellow oil. The crude mesylate was dissolved in dioxane (50 mL), and the solution was stirred with 1 M NaOH (62.5 mL) at room temperature for 3 h. The two-phased mixture was diluted with saturated NaCl and extracted with ether (3×75 mL). The combined extracts were washed with saturated NaCl (75 mL), dried (MgSO$_4$), filtered, and concentrated under vacuum. The crude product was purified by passing it through a plug of silica gel with 3% ether in hexanes to give 23 (3.64 g, 95%) as a colorless oil. IR: 3065, 3031, 1607, 1579, 1486 cm$^{-1}$; $^1$H NMR (400 MHz, CDCl$_3$): δ 7.26 (d, J=7.7 Hz, 1H), 7.06 (t, J=7.8 Hz, 1H), 6.87 (t, J=7.9 Hz, 1H), 6.78 (d, J=8.2 Hz, 1H), 4.18 (t, J=5.3 Hz, 2H), 1.83 (t, J=5.3 Hz, 2H), 1.32 (s, 6H); $^{13}$C NMR (101 MHz, CDCl$_3$): δ 153.6, 131.6, 127.0, 126.9, 120.4, 116.9, 63.0, 37.7, 31.1, 30.5.

4,4-Dimethyl-6-nitrochroman (24) and
4,4-dimethyl-8-nitrochroman (25)

A 25-mL, three-necked, round-bottomed flask equipped with a magnetic stirrer, an addition funnel, and a nitrogen inlet was charged with 23 (1.10 g, 6.8 mmol) and freshly distilled acetic anhydride (4.25 mL). The solution was cooled to −10° C. (ice/salt bath), and a cold solution of concentrated nitric acid (0.52 mL) in acetic anhydride (4.25 mL) was added dropwise over 30 min. The reaction was stirred at −5° C. for 30 min and was then diluted with DCM and washed with saturated NaHCO$_3$. The NaHCO$_3$ wash was back-extracted with DCM (20 mL), and the combined organic layers were washed with water and saturated NaCl, dried (MgSO$_4$), filtered, and concentrated under vacuum to give 1.25 g of a yellow oil consisting of a 45:55 mixture of 24 and 25. As this product mixture was difficult to purify by chromatography, it was carried on to the 6- and 8-amino compounds, 26 and 27, respectively, before purification.

6-Amino-4,4-dimethylchroman-6-amino (26) and
8-amino-4,4-dimethylaminochroman (27)

A solution of the mixture of 24 and 25 [1.25 g (ca. 6.04 mmol)] was dissolved in a mixture of 90 mL of ethanol and 20 mL of water. To the stirred solution was added ammonium chloride (0.33 g, 6.17 mmol) and iron powder (1.10 g, 19.6 mmol), and the mixture was heated at 85° C. for 2 h. The reaction was filtered through CELITE®, treated with NaHCO$_3$ (50 mL) and extracted with ethyl acetate (2×50 mL). The combined organic extracts were washed with saturated NaCl, dried (Na$_2$SO$_4$), filtered, and concentrated under vacuum. The resulting brown oil was purified on a 30×2.0 cm silica gel column slurry packed in hexane containing increasing concentrations of ether (2-30%). Elution gave two bands: band 1, the 8-amino isomer 27 (552 mg, 52%) as a yellow oil and band 2, the 6-amino isomer 26 (451 mg, 42%) as a yellow oil. The spectral data for 26 were: IR: 3429, 3352, 3230, 1620, 1498 cm$^{-1}$; $^1$H NMR (400 MHz, CDCl$_3$): δ 6.69 (m, 2H), 6.52 (m, 1H), 4.22 (t, J=5.3 Hz, 2H), 3.71 (br s, 2H), 1.80 (t, J=5.3 Hz, 2H), 1.30 (s, 6H); $^{13}$C NMR (101 MHz, CDCl$_3$): δ 141.4, 135.4, 131.4, 120.1, 116.3, 112.5, 63.1, 37.9, 31.1, 30.6. The spectral data for 27 were: IR: 3429, 3356, 3227, 1624, 1499 cm$^{-1}$; $^1$H NMR (400 MHz, CDCl$_3$): δ 6.62 (m, 2H), 6.53 (dd, J=8.6, 2.7 Hz, 1H), 4.11 (t, J=5.3 Hz, 2H), 3.36 (br s, 2H), 1.83 (t, J=5.3 Hz, 2H), 1.31 (s, 6H); $^{13}$C NMR (101 MHz, CDCl$_3$): δ 146.7, 139.4, 132.3, 117.4, 115.1, 113.7, 62.9, 38.0, 31.2, 30.7.

The Following Pertains to Scheme 6

2-(4-Ethyl-4-hydroxy-2-methylhexan-2-yl)phenol
(28)

Compound 28 was prepared on a 10.0 mmol scale from known 4,4-dimethylchroman-2-one (16) and 2.5 eq of ethylmagnesium bromide in ether and was used directly. The yield of 28 was 1.82 g (7.71 mmol, 77%) as a white solid, mp 109-111° C.; IR: 3532, 3206 cm$^{-1}$; $^1$H NMR (400 MHz, CDCl$_3$): δ 7.29 (d, J=7.8 Hz, 1H), 7.20 (br s, 1H), 7.03 (t, J=7.5 Hz, 1H), 6.86 (t, J=7.5 Hz, 1H), 6.53 (d, J=7.8 Hz, 1H), 2.14 (s, 2H), 1.98 (br s, 1H), 1.48 (s, 6H), 1.42 (q, J=7.5 Hz, 4H), 0.78 (t, J=7.4 Hz, 6H); $^{13}$C NMR (101 MHz, CDCl$_3$): δ 155.9, 134.6, 127.6, 127.5, 120.5, 117.5, 77.5, 48.3, 37.3, 31.4, 31.3, 8.0.

2,2-Diethyl-4,4-dimethylchroman (29)

Compound 29 was prepared on a 6.00 mmol scale from 28 and purified according to a procedure described for the preparation of 2,2,4,4-tetramethylchroman (18) as found in the literature [Journal of Medicinal Chemistry, 2004, Vol. 47 pages 1008-1017, and the article entitled "Novel Heteroarotinoids as Potential Antagonists of *Mycobacterium bovis* BCG" by C. W. Brown, S. Liu, J. Klucik, K. D. Berlin. and P. J. Brennan]. The yield of 2,2-diethyl-4,4-dimethylchroman (29) was 1.12 g (5.14 mmol, 86%) as a colorless oil; IR: 1607, 1583 cm$^{-1}$; $^1$H NMR (400 MHz, CDCl$_3$): δ 7.23 (d, J=7.5 Hz, 1H), 7.04 (t, J=8.0 Hz, 1H), 6.86 (t, J=7.5 Hz, 1H), 6.79 (d, J=8.0 Hz, 1H), 1.78 (s, 2H), 1.70 (m, 2H), 1.56 (m, 2H), 1.32 (s, 6H), 0.88 (t, J=7.5 Hz, 6H); $^{13}$C NMR (101 MHz, CDCl$_3$): δ 152.7, 132.3, 127.1, 126.5, 120.7, 118.1, 78.9, 45.6, 33.2, 30.6, 29.4, 8.0.

6-Amino-2,2-diethyl-4,4-dimethylchroman (32) and
8-amino-2,2-diethyl-4,4-dimethylchroman (33)

2,2-Diethyl-4,4-dimethylchroman (29) was nitrated in the usual manner on a 5.00 mmol scale using nitric acid in acetic anhydride at −10° C. as described for 2,2,4,4-tetramethylchroman (18) to give a mixture of the 6-isomer 30 and the 8-nitro isomer 31 as a yellow oil. Since the nitro derivatives were difficult to separate, the mixture was reduced as described for the preparation of 26/27, precursors of series 4 and 5, using ammonium chloride in aqueous ethanol to give the 6-amino (32) and 8-amino (33) compounds in a 6.2:1 ratio (86% crude yield). These isomers were separated on a 30 cm×2.5 cm silica gel column eluted with increasing concentrations of ether in hexanes to give two bands: band 1, the 8-amino isomer (33, 127 mg, 0.55 mmol, 11%) eluted with 10% ether in hexanes and solidified as a light brown oil; band 2, the 6-amino isomer (32, 792 mg, 3.40 mmol, 68%) eluted with 30% ether in hexanes as a tan oil. The spectral data for 33 were: IR: 3466, 3375, 3184, 1611 cm$^{-1}$; $^1$H NMR (400 MHz, CDCl$_3$): δ 6.75-6.67 (complex, 2H), 6.55 (dd, J=7.2, 2.0 Hz, 1H), 3.75 (br s, 2H), 1.80 (s, 2H), 1.76 (m, 2H), 1.60 (m, 2H), 1.32 (s, 6H), 0.90 (t, J=7.5 Hz, 6H); $^{13}$C NMR (101 MHz, CDCl$_3$): δ 139.9, 136.1, 132.0, 120.2, 115.9, 112.4, 79.1, 45.2, 32.9, 30.6, 29.1, 8.0. The spectral data for 32 were: IR: 3429, 3355, 3221, 1624 cm$^{-1}$; $^1$H NMR (400 MHz, CDCl$_3$): δ 6.63 (d, J=8.4 Hz, 1H), 6.62 (s, 1H), 6.46 (dd, J=8.4, 2.8 Hz, 1H), 3.27 (br s, 2H), 1.74 (s, 2H), 1.70 (m, 2H), 1.51 (m, 2H), 1.30 (s, 6H), 0.87 (t, J=7.5 Hz, 6H); ¹³C NMR (101 MHz, CDCl₃): δ 145.5, 139.5, 133.4, 118.5, 114.8, 113.3, 78.6, 45.4, 32.8, 30.8, 29.1, 7.8.

The Following Pertains to Scheme 7

Phenyl 3,3-diethylacrylate (34)

This compound was prepared from phenol (14) and 3-ethyl-2-pentenoyl chloride (obtained by treatment of 3-ethyl-2-pentenoic acid with $SOCl_2$) on a 53 mmol scale and was purified by column chromatography on a 40 cm×2.5 cm silica gel column eluted with 8% ether in hexane. The yield of 34 was 9.96 g (48.8 mmol, 92%) as a colorless oil; IR: 1738, 1640, 1593, 1200 cm⁻¹; ¹H NMR (400 MHz, CDCl₃): δ 7.37 (t, J=7.8 Hz, 2H), 7.20 (t, J=7.4 Hz, 1H), 7.09 (d, J=7.8 Hz, 2H), 5.85 (s, 1H), 2.67 (q, J=7.5 Hz, 2H), 2.27 (qd, J=7.4, 1.2 Hz, 2H), 1.13 (t, J=7.4 Hz, 3H), 1.10 (t, J=7.5 Hz, 3H); ¹³C NMR (101 MHz, CDCl₃): δ 170.8, 164.8, 150.8, 129.3, 125.7, 121.8, 112.8, 31.1, 25.8, 13.0, 12.0.

4,4-Diethylchroman-2-one (35)

This compound was prepared on a 44 mmol scale as described for 4,4-dimethylchroman-2-one (23) and was purified on a 40 cm×2.5 cm silica gel column eluted with 8% ether in hexane. The yield of 35 was 3.12 g (15.2 mmol, 35%) as a light yellow oil; IR: 1776, 1609, 1585, 1202 cm⁻¹; ¹H NMR (400 MHz, CDCl₃): δ 7.28-7.23 (m, 1H), 7.20 (dd, J=7.8, 1.8 Hz, 1H), 7.15 (td, J=7.8, 1.1 Hz, 1H), 7.07 (dd, J=8.1, 1.1 Hz, 1H), 2.63 (s, 2H), 1.79-1.61 (complex, 4H), 0.82 (t, J=7.4 Hz, 6H); ¹³C NMR (101 MHz, CDCl₃): δ 168.9, 151.6, 128.1, 128.0, 126.2, 124.2, 117.3, 39.9, 38.5, 29.9, 8.1.

2-(3-Ethyl-5-hydroxy-5-dimethylhexan-3-yl)phenol (36)

This compound was prepared on a 4.90 mmol scale from 4,4-diethylchroman-2-one (35) and methylmagnesium bromide in ether (−45° C.→rt) and was used without further purification. The yield of 36 was 1.02 g (4.32 mmol, 88%) as a light yellow oil; IR: 3538, 3269, 1601 cm⁻¹; ¹H NMR (400 MHz, CDCl₃): δ 7.29 (dd, J=8.0, 1.7 Hz, 1H), 7.06 (td, J=7.9, 1.1 Hz, 1H), 6.89 (td, J=7.7, 1.1 Hz, 1H), 6.59 (d, J=7.8 Hz, 1H), 2.18 (s, 2H), 2.10 (m, 2H), 1.82 (m, 2H), 1.63 (br s, 2H), 1.10 s, 6H), 0.72 (t, J=7.4 Hz, 6H); ¹³C NMR (101 MHz, CDCl₃): δ 155.0, 132.8, 129.1, 127.3, 120.6, 117.5, 73.2, 45.9, 43.2, 31.1, 26.9, 7.9.

4,4-Diethyl-2,2-dimethylchroman (37)

This compound was prepared and purified on a 4.00 mmol scale according to the procedure described for the preparation of 2,2,4,4-tetramethylchroman (18). The yield of 37 was 0.78 g (3.60 mmol, 90%) as a colorless oil; IR: 1604, 1597, 1483, 1381, 1367, 745 cm⁻¹; ¹H NMR (400 MHz, CDCl₃): δ 7.16 (dd, J=7.8, 1.7 Hz, 1H), 7.07 (ddd, J=8.2, 7.3, 1.7 Hz, 1H), 6.89 (td, J=7.3, 1.7 Hz, 1H), 6.79 (dd, J=8.2, 1.7 Hz, 1H), 1.78 (s, 2H), 1.76-1.61 (complex, 4H), 1.34 (s, 6H), 0.75 (t, J=7.4 Hz, 6H); ¹³C NMR (101 MHz, CDCl₃): δ 154.0, 130.3, 126.9, 126.7, 120.5, 117.9, 74.3, 40.2, 37.4, 33.5, 29.1, 8.4.

6-Amino-4,4-diethyl-2,2-dimethylchroman (40) and 8-amino-4,4-diethyl-2,2-dimethyl-chroman (41)

4,4-Diethyl-2,2-dimethylchroman (37) was nitrated on a 3.50 mmol scale using nitric acid in acetic anhydride at −10° C. as described for 2,2,4,4-tetramethylchroman (18) to give a mixture of the 6-nitro (38) and 8-nitro (39) isomers as a yellow oil. Since the nitro derivatives were difficult to separate, the mixture was reduced as described for the preparation of 26/27 using ammonium chloride in aqueous ethanol to give the 6- and 8-amino compounds (40 and 41, respectively) in a 1:1.2 ratio (84% crude yield). These were separated on a 30 cm×2.5 cm silica gel column eluted with increasing concentrations of ether in hexane to give two bands: band 1, the 8-amino isomer (401 343 mg, 1.47 mmol, 42%) eluted with 10% ether in hexanes and solidified as a tan solid, mp 37-38° C.; band 2, the 6-amino isomer (40, 294 mg, 1.26 mmol, 36%) eluted with 30% ether in hexanes as a tan oil. The spectral data for 41 were: IR: 3471, 3374, 3194, 1612 cm⁻¹; ¹H NMR (400 MHz, CDCl₃): δ 6.72 (t, J=7.7 Hz, 1H), 6.59 (dd, J=7.9, 1.6 Hz, 1H), 6.56 (dd, J=7.6, 1.6 Hz, 1H), 3.73 (br s, 2H), 1.77 (s, 2H), 1.77-1.57 (complex, 4H), 1.35 (s, 6H), 0.75 (t, J=7.4 Hz, 6H); ¹³C NMR (101 MHz, CDCl₃): δ 141.6, 136.1, 130.2, 120.2, 116.5, 112.4, 74.6, 40.4, 37.7, 33.2, 29.2, 8.5. The spectral data for the 40 were: IR: 3434, 3356, 3220, 1626 cm⁻¹; ¹H NMR (400 MHz, CDCl₃): δ 6.62 (d, J=8.4 Hz, 1H), 6.54 (d, J=2.7 Hz, 1H), 6.48 (dd, J=8.4, 2.7 Hz, 1H), 3.37 (bs, 2H), 1.73 (s, 2H), 1.72-1.56 (complex, 4H), 1.30 (s, 6H), 0.76 (t, J=7.4 Hz, 6H); ¹³C NMR (101 MHz, CDCl₃): δ 147.1, 139.5, 131.3, 118.3, 114.6, 113.7, 73.9, 40.4, 37.7, 33.3, 28.9, 8.4.

The Following Pertains to Scheme 8

2-(3,5-Diethyl-5-hydroxyheptan-3-yl)phenol (42) and 2,2,4,4-tetraethylchroman (43)

This compound was prepared from lactone 35 by treatment with 2.5 eq of ethylmagnesium bromide to generate 2-(3,5-diethyl-5-hydroxyheptan-3-yl)phenol (42), followed by ring closure with $H_3PO_4$ to promote formation of 43. The compound was purified by column chromatography to give the chroman as a colorless oil. A small impurity was present and could not be removed. The slightly crude 43 was carried on to the next step.

2,2,4,4-Tetraethyl-6-nitrochroman (44) and 2,2,4,4-tetraaethyl-8-nitrochroman (45)

This compound was prepared by treatment of 43 with nitric acid in acetic anhydride at −10° C. This reaction gave the C-6 and C-8 nitrated products 44 and 45, respectively, which were difficult to separate. Purification by preparative thin layer chromatography gave the C-6 nitrated product 44 (35%) as a light yellow oil. The C-8 nitrated product 45 co-eluted with the impurity cited above and was discarded. Spectral data for 44 were: IR: 1604, 1583, 1618, 1339, 1264 cm⁻¹; ¹H NMR (400 MHz, CDCl₃): δ 8.10 (d, J=2.7 Hz, 1H), 7.98 (dd, J=8.9, 2.7 Hz, 1H), 6.86 (d, J=8.9 Hz, 1H), 1.80 (s, 2H), 1.80-1.54 (complex, 8H), 0.90 (t, J=7.4 Hz, 6H), 0.77 (t, J=7.5 Hz, 6H); ¹³C NMR (101 MHz, CDCl₃): δ 160.6, 141.8, 131.9, 123.9, 123.5, 118.8, 81.5, 37.9, 35.9, 34.0, 30.3, 8.7, 8.2.

2,2,4,4-Tetraethylchroman-6-amine (46)

Nitrochroman 44 (1.00 g, 3.43 mmol) was reduced as described previously for 24 using iron powder and ammonium chloride in aqueous ethanol to give the amine (46, 816 mg, 3.12 mmol, 91%) as a light yellow oil that darkened on exposure to air. IR: 3434, 3354, 3218, 1623, 1495, 1228 cm⁻¹; ¹H NMR (400 MHz, CDCl₃): δ 6.65 (d, J=8.4 Hz, 1H), 6.51 (d, J=2.7 Hz, 1H), 6.48 (dd, J=8.4, 2.7 Hz, 1H), 3.36 (br s, 2H), 1.69 (s, 2H), 1.76-1.44 (complex, 8H), 0.86

(t, J=7.5 Hz, 6H), 0.75 (t, J=7.4 Hz, 6H); $^{13}$C NMR (101 MHz, CDCl$_3$): δ 147.0, 139.5, 132.4, 118.4, 114.3, 113.7, 78.7, 37.8, 37.6, 33.3, 29.6, 8.4, 7.8.

The Following Pertains to Scheme 9

N-(4-Bromophenyl)-3-methylbut-2-enamide (48)

A solution of 3-methylbut-2-enoyl chloride (3.4 mL, 29.0 mmol) in CHCl$_3$ (25 mL) was added dropwise to a stirred solution of 4-bromoaniline (47, 10 g, 58.1 mmol) in CHCl$_3$ (250 mL). The resulting cloudy reaction mixture was refluxed for 5 h, and then was cooled to room temperature and filtered through CELITE®. The filtrate was washed with 1 M HCl (100 mL), saturated NaHCO$_3$, and saturated NaCl, dried (MgSO$_4$), filtered, concentrated under vacuum and recrystallized from ethanol to afford 48 as a white solid (5.5 g, 21.8 mmol, 75%), mp 118-119° C.; IR: 3294, 1663, 1643, 826 cm$^{-1}$; $^1$H NMR (400 MHz, CDCl$_3$): δ 7.42 (m, 4H), 7.23 (br s, 1H), 5.69 (s, 1H), 2.21 (s, 3H), 1.89 (s, 3H); $^{13}$C NMR (101 MHz, CDCl$_3$): δ 165.0, 154.4, 137.3, 131.9, 121.3, 118.3, 116.5, 27.5, 20.0.

6-Bromo-4,4-dimethyl-3,4-dihydroquinolin-2(1H)-one (49)

To a stirred solution of 48 (5.0 g, 19.6 mmol) in 1,2-dichloroethane was added AlCl$_3$ (3.9 g, 29.5 mmol) portionwise, and the mixture was heated to reflux for 1 h. The reaction was cooled to 0° C., quenched with ice-cold water (20 mL), filtered through CELITE and washed with DCM (2×50 mL). The combined organic extracts were washed with saturated NaHCO$_3$ and saturated NaCl, dried (MgSO$_4$), filtered and concentrated under vacuum. Column chromatography eluted with increasing concentrations of ether in hexanes afforded 49 as a brown solid (3.8 g, 14.9 mmol, 76%), mp 151-153° C.; IR: 3201, 1681, 1488, 1368 cm$^{-1}$; $^1$H NMR (400 MHz, CDCl$_3$): δ 9.36 (s, 1H), 7.39 (s, 1H), 7.27 (d, J=8.4 Hz, 1H), 6.75 (d, J=8.4 Hz, 1H), 2.48 (s, 2H), 1.34 (s, 6H); $^{13}$C NMR (101 MHz, CDCl$_3$): δ 171.2, 135.1, 134.6, 130.4, 127.7, 117.5, 116.1, 44.9, 34.1, 27.5.

6-Bromo-4,4-dimethyl-1,2,3,4-tetrahydroquinoline (50)

To a stirred, ice-cooled solution of 49 (3.5 g, 13.8 mmol) in distilled toluene (35 mL) was added dropwise borane-dimethyl sulfide complex (1.4 mL, 14.4 mmol), and the mixture was refluxed for 3 h. The reaction was cooled to room temperature and quenched carefully by dropwise addition of 10% Na$_2$CO$_3$ (10 mL). The resulting biphasic mixture was stirred at room temperature for 15 min, and the layers were separated. The organic phase was dried (MgSO$_4$), filtered and concentrated under vacuum to give 50 as a colorless oil (3.0 g, 12.4 mmol, 90%); IR 3414, 1495, 1282 cm$^{-1}$; $^1$H NMR (400 MHz, CDCl$_3$): δ 7.29 (d, J=2.3 Hz, 1H), 7.07 (dd, J=8.3, 2.3 Hz, 2H), 6.52 (d, J=8.5 Hz, 1H), 3.33 (t, J=5.8 Hz, 2H), 1.76 (t, J=5.8 Hz, 2H), 1.29 (s, 6H); $^{13}$C NMR (101 MHz, CDCl$_3$): δ 140.4, 133.7, 129.5, 129.4, 117.1, 110.6, 38.4, 36.4, 32.0, 30.8.

tert-Butyl 6-bromo-4,4-dimethyl-3,4-dihydroquinoline-1(2H)-carboxylate (51)

A THF (50 mL) solution containing 50 (3.0 g, 12.4 mmol) was cooled to −78° C., and 2.5 M n-BuLi (6 mL, 15.0 mmol) was added dropwise over a period of 30 min. The solution was stirred for 30 min and di-tert-butyl dicarbonate (3.3 g, 14.9 mmol) in THF (15 mL) was added dropwise over a period of 30 min. The reaction mixture was gradually allowed to attain room temperature with stirring for 18 h, and then it was cooled to 0° C. The mixture was quenched by dropwise addition of saturated NH$_4$Cl solution (20 mL). The layers were separated, and the aqueous phase was extracted with ether (2×50 mL). The combined organic extracts were dried (MgSO$_4$), filtered, concentrated and purified by column chromatography (ether in hexanes gradient) to provide 51 as a brown oil (3.8 g, 11.4 mmol, 92%); IR: 1679, 1483, 1367, 1152 cm$^{-1}$; $^1$H NMR (400 MHz, CDCl$_3$): δ 7.52 (d, J=6.6 Hz 1H), 7.36 (d, J=2.4 Hz, 1H), 7.21 (dd, J=6.6, 2.3 Hz, 1H), 3.72-3.69 (m, 2H), 1.74-1.71 (m, 2H), 1.51 (s, 9H), 1.28 (s, 6H); $^{13}$C NMR (101 MHz, CDCl$_3$): δ 153.6, 140.2, 136.3, 128.7, 128.6, 126.0, 116.4, 81.1, 41.6, 38.1, 33.4, 29.9, 28.4.

tert-Butyl-6-azido-4,4-dimethyl-3,4-dihydroquinoline-1(2H)-carboxyate (52) and tert-butyl 6-amino-4,4-dimethyl-3,4-dihydroquinoline-1(2H)-carboxylate (53)

A mixture of 51 (3.5 g, 10.3 mmol), sodium azide (1.3 g, 20.6 mmol), CuI (0.2 g, 1.03 mmol), L-proline (0.35 g, 3.1 mmol), NaOH (0.12 g, 3.14 mmol) and ethanol/water (7:3, 20 mL) was heated to 90° C. in a 35-mL Chemglass pressure vessel (No. CG-1880-02) for 18 h. The reaction mixture was cooled to room temperature, filtered through CELITE® and washed with EtOAc (50 mL). The filtrate was washed with water (2×30 mL) and saturated NaCl, dried (MgSO$_4$) and concentrated under vacuum to provide 52 as a brown oil. This oil was quickly dissolved in methanol (100 mL), transferred to a 250-mL, round-bottomed flask, and 10% Pd/C (0.3 g, 10% w/w) was added under a nitrogen atmosphere. The reaction vessel was flushed with H$_2$ gas, and stirred under H$_2$ (1 atm, balloon) at room temperature for 6 h. The catalyst was removed by filtration through CELITE® and washed with methanol (25 mL). The filtrate was concentrated and purified by column chromatography (hexanes: ether; 4:1) to afford 53 (1.8 g, 6.4 mmol, 62%) as a brown oil. IR: 3448, 3362, 1685, 1503, 138 cm$^{-1}$; $^1$H NMR (400 MHz, CDCl$_3$): δ 7.28 (d, J=1.6 Hz, 1H), 7.12 (d, J=7.2 Hz, 1H), 7.03 (td, J=7.2, 1.6 Hz, 1H), 3.75-3.72 (m, 2H), 1.76-1.73 (m, 2H), 1.52 (s, 9H), 1.30 (s, 6H); $^{13}$C NMR (101 MHz, CDCl$_3$): δ 154.0, 142.1, 139.1, 128.7, 125.5, 113.1, 112.2, 80.3, 41.6, 38.8, 30.2, 28.5, 28.4.

Syntheses of 54 Leading to Series 9 and 10

A solution of 53 (0.2 g, 0.7 mmol) in THF (5 mL) was added to an appropriate isocyanate or isothiocyanate (0.7 mmol) in THF (2 mL) at room temperature under nitrogen. The mixture was stirred until TLC indicated that 53 had been consumed. Evaporation of the solvent generated each member of 54 which were dissolved in DCM. Treatment of each solution with trifluoroacetic acid gave a mixture which was stirred until TLC indicated that members of 54 were absent. The solvent was evaporated and additional DCM was added and then was also evaporated. Water was added, and the mixture was washed with cold ether. The aqueous layer was basified (NaHCO$_3$), and the mixture was extracted with ethyl acetate. The extracts ere combined and washed with water, saturated NaCl, dried, and the solvent was evaporated to give members of 9. To a stirred solution of 9d (0.2 g, 0.6 mmol) in DMF in a 15 mL Chemglass pressure vessel (No. CG1880-01) was added Cs$_2$CO$_3$ (390 mg, 1.2 mmol) and methyl iodide (1.0 mL, 16 mmol). The vessel was closed and stirring was continued at room temperature for 24 hours. Water was added, and the mixture was filtered. The solid was stirred with ethanol for 15 minutes and filtered to give 10 as a light yellow solid (185 mg, 62%), mp 249-251° C., IR: 3297, 3260, 1724, 1598, 843 cm$^{-1}$. $^1$H NMR (400 MHz, CDCl$_3$): δ 9.59 (s, 1H), 9.21 (s, 1H), 8.21 (d, J=8.0 Hz, 2H), 7.88 (d, J=9.2 Hz, 1H), 7.71 (d, J=8.0 Hz, 2H), 7.67 (s, 1H), 7.51 (d, J=9.2 Hz, 1H), 3.89 (s, 6H), 3.56 (s, 6H), 2.11 (s, 2H), 1.36 (s, 6H); $^{13}$C NMR (101 MHz, CDCl$_3$): δ 151.4, 145.4, 139.7, 139.4, 135.0, 124.5, 121.3, 117.4, 116.7, 59.4, 56.1, 31.6, 30.5, 26.8. Anal. Calcd. for C$_{20}$H$_{25}$IN$_4$O$_3$: C, 48.40; H, 5.08; N, 11.29. Found: C, 48.65; H, 5.23; N, 11.52. The Following Pertains to Scheme 10

6-Bromo-2,2,4-trimethyl-1,2-dihydroquinoline (55)

Bismuth(III) triflate (19.0 g, 30.0 mmol) was added to a solution of 4-bromoaniline (47, 25.0 g, 145 mmol) in acetone (500 mL), and the mixture was stirred at reflux for 3 days. The solvent was removed under vacuum, and the residue was partitioned between ether (300 mL) and water (200 mL). The layers were separated, and the aqueous phase was extracted with ether. The combined organic extracts were washed with saturated NaCl and evaporated under vacuum. The crude product was purified by column chromatography (ether in hexanes gradient) to afford 55 as a brown solid (23 g, 89.9 mmol, 62%), mp 83-85° C.; IR: 3382, 1486, 1257, 806 cm$^{-1}$; $^1$H NMR (400 MHz, CDCl$_3$): δ 7.13 (d, J=2.2 Hz, 1H), 7.05 (dd, J=8.4, 2.2 Hz, 1H), 6.31 (d, J=8.4 Hz, 1H), 5.33 (s, 1H), 3.71 (br s, 1H), 1.95 (s, 3H), 1.26 (s, 6H); $^{13}$C NMR (101 MHz, CDCl$_3$): δ 142.2, 130.7, 129.4, 127.6, 126.2, 123.4, 114.3, 108.6, 51.9, 30.9, 18.4.

6-Bromo-1,2,4-tetramethyl-1,2-dihydroquinoline (56)

Sodium hydride (4.5 g of a 60% dispersion in mineral oil, 113.0 mmol) was added to DMF (190 mL) under a nitrogen atmosphere, and the mixture was cooled to 15° C. A solution of 55 (19.0 g, 75.3 mmol) in DMF (75 mL) was added dropwise, the mixture was stirred for 30 min, and then methyl iodide (42.6 g, 18.7 mL, 300 mmol) in DMF (75 mL) was added dropwise. The reaction mixture was warmed to room temperature gradually and stirred for 18 h. The crude reaction mixture was added to water, and the mixture was extracted with ether (2×100 mL). The combined organic extracts were washed with saturated NaCl, dried (MgSO$_4$), filtered and concentrated to provide 56 (16.4 g, 62 mmol, 82%) as a yellow oil; IR: 1488, 1406, 797 cm$^{-1}$; $^1$H NMR (400 MHz, CDCl$_3$): δ 7.16 (dd, J=8.4, 2.4 Hz, 1H), 7.11 (d, J=2.4 Hz, 1H), 6.37 (d, J=8.4 Hz, 1H), 5.32 (d, J=1.5 Hz, 1H), 2.76 (s, 3H), 1.95 (s, 3H), 1.29 (s, 6H); $^{13}$C NMR (101 MHz, CDCl$_3$): δ 144.2, 131.2, 130.9, 127.3, 125.8, 125.2, 112.2, 108.4, 56.3, 30.7, 27.1, 18.5.

6-Bromo-1,2,2,4-tetramethyl-1,2,3,4-tetrahydroquinolin-3-ol (57)

A 1.0 M borane:THF solution (97.0 mmol, 97 mL) was added dropwise to an ice-cooled solution of 14 (13.0 g, 48.8 mmol) in THF (250 mL), and the mixture was stirred at 15° C. for 6 h. A 1:1 solution of THF/H$_2$O (60 mL) was added dropwise to the reaction mixture over 30 min, followed by dropwise addition of 3 M NaOH (50 mL) over 30 min. To this mixture was added 30% aqueous hydrogen peroxide (16.0 mL), and stirring was continued at room temperature for 2 h. The crude reaction mixture was poured into water and extracted with EtOAc (3×150 mL). The combined organic layers were washed with saturated NaHCO$_3$ and saturated NaCl, dried (Na$_2$SO$_4$), filtered and concentrated under reduced pressure. The crude product was purified by flash chromatography (hexane/EtOAc 7:3) to afford 57 as a colorless oil (7.9 g, 27.8 mmol, 57%). IR: 3406, 1589, 1490 cm$^{-1}$; $^1$H NMR (400 MHz, CDCl$_3$): δ 7.24 (d, J=2.4 Hz, 1H), 7.17 (dd, J=8.8, 2.4 Hz, 1H), 6.47 (d, J=8.8 Hz, 1H), 3.27 (d, J=9.4 Hz, 1H), 2.79 (s, 3H), 2.76-2.68 (m, 1H); 1.90 (br s, 1H), 1.41 (d, J=6.8 Hz, 3H), 1.36 (s, 3H), 1.01 (s, 3H); $^{13}$C NMR (101 MHz, CDCl$_3$): δ 144.3, 129.9, 129.7, 128.2, 113.8, 109.0, 58.0, 36.1, 31.6, 24.9, 18.1, 17.0.

6-Bromo-1,2,2,4-tetramethyl-1,2,3,4-tetrahydroquinolin-3-one (58) and 6-Bromo-1,2,2,4,4-pentamethyl-1,4-dihydroquinolin-3(2H)-one (59)

DMSO (2.3 mL, 31.7 mmol) was added dropwise to a solution of oxalyl chloride (1.4 mL, 17.3 mmol) in DCM (60 mL) at −60° C., and the resulting mixture was stirred for 10 min. This mixture was transferred via syringe to a solution of 57 (4.1 g, 14.4 mmol) in DCM (60 mL) at −60° C. The mixture was stirred for 15 min, and then triethylamine (10 mL, 72.0 mmol) was added dropwise over 15 min. The reaction was stirred 1 h and quenched by dropwise addition of water (20 mL). The mixture was stirred with warming to room temperature, and the layers were separated. The organic layer was washed with water (2×20 mL), dried (MgSO$_4$), filtered and concentrated to give 58. The crude product was used directly for the next step without further purification.

To a solution of 58 in THF (20 mL) was added dropwise 26% lithium bis(trimethylsilyl)amide in THF (25 mL, 38.0 mmol) over 10 min at −50° C. The reaction was warmed to −20° C., and iodomethane (2.4 mL, 38.0 mmol) in THF (20 mL) was added dropwise, and stirring was continued with warming to room temperature for 3 h. The reaction mixture was poured into ice-cold water and extracted with EtOAc (2×50 mL). The combined organic layers were washed with saturated NaCl, dried (Na$_2$SO$_4$), filtered and concentrated under vacuum. Purification by column chromatography (hexanes/EtOAc 3:2) gave 59 (2.6 g, 8.9 mmol, 62%) as a colorless oil. IR: 1719, 1486 cm$^{-1}$; $^1$H NMR (400 MHz, CDCl$_3$): δ 7.33 (dd, J=8.6, 2.3 Hz, 1H), 7.29 (d, J=2.3 Hz, 1H), 6.08 (d, J=8.6 Hz, 1H), 2.83 (s, 3H), 1.45 (s, 6H), 1.28 (s, 6H); $^{13}$C NMR (101 MHz, CDCl$_3$): δ 214.4, 144.6, 132.7, 130.4, 127.5, 115.7, 112.4, 64.2, 47.6, 30.9, 23.3, 22.9.

6-Amino-1,2,2,4,4-pentamethyl-1,4-dihydroquinolin-3(2H)-one (60)

Into a 250-mL Chemglass pressure vessel (No. CG-1880-R-03) was added 59 (1.9 g, 6.42 mmol), copper iodide (0.61 g, 3.2 mmol), L-proline (0.74 g, 6.42 mmol), DMF (4.0 mL) and aqueous ammonia (19.0 mL). The reaction mixture was heated to 110° C. for 24 h, and then cooled to room temperature and finally quenched with water (200 mL). The resulting mixture was extracted with EtOAc (3×100 mL), and the extract was dried (MgSO$_4$), filtered and concentrated under vacuum. Purification by column chromatography (EtOAc in hexanes gradient) to give 60 (0.9 g, 3.9 mmol, 65%) as a brown oil. IR: 3422, 3357, 1711, 1501 cm$^{-1}$; $^1$H NMR (400 MHz, CDCl$_3$): δ 6.66-6.60 (m, 3H), 3.35 (br s, 2H), 2.78 (s, 3H), 1.44 (s, 6H), 1.25 (s, 6H); $^{13}$C NMR (101

MHz, CDCl$_3$): δ 215.8, 139.6, 138.6, 132.0, 115.0, 114.5, 112.7, 64.3, 47.7, 31.0, 23.0, 22.9.

The Following Pertains to Scheme 11

General Procedure to Synthesize 11a-f

To a stirred solution of 60 (0.2 g, 0.86 mmol) in THF (5 mL), was added dropwise a series of isocyanates or isothiocyanates (0.86 mmol) in THF (2 mL) at room temperature under a nitrogen atmosphere. The reaction was stirred until TLC analysis indicate the complete consumption of 60. The solvent was evaporated under vacuum, the residue was purified by column chromatography (EtOAc in hexanes gradient), and the product was crystallized from ether in pentane (3:7) to afford the 11a-f.

Ethyl 2,2,4-trimethyl-4-pentenoate (61)

A 1-L, three-necked, round-bottomed flask was charged with a mixture of diisopropylamine (15.9 g, 21.9 mL, 15.7 mmol) in 200 mL of freshly distilled THF. Then n-butyllithium (2.5 M, 63.0 mL, 157.5 mmol) was added to the solution. After about 5 min, ethyl isobutyrate (14.0 g, 120.5 mmol) was added dropwise. Stirring was continued for 1 h at −70° C. A solution of 3-iodo-2-methylpropene (21.9 g, 12.9 mL, 120.5 mmol) in 100 mL of THF was added dropwise, and the mixture was stirred overnight with warming to room temperature. The reaction mixture was poured into a mixture of ice and 1 M HCl, and the product was extracted with ether (3×100 mL). The combined ether extracts were washed with saturated NaCl, dried (MgSO$_4$), filtered, and concentrated. Vacuum distillation afforded 61 (12.8 g, 64%) as a colorless liquid, bp 50° C. (1.8 mm). IR: 3078, 1729, 1645, 895 cm$^{-1}$; $^1$H NMR (300 MHz, CDCl$_3$): δ 4.79 (s, 1H), 4.65 (s, 1H), 4.08 (q, J=7.1 Hz, 2H), 2.31 (s, 2H), 1.66 (s, 3H), 1.25 (t, J=7.1 Hz, 3H), 1.17 (s, 6H); $^{13}$C NMR (75 MHz, CDCl$_3$): δ 177.7, 142.3, 113.9, 60.1, 48.2, 41.7, 25.4, 23.3, 13.9. 2,2,4-Trimethyl-4-pentenoic acid (62)

A 250-mL, round-bottomed flask was charged with 61 (11.2 g, 66.6 mmol) in 25 mL of MeOH, 20% NaOH (30 mL), and the mixture was refluxed overnight at 60-70° C. After cooling to room temperature, 50 mL of water was added, and the mixture was acidified with 1 M HCl. The product was extracted with ether (3×100 mL), and the combined ether extracts were washed with saturated NaCl, dried (MgSO$_4$), filtered, and concentrated. Vacuum distillation afforded acid 62 (9.04 g, 96%) as a colorless liquid, bp 83° C. (1.8 mm). IR: 3077, 1703, 1644, 895 cm$^{-1}$; $^1$H NMR (300 MHz, CDCl$_3$): δ 11.2 (s, 1H), 4.82 (s, 1H), 4.70 (s, 1H), 2.34 (s, 2H), 1.71 (s, 3H), 1.21 (s, 6H); $^{13}$C NMR (75 MHz, CDCl$_3$): δ 185.3, 142.6, 114.8, 48.5, 42.3, 25.7, 23.9.

2,4-Dimethyl-4-penten-2-amine (63)

A 100-mL, three-necked, round-bottomed flask was charged with 62 (2.2 g, 15.6 mmol) and TEA (2.9 g, 4.0 mL, 28.6 mmol) in 25 mL of dry benzene. The flask was cooled to 0° C. (ice bath), and diphenyl phosphoryl azide (6.3 g, 23.2 mmol) was added dropwise with stirring. The reaction mixture was stirred at 0° C. for 1 h, then at room temperature for 1 h, and finally at reflux for 3 h (N$_2$ evolved). The solution was cooled, ether (250 mL) was added, and the organic layer was washed three times with water. The organic layer was dried (Na$_2$SO$_4$), filtered, and concentrated. To the concentrated residue was added a mixture of 15% HCl (10 mL) and AcOH (10 mL), and the mixture was stirred overnight at room temperature. Water was added, and the aqueous layer was washed with ether (3×50 mL). The aqueous layer was cooled (ice bath), basified by dropwise addition of 10% NaOH solution, and the product was extracted with ether (3×50 mL). The combined ether extracts were washed with water, saturated NaCl, and then dried (KOH). The solvent was evaporated to give 63 (1.2 g, 72%) as a light yellow liquid, which was used without purification in the next step. IR: 3355, 2967, 1639, 891 cm$^{-1}$; $^1$H NMR (300 MHz, CDCl$_3$): δ 4.91 (s, 1H), 4.72 (s, 1H), 2.10 (s, 2H), 1.82 (s, 3H), 1.32 (br s, 2H), 1.13 (s, 6H); $^{13}$C NMR (75 MHz, CDCl$_3$): δ 143.4, 114.8, 52.8, 46.5, 31.3, 25.5.

N-(2,4-Dimethyl-4-penten-2-yl)-4-nitroaniline (64)

A 35-mL Chemglass pressure vessel (No. CG-1880-02), equipped with a magnetic stirrer, was charged with the amine 63 (2.2 g, 19.7 mmol) and 1-fluoro-4-nitrobenzene (2.5 g, 17.7 mmol) in DMSO (15 mL). The vessel was sealed under nitrogen and heated at 80° C. for 48 h. After cooling to room temperature, water was added, and the product was extracted with ether (3×75 mL). The combined extracts were washed with water and saturated NaCl, dried (Na$_2$SO$_4$), filtered and concentrated to give a yellow oil, which was chromatographed using 5-15% ether in hexane to afford 64 (1.8 g, 45%) as a yellow oil. IR: 3379, 1599, 1531, 1368, 834 cm$^{-1}$; $^1$H NMR (300 MHz, CDCl$_3$): δ 8.05 (d, J=9.3 Hz, 2H), 6.61 (d, J=9.3 Hz, 2H), 4.94 (s, 1H), 4.72 (s, 1H), 4.63 (br s, 1H), 2.46 (s, 2H), 1.76 (s, 3H), 1.44 (s, 6H); $^{13}$C NMR (75 MHz, CDCl$_3$): δ 152.7, 142.2, 136.3, 126.6, 116.3, 113.3, 54.3, 48.4, 28.8, 24.9.

N-(2,2,4-Trimethyl-4-penten-2-yl)-N-methyl-4-nitroaniline (65)

A system was charged with 64 (70 mg, 0.3 mmol) in 5 mL of DMF. Sodium hydride (50 mg, 2 mmol) was added, and the mixture was stirred for 5 min, and then methyl iodide (3.0 g, 0.6 mmol) was added dropwise. Stirring was continued overnight at room temperature. Aqueous NH$_4$Cl (5 mL) was added, and the product was extracted with ether (3×10 mL). The ether extracts were washed with water and saturated NaCl, dried (MgSO$_4$), filtered, and concentrated to give a yellow oil, which was chromatographed using 10-20% ether in hexane to afford 65 (70 mg, 99%) as a yellow oil. IR: 1591, 1502, 1307, 837 cm$^{-1}$; $^1$H NMR (300 MHz, CDCl$_3$): δ 8.06 (d, J=9.3 Hz, 2H), 6.95 (d, J=9.3 Hz, 2H), 4.91 (s, 1H), 4.75 (s, 1H), 3.02 (s, 3H), 2.47 (s, 2H), 1.72 (s, 3H), 1.41 (s, 6H); $^{13}$C NMR (75 MHz, CDCl$_3$): δ 156.6, 142.7, 137.4, 124.8, 119.7, 115.5, 59.6, 47.2, 37.5, 28.6, 24.6.

N$^1$-(2,2,4-Trimethyl-4-penten-2-yl)-N$^1$-methyl-1,4-benzenediamine (66)

A 250-mL round-bottomed flask was charged with 65 (2.0 g, 8.1 mmol), iron powder (3.0 g, 53.7 mmol, >100 mesh) and NH$_4$Cl (1.0 g, 18.6 mmol) in 100 mL of EtOH:H$_2$O (3.6:1). The mixture was heated to 85° C. under N$_2$ for 2 h. The reaction mixture was filtered through CELITE, treated with saturated NaHCO$_3$ (100 mL), and extracted with EtOAc (3×100 mL). The combined extracts were washed with saturated NaCl, dried (Na$_2$SO$_4$), filtered, and concentrated to afford a brown residue (1.67 g, 95%), which was spectroscopically pure and used directly for the next reaction step. IR: 3348, 1551 cm$^{-1}$; $^1$H NMR (300 MHz, CDCl$_3$): δ 6.97 (d, J=7.8 Hz, 2H), 6.58 (d, J=8.7 Hz, 2H), 4.84 (s, 1H), 4.71 (s, 1H), 3.81 (s, 2H), 2.72 (s, 3H), 2.22 (s, 2H), 1.81 (s, 3H), 1.06 (s, 6H); $^{13}$C NMR (75 MHz, CDCl$_3$): δ 144.1, 143.5, 129.5, 115.0, 114.6, 113.5, 58.2, 46.5, 37.3, 25.7, 25.3.

N-[4-(2,4-Dimethyl-4-penten-2-yl)methylamino) phenyl]acetamide (67)

To a mixture of 66 (1.0 g, 4.7 mmol) in pyridine (20 mL) in a 200-mL round-bottomed flask was added dropwise acetyl chloride (3.3 g, 3.0 mL, 42.1 mmol). The mixture was stirred at room temperature for 2-3 h. The crude reaction mixture was added to water (100 mL), and the product was extracted with ether (3×50 mL). The combined ether extracts were washed with saturated NaCl, dried (MgSO$_4$), filtered, and concentrated, to give a brown residue, which was purified by chromatography using 30% ether in hexane to afford 67 (1.2 g, 97%) as a light yellow solid, mp 74-75° C. IR: 3297, 1663, 887 cm$^{-1}$; $^1$H NMR (300 MHz, CDCl$_3$): δ 7.45 (s, 1H), 7.37 (d, J=7.1 Hz, 2H), 7.09 (d, J=7.1 Hz, 2H), 4.86 (s, 1H), 4.73 (s, 1H), 2.75 (s, 3H), 2.23 (s, 2H), 2.15 (s, 3H), 1.82 (s, 3H), 1.08 (s, 6H); $^{13}$C NMR (75 MHz, CDCl$_3$): δ 168.7, 147.6, 143.9, 134.3, 128.8, 120.0, 114.7, 58.1, 46.6, 37.1, 26.0, 25.2, 24.8.

N-(1,2,2,4,4-Pentamethyl-1,2,3,4-tetrahydroquinolin-6-yl)acetamide (68)

A modified procedure of Faure (Faure, R., Pommier, A.; Pons, J. M.; Michel Rajzmann, M.; Santelli, M. Formation of 2-cyclohexenoes by Friedel-Crafts acylation of alkenes with β, γ-ethylenic acyl halides, *Tetrahedron*, 1992, 48, 8419-8430) was followed. A mixture of AlCl$_3$ (5.0 g, 37.4 mmol) in 75 mL of DCM in a 200-mL, three-necked, round-bottomed flask was cooled at −78° C. (dry ice/acetone). Amide 27 (0.9 g, 3.4 mmol) in 15 mL of DCM was added dropwise. Stirring was continued overnight with gradual warming to room temperature. The process was monitored by TLC. The reaction mixture was poured onto crushed ice, and the aqueous phase was extracted with DCM (3×50 mL). The combined organic extracts were washed with saturated NaHCO$_3$, water, and saturated NaCl, dried (MgSO$_4$), filtered, and concentrated to give a brown residue, which was chromatographed using 5-20% EtOAc in hexane to afford semisolid 68 (0.45 g, 53%). IR: 3289, 1655, 1610, 806 cm$^{-1}$; $^1$H NMR (300 MHz, CDCl$_3$): δ 8.08 (s, 1H), 7.28-7.22 (m, 2H), 6.52 (d, J=8.2 Hz, 1H), 2.72 (s, 3H), 2.08 (s, 3H), 1.74 (s, 2H), 1.26 (s, 3H), 1.19 (s, 3H); $^{13}$C NMR (75 MHz, CDCl$_3$): δ 169.0, 142.9, 134.4, 128.3, 125.4, 123.8, 120.1, 112.6, 54.5, 53.2, 32.8, 31.7, 31.5, 27.8, 24.5.

1,2,2,4,4-Pentamethyl-1,2,3,4-tetrahydroquinolin-6-amine (69)

A 25-mL, round-bottomed flask was charged with amide 68 (0.15 g, 0.6 mmol) and 10 mL of 70% (v/v) of H$_2$SO$_4$, and the mixture was refluxed overnight. After cooling to room temperature, 10 mL of water was added, and the mixture was basified with 30% NaOH. The amine was extracted with EtOAc (3×15 mL). The combined organic extracts were dried (Na$_2$SO$_4$), filtered and concentrated to give 69 (0.15 g, 92%) as a brown residue. This compound was used without further purification. IR: 3336, 1623 cm$^{-1}$; $^1$H NMR (300 MHz, CDCl$_3$): δ 6.64 (s, 1H), 6.50 (s, 2H), 3.64 (s, 2H), 2.69 (s, 3H), 1.74 (s, 2H), 1.28 (s, 6H), 1.17 (s, 6H); $^{13}$C NMR (75 MHz, CDCl$_3$): δ 139.3, 137.2, 135.8, 114.7, 114.2, 114.0, 53.4, 32.1, 31.7, 27.4 (several signals overlap).

The Following Pertains to Scheme 12

6-Amino-1,2,2,4,4-pentamethyltetrahydroquinolin-3-ol (70)

To a stirred solution of 60 (0.2 g, 0.86 mmol) in THF (10 mL) was added portion-wise lithium aluminum hydride (65.0 mg, 1.72 mmol) at 0° C. The reaction was stirred at room temperature for 4 h, quenched with saturated Na$_2$SO$_4$ at 0° C., filtered through CELITE® and extracted with EtOAc (20 mL). The organic layer was washed with water, saturated NaCl, dried (Na$_2$SO$_4$), filtered and concentrated to give 70 as a brown oil. The residue was dissolved in THF (5 mL), and the solution was added dropwise at room temperature to an iso(thio)cyanate (0.86 mmol) in THF. When TLC analysis indicated the disappearance of 70, the reaction mixture was concentrated under vacuum and purified by column chromatography (EtOAc in hexanes gradient). Concentration of the major fraction and crystallization from DCM/ether mixture (2:8) afforded 13a-f.

The Following Pertains to Scheme 13

N-(4-(2-Methyl-4-oxopentan-2-yl)thio)phenyl)acetamide (72)

To a stirred solution of acetamidothiophenol (25.0 g, 149.7 mmol) in dry CHCl$_3$ (20 mL) was added triethylamine (15.1 g, 20.8 mL, 149.7 mmol), followed by mesityl oxide (71, 14.7 g, 17.1 mL, 149.7 mmol). The resulting slurry was heated to reflux at 70° C. Two additional portions of triethylamine (7.5 g, 10.4 mL, 74.5 mmol) and 71 (7.4 g, 8.6 mL, 74.5 mmol) were added at regular intervals of 4 h, and the resulting solution was refluxed for 16 h after the final addition. The resulting reaction mixture was cooled, filtered through CELITE® and washed with chloroform (2×50 mL). The combined organic layers were washed with water (2×100 mL), saturated NaCl solution, dried (MgSO$_4$), filtered and concentrated under vacuum to give a yellow oil. The crude reaction mixture was then purified by silica gel column chromatography eluted with DCM:EtOAc (1:1) to afford 72 as a pale yellow solid, mp 49-51° C. (lit [5] mp 46-49° C.); IR: 3310, 1699, 1676 cm$^{-1}$; $^1$H NMR (400 MHz, CDCl$_3$): δ 7.90 (br s, 1H, NH), 7.53 (d, 1H, J=8.8 Hz, 2H, Ar—H), 7.45 (d, J=8.8 Hz, 2H, Ar—H), 2.65 (s, 2H, CH$_2$), 2.19 (s, 3H, CH$_3$), 2.15 (s, 3H, CH$_3$), 1.36 (s, 6H, 2CH$_3$); $^{13}$C NMR (101 MHz, CDCl$_3$): δ 206.9, 168.6, 139.0, 138.3, 126.2, 119.6, 54.3, 47.0, 32.1, 28.0, 24.5.

N-{4-[(4-Hydroxy-2,4-dimethylpentan-2-yl)thio]phenyl}acetamide (73)

To a stirred solution of methyllithium in Et$_2$O (198 mL, 317 mmol, 1.6 M) in THF (300 mL) at −50° C. was added dropwise a solution of 72 (28 g, 105.7 mmol) in THF (200 mL) over 30-45 min. The reaction formed a white precipitate and the reaction was slowly warmed to room temperature over a period of 3 h. Stirring was continued at room temperature for 1 h. The reaction was then cooled to 0° C., and the mixture was quenched by dropwise addition of ice water (150 mL). After adjusting the solution pH to 6-7 by addition of 6 M HCl, the solution was extracted with EtOAc (2×250 mL). The combined organic extracts were washed with saturated NaCl (1×150 mL), dried (MgSO$_4$), filtered and concentrated under vacuum to afford a dark brown liquid. To the crude product was added CHCl$_3$ (60 mL) with cooling to 0° C. for 1 h which afforded a yellow solid. The solid was then filtered and dried under vacuum to afford 73 (18 g, 61%) as a pale yellow solid, mp 141-142° C. (lit[5] mp 138-144° C.); IR: 3400, 3303, 1676 cm$^{-1}$; $^1$H NMR (400 MHz, CDCl$_3$): δ 7.68 (br s, 1H, NH), 7.52 (m, 4H, Ar—H), 3.50 (br s, 1H, OH), 2.19 (s, 3H, CH$_3$), 1.77 (s, 2H, CH$_2$), 1.34 (s, 6H, 2CH$_3$), 1.33 (s, 6H, 2CH$_3$); $^{13}$C NMR (101 MHz, CDCl$_3$): δ 168.4, 138.8, 138.1, 126.3, 119.6, 72.0, 52.0, 49.2, 32.2, 30.8, 24.6.

N-(2,2,4,4-Tetramethylthiochroman-6-yl)acetamide (74)

To a stirred solution of 73 (18.0 g, 64.1 mmol) in chlorobenzene (125 mL) at 60° C. anhydrous aluminum chloride (10.2 g, 76.7 mmol) was added portion-wise over a period of 45 min (Caution: This addition was exothermic and typically raised the temperature of the solvent to its boiling point. External heating was discontinued before adding the aluminum chloride). Once the addition was complete, heating was continued at reflux for an additional 90 min. The reaction mixture was cooled to room temperature and quenched with ice cold water (150 mL) to give a thick suspension. The solid was removed by filtration through CELITE® and washed with EtOAc (2×100 mL). The layers were separated, and the aqueous layer was extracted with additional EtOAc (2×100 mL). The combined organic extracts were washed with saturated NaCl, dried (MgSO$_4$), filtered and concentrated under vacuum to give a yellow oil. The crude product was purified on a silica gel column using hexanes: EtOAc (1:1) to afford product 74 (15.0 g, 89%) as a pale yellow solid, mp 105-107° C. (lit[5] mp 104-107° C.); IR: 3295, 1662 cm$^{-1}$; $^1$H NMR (400 MHz, CDCl$_3$): δ 7.60 (br s, 1H, NH), 7.27 (d, J=2.3 Hz, 1H, Ar—H), 7.20 (dd, J=8.2, 2.3 Hz, 1H, Ar—H), 7.04 (d, J=8.2 Hz, 1H, Ar—H), 2.16 (s, 3H, CH$_3$), 1.92 (s, 2H, CH$_2$), 1.39 (s, 6H, 2CH$_3$), 1.35 (s, 6H); $^{13}$C NMR (101 MHz, CDCl$_3$): δ 168.3, 143.4, 135.1, 128.4, 128.2, 118.7, 118.2, 54.4, 42.0, 35.7, 32.4, 31.4, 24.4.

2,2,4,4-Tetramethylthiochroman-6-amine Hydrochloride (75)

To a stirred solution of 74 (15.0 g, 57.0 mmol) in MeOH (25 mL) was added 12 M HCl (100 mL) and the mixture was heated to 90° C. for 1 h. The reaction mixture was cooled, and concentrated to ¼ of its initial volume. The resulting crude mixture was cooled to 0° C. (ice bath) for 1 h to yield a white solid. The solid was filtered and dried under vacuum to afford 75 as a white powder (14.0 g, 95%), mp 208-209° C.; IR: 2922, 2853 cm$^{-1}$; $^1$H NMR (400 MHz, DMSO-d$_6$): δ 10.08 (s, 2H, NH$_2$), 7.48 (s, 1H, Ar—H), 7.22 (d, J=8.3 Hz, 1H, Ar—H), 7.09 (d, J=8.3 Hz, 1H, Ar—H), 1.94 (s, 2H, CH$_2$), 1.42 (s, 6H, 2CH$_3$), 1.40 (s, 6H, 2CH$_3$); $^{13}$C NMR (101 MHz, DMSO-d$_6$): δ 144.2, 132.0, 130.0, 129.1, 122.0, 121.2, 53.5, 42.6, 35.8, 32.6, 31.6.

6-Isothiocyanato-2,2,4,4-tetramethylthiochroman (76)

To a stirred solution of 75 10 g, 38.8 mmol) in EtOH (20 mL), CS$_2$ (29.0 g, 22.9 mL, 381 mmol) was added followed by Et$_3$N (8.03 g, 11.1 mL, 79.5 mmol). The reaction mixture was stirred for a period of 20 min followed by the addition of (Boc)$_2$O (8.46 g, 38.8 mmol) dissolved in ethanol (5 mL). To this reaction, DABCO (0.130 g, 1.2 mmol, 3 mol %) in EtOH (2 mL) was added immediately and the reaction mixture was kept in an ice bath for 10 min, followed by stirring the reaction mixture at room temperature for 20 min. The reaction mixture was concentrated under vacuum. The reaction was dissolved in Et$_2$O (3×100 mL) and washed with saturated NaCl (50 mL). The organic layer was dried (MgSO$_4$), filtered and concentrated to dryness. The compound was further purified on a silica gel column eluted with increasing concentrations of EtOAc in hexanes to afford isocyanate 76 (9.40 g, 92%) as a white solid, mp 192-193° C.; IR: 2140 cm$^{-1}$; $^1$H NMR (400 MHz, DMSO-d$_6$): δ 7.50 (s, 1H, Ar—H), 7.32 (d, J=8.3 Hz, 1H, Ar—H), 7.24 (d, J=8.3 Hz, 1H, Ar—H).

Synthesis of Compounds Shown in Scheme 14

Utilizing the key intermediate 77, the free base of 75, members of 14 could be realized. The one-step process in Scheme 14 involved a condensation of 77 with a variety of isocyanates and isothiocyanates to generate a variety of substituted members of 14.

Synthesis of Compounds Shown in Scheme 15, Including Special Synthesis of Desmethyl Representative (14v)

N-(4-((3-Methylbut-2-en-1-yl)thio)phenyl)acetamide (78)

To a stirred solution of acetamidothiphenol (7, 5.0 g, 30.0 mmol) in acetone (25 mL), K$_2$CO$_3$ (8.26 g, 60.0 mmol) was added followed by the addition of 1-bromo-3-methylbut-2-ene (5.51 g, 36.5 mmol) and the mixture was refluxed for 6 h. The reaction was concentrated to dryness, the residue was extracted with EtOAc (3×50 mL), the extracts were washed with saturated NaCl (50 mL), dried (MgSO$_4$), filtered and concentrated. The crude product was purified on a silica gel column eluted with increasing concentrations of EtOAc in hexanes to obtain pure 78 (5.9 g, 84%) as a colorless oil. $^1$H NMR (400 MHz, CDCl$_3$): δ 7.43 (d, J=8.3 Hz, 2H, Ar—H), 7.30 (d, J=8.3 Hz, 2H, Ar—H), 5.27 (t, J=7.6 Hz, 1H, =CHCH$_2$), 3.49 (d, J=7.6 Hz, 2H, =CHCH$_2$), 2.17 (s, 3H, CH$_3$CO), 1.54 (s, 3H, CH$_3$), 1.20 (s, 3H, CH$_3$) (NH missing); $^{13}$C NMR (101 MHz, CDCl$_3$): δ 168.4, 136.5, 136.3, 131.7, 131.5, 120.2, 119.4, 33.1, 25.7, 24.6, 17.7.

N-(4,4-Dimethylthiochroman-6-yl)acetamide (79)

To stirred polyphosphoric acid (10 g) at 70° C., 78 (4.00 g, 17.0 mmol) was added and heating was continued for 2 h. The reaction mixture was cooled at 0° C., poured into ice-cold water and stirred for 2 h. The compound was extracted with EtOAc (3×50 mL), washed with saturated NaHCO$_3$ (100 mL), saturated NaCl (50 mL), dried (MgSO$_4$), filtered and concentrated under vacuum. The product was purified on a silica gel column eluted with increasing concentrations of EtOAc in hexanes to give 79 (2.88 g, 72%) as a colorless liquid. IR: 3305, 1662 cm$^{-1}$; $^1$H NMR (400 MHz, CDCl$_3$): δ 7.60 (br s, 1H, NH), 7.27 (d, J=2.3 Hz, 1H, Ar—H), 7.20 (dd, J=8.2, 2.3 Hz, 1H, Ar—H), 7.04 (d, J=8.2 Hz, 1H, Ar—H), 2.16 (s, 3H, CH$_3$CO), 2.72 (t, J=4.1 Hz, 2H, CH$_2$), 1.90 (t, J=4.1 Hz, 2H, CH$_2$S), 1.39 (s, 6H, 2CH$_3$); $^{13}$C NMR (101 MHz, CDCl$_3$): δ 168.3, 143.4, 135.1, 128.4, 128.2, 118.7, 118.2, 54.4, 35.7, 32.4, 24.4. 20.1.

4,4-Dimethylthiochroman-6-amine hydrochloride (80)

To a stirred solution of 79 (2.7 g, 11.5 mmol) in methanol (15 mL) was added 6 M HCl (15 mL). The reaction mixture was heated to 90° C. for 1 h, followed by cooling to room temperature. The reaction was concentrated to ¼ of its initial volume and then was cooled to 0° C. for 1 h to yield a solid. The solid was filtered and dried under vacuum to afford 80 as an off-white solid (2.27 g, 86%), mp 214-216° C.; IR: 2926, 2794 cm$^{-1}$; $^1$H NMR (DMSO-d$_6$): δ 10.08 (s, 2H, NH$_2$), 7.48 (s, 1H, Ar—H), 7.22 (d, J=8.3 Hz, 1H, Ar—H), 7.09 (d, J=8.3 Hz, 1H, Ar—H), 2.70 (t, J=4.1 Hz, 2H, CH$_2$S) 1.94 (t, J=4.1 Hz, 2H, CH$_2$), 1.40 (s, 6H, 2CH$_3$); $^{13}$C NMR (DMSO-d$_6$): δ 144.2, 132.0, 130.0, 129.1, 122.0, 121.2, 53.5, 42.6, 35.8, 20.4.

1-(4,4-dimethyl-6-yl)-3-(4-nitrophenyl)thiourea
(14v)

Neutralization of the salt 80 gave the free base. The free base (0.100 g, 0.44 mmol) in THF:DCM (1:1, 5 mL) was treated with 4-nitrophenylisothiocyanate (0.46 mmol), followed by Et$_3$N (0.53 mmol, 0.54 g, 74 μL, 1.2 equiv.). The mixture was stirred at 23° C. for 18 h and was then decomposed. Separation of the organic phase gave a reside which was concentrated and then subjected to chromatography on silica gel with increasing concentrations of EtOAc in hexanes to yield 14v as a light yellow solid (0.134 g, 82%), mp 142-143° C.; $^1$H NMR (400 MHz, DMSO-d$_6$): δ 10.34 (s, 1H, NH), 10.20 (s, 1H, NH), 8.20 (d, J=8.8 Hz, 2H, Ar—H), 7.83 (d, J=8.8 Hz, 2H, Ar—H), 7.54 (s, 1H, Ar—H), 7.20 (d, J=8.4 Hz, 1, Ar—H), 7.01 (d, J=8/5 Hz, 1H, Ar—H), 3.02 (d, J=6.0 Hz, 2H, CH$_2$S), 1.89 (d, J=6.0 Hz, 2H, CH$_2$), 1.26 (s, 6H, 2 CH$_3$); $^{13}$C NMR (101 MHz, DMSO-d$_6$): δ 179.4, 146.8, 142.7, 142.4, 135.6, 128.3, 126.5, 124.9, 122.8, 122.4, 121.9, 37.4, 33.3, 30.4, 22.8. Anal. Calcd. for C$_{18}$H$_{19}$N$_3$O$_2$S$_2$: C, 57.89; H, 5.13; N, 11.25. Found: C, 58.02; H, 5.26; N, 11.32.

Example 4

Non small cell lung cancer (NSCLC) is especially difficult to treat with KEYTRUDA® (pembrolizumab) (www.keytruda.com/non-small-cell-lung-cancer/monotherapy), OPDIVO® (nivolumab) (www.opdivo.com/advanced-nscle?utm_source=google), or ZYKADIA® (ceritinib) (www.zykadia.com/patient-support/financial). Many side effects occur with these clinical agents. Thus, new agents are needed.

Several compounds related to SHetA2 have exhibited strong activity against Non-Small Cell Lung Cancer (NSCLC) [Yi-D Lin, S. Chen, P. Yue, W. Zou, D. et. al. Cancer Res. 2008, 68, 5335-5344. Y. Lin, X. Lui, P. Yue, D. M. Benbrook, et. al. Molecular Cancer Therapeutics. 2008, 7, 3556-3565.] When tested using methods known to those of skill in the art, the new compounds disclosed herein also kill NSCLC cancer cells and display activity against lung cancer.

While this invention is susceptible of embodiment in many different forms, there is shown in the drawings, and will herein be described hereinafter in detail, some specific embodiments of the instant invention. It should be understood, however, that the present disclosure is to be considered an exemplification of the principles of the invention and is not intended to limit the invention to the specific embodiments or algorithms so described.

It is to be understood that the terms "including", "comprising", "consisting" and grammatical variants thereof do not preclude the addition of one or more components, features, steps, or integers or groups thereof and that the terms are to be construed as specifying components, features, steps or integers.

If the specification or claims refer to "an additional" element, that does not preclude there being more than one of the additional element.

It is to be understood that where the claims or specification refer to "a" or "an" element, such reference is not be construed that there is only one of that element.

It is to be understood that where the specification states that a component, feature, structure, or characteristic "may", "might", "can" or "could" be included, that particular component, feature, structure, or characteristic is not required to be included.

Where applicable, although state diagrams, flow diagrams or both may be used to describe embodiments, the invention is not limited to those diagrams or to the corresponding descriptions. For example, flow need not move through each illustrated box or state, or in exactly the same order as illustrated and described.

Methods of the present invention may be implemented by performing or completing manually, automatically, or a combination thereof, selected steps or tasks.

The term "method" may refer to manners, means, techniques and procedures for accomplishing a given task including, but not limited to, those manners, means, techniques and procedures either known to, or readily developed from known manners, means, techniques and procedures by practitioners of the art to which the invention belongs.

For purposes of the instant disclosure, the term "at least" followed by a number is used herein to denote the start of a range beginning with that number (which may be a range having an upper limit or no upper limit, depending on the variable being defined). For example, "at least 1" means 1 or more than 1. The term "at most" followed by a number is used herein to denote the end of a range ending with that number (which may be a range having 1 or 0 as its lower limit, or a range having no lower limit, depending upon the variable being defined). For example, "at most 4" means 4 or less than 4, and "at most 40%" means 40% or less than 40%. Terms of approximation (e.g., "about", "substantially", "approximately", etc.) should be interpreted according to their ordinary and customary meanings as used in the associated art unless indicated otherwise. Absent a specific definition and absent ordinary and customary usage in the associated art, such terms should be interpreted to be ±10% of the base value.

When, in this document, a range is given as "(a first number) to (a second number)" or "(a first number)-(a second number)", this means a range whose lower limit is the first number and whose upper limit is the second number. For example, 25 to 100 should be interpreted to mean a range whose lower limit is 25 and whose upper limit is 100. Additionally, it should be noted that where a range is given, every possible subrange or interval within that range is also specifically intended unless the context indicates to the contrary. For example, if the specification indicates a range of 25 to 100 such range is also intended to include subranges such as 26-100, 27-100, etc., 25-99, 25-98, etc., as well as any other possible combination of lower and upper values within the stated range, e.g., 33-47, 60-97, 41-45, 28-96, etc. Note that integer range values have been used in this paragraph for purposes of illustration only and decimal and fractional values (e.g., 46.7-91.3) should also be understood to be intended as possible subrange endpoints unless specifically excluded.

It should be noted that where reference is made herein to a method comprising two or more defined steps, the defined steps can be carried out in any order or simultaneously (except where context excludes that possibility), and the method can also include one or more other steps which are carried out before any of the defined steps, between two of the defined steps, or after all of the defined steps (except where context excludes that possibility).

Furthermore, it should be noted that terms of approximation (e.g., "about", "substantially", "approximately", etc.) are to be interpreted according to their ordinary and customary meanings as used in the associated art unless indicated otherwise herein. Absent a specific definition within this disclosure, and absent ordinary and customary usage in the associated art, such terms should be interpreted to be plus or minus 10% of the base value.

Still further, additional aspects of the instant invention may be found in one or more appendices attached hereto and/or filed herewith, the disclosures of which are incorporated herein by reference as if fully set out at this point.

Thus, the present invention is well adapted to carry out the objects and attain the ends and advantages mentioned above as well as those inherent therein. While the inventive device has been described and illustrated herein by reference to certain preferred embodiments in relation to the drawings attached thereto, various changes and further modifications, apart from those shown or suggested herein, may be made therein by those of ordinary skill in the art, without departing from the spirit of the inventive concept the scope of which is to be determined by the following claims.

REFERENCES

Waugh, K. M.; Berlin, K. D.; Ford, W. T.; Holt, E. M.; Carroll, J. P.; Schomber, P. R.; Schiff, L. J. Synthesis and characterization of selected heteroarotinoids. Pharmacological activity as assessed in vitamin A deficient hamster tracheal organ cultures. Single crystal X-ray diffraction analysis of 1-(1-1-dioxa3,4-dihydro-4,4-dimethyl-2H-1-benzothiopyran-6-yl)ethanone and ethyl (E)-4-[2-(3,4-dihydro-4,4-dimethyl-2H-1-benzothiopyran-6-yl)-1-propenyl]benzoate. J. Med. Chem. 1985, 27, 116-124; Spruce, L. W.; Rajadhyaksha, S. N.; Berlin, K. D.; Gale, J. B.; Miranda, E. T.; Ford, W. T.; Blossey, E. C.; Verma, A. K.; Hossain, M. B. van der Helm, D.; Breitman, T. R. Heteroarotinoids. Synthesis, characterization and biological activity in terms of an assessment of these systems to inhibit induction of ornithine decarboxylase activity and to induce terminal differentiation of HL-60 cells. J. Med. Chem. 1987, 30, 1474-1482; Gale, J. B.; Rajadhyaksha, S. N.; Spruce, L. W.; Berlin, K. D.; Ji, X.; Slagle, A.; van der Helm, D. Heteroarotinoids: Analytical criteria for the rapid identification of (F)- and (Z)-isomers of these novel retinoids via NMR, UV, and X-ray analyses of selected examples. J. Org. Chem. 1990, 55, 3984-3991; Spruce, L. W.; Gale, J. B.; Berlin, K. D.; Verma, A. K.; Breitman, T. R.; Ji, X.; van der Helm, D. Novel Heteroarotinoids: Synthesis and biological activity. J. Med. Chem. 1991, 34, 430-439; Benbrook, D. M.; Madler, M. M.; Spruce, L. W.; Birckbichler, P. J.; Nelson, E, C.; Subramanian, S.; Weerasekare, G. M.; Gale, J. B.; Patterson, Jr., M. K.; Wang, B.; Wang, W.; Lu, S.; Rowland, T. C.; DiSivestro, P.; Lindamood, C.; Hill, D. L.; and Berlin, K. D. Biologically active heteroarotinoids exhibit anticancer activity and decreased toxicity. J. Med. Chem. 1997, 40, 3567-3583; Benbrook, D. M.; Subramanian, S.; Gale, J. B.; Liu, S.; Brown, C. W.; Boehm, M. F.; Berlin, K. D. Synthesis and characterization of heteroarotinoids demonstrates structure-activity relationships. J. Med. Chem. 1998, 41, 3753-3757; Dhar, A.; Liu, S.; Klucik, J.; Berlin, K. D.; Madler, M. M.; Lu, S.; Ivey, R. T.; Zacheis, D.; Brown, C. W.; Nelson, E. C.; Birckbichler, P. J.; Benbrook, D. M. Synthesis, structure-activity relationships, and RAR-γ-ligand interactions of nitrogen heteroarotinoids. J. Med. Chem. 1999, 42, 3602-3614.

What is claimed is:

1. A method of treating cancer in a subject in need thereof, comprising administering to the subject a therapeutically effective amount of a compound selected from the group consisting of

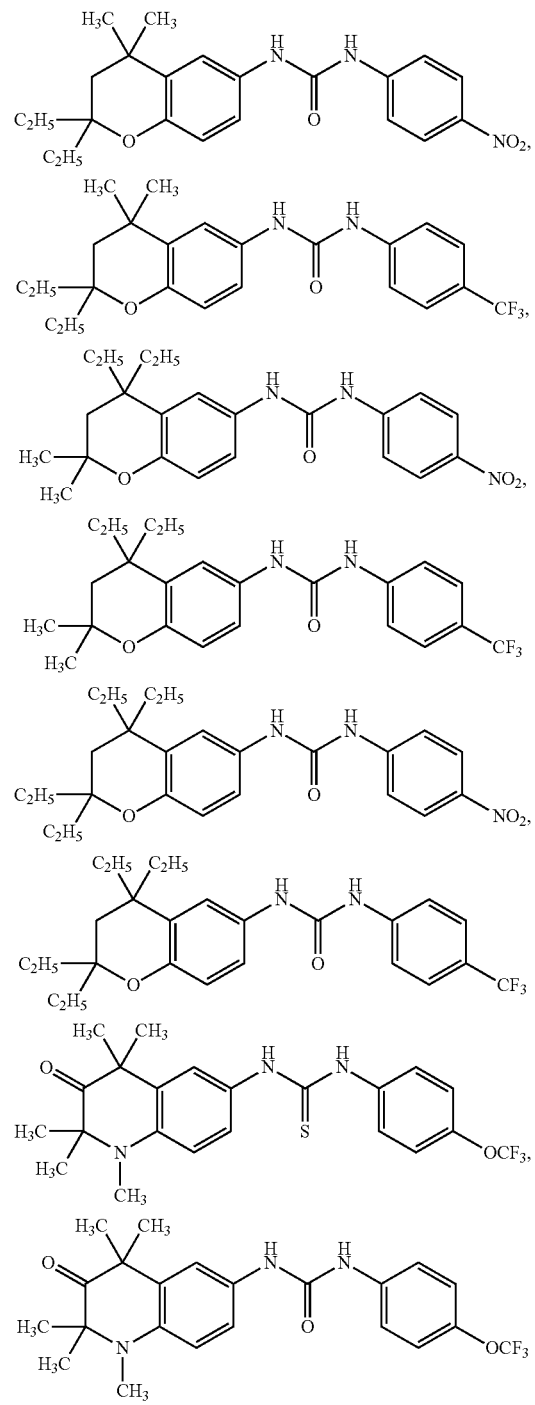

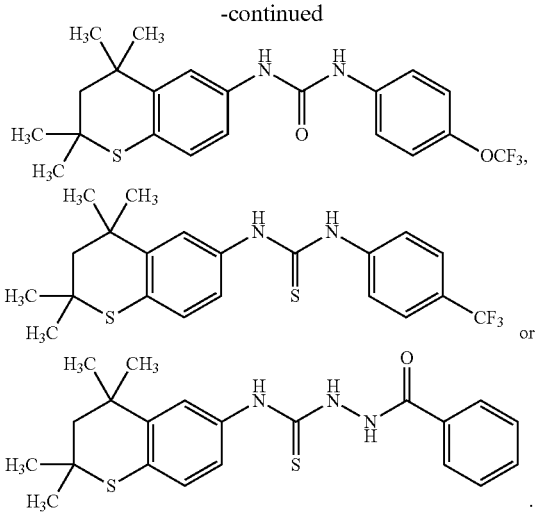
or a salt, solvate, or hydrate thereof.
2. The method of claim 1, wherein the cancer is ovarian cancer or small cell lung cancer.
3. A method of killing cancer cells, comprising contacting the cells with an amount of a compound
selected from the group consisting of
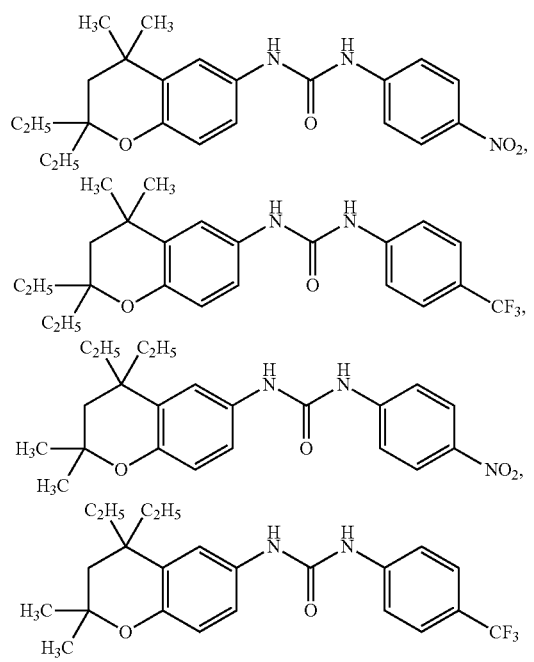
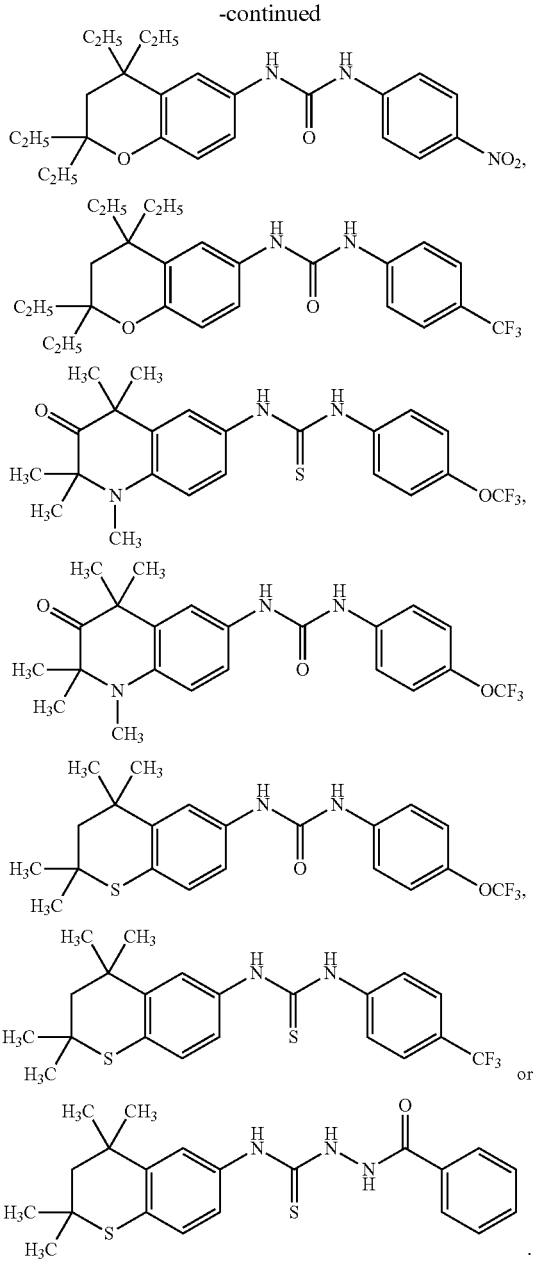
or a salt, solvate, or hydrate thereof.
4. The method of claim 3, wherein the cancer cells are ovarian cancer cells.
* * * * *